(12) United States Patent
van Walsem et al.

(10) Patent No.: US 9,084,467 B2
(45) Date of Patent: Jul. 21, 2015

(54) PROCESS FOR GAMMA-BUTYROLACTONE PRODUCTION

(75) Inventors: Johan van Walsem, Acton, MA (US); Erik Anderson, Somerville, MA (US); John Licata, Wakefield, MA (US); Kevin A. Sparks, Scituate, MA (US); William R. Farmer, Concord, MA (US); Christopher Mirley, Winthrop, MA (US); Jeffrey A. Bickmeier, Arlington, MA (US); Ann D'Ambruoso, Waltham, MA (US); Frank A. Skraly, Watertown, MA (US); Thomas M. Ramseier, Newton, MA (US); Melarkode S. Sivasubramanian, Wayland, MA (US); Yossef Shabtai, Concord, MA (US)

(73) Assignee: Metabolix, Inc., Cambridge, MA (US)

( * ) Notice: Subject to any disclaimer, the term of this patent is extended or adjusted under 35 U.S.C. 154(b) by 82 days.

(21) Appl. No.: 13/578,214

(22) PCT Filed: Feb. 11, 2011

(86) PCT No.: PCT/US2011/024612
§ 371 (c)(1),
(2), (4) Date: Aug. 9, 2012

(87) PCT Pub. No.: WO2011/100601
PCT Pub. Date: Aug. 18, 2011

(65) Prior Publication Data
US 2013/0046075 A1 Feb. 21, 2013

Related U.S. Application Data

(60) Provisional application No. 61/303,584, filed on Feb. 11, 2010, provisional application No. 61/413,195, filed on Nov. 12, 2010, provisional application No. 61/382,855, filed on Sep. 14, 2010.

(51) Int. Cl.
*C08G 63/08* (2006.01)
*A45D 40/00* (2006.01)

(52) U.S. Cl.
CPC .................. *A45D 40/0068* (2013.01)

(58) Field of Classification Search
CPC ......... C12P 7/625; C07C 51/00; C07C 51/09; C08G 63/06; C08G 63/08; C08G 63/78
USPC ............... 435/135, 253, 6; 514/557; 523/113; 528/361
See application file for complete search history.

(56) References Cited

U.S. PATENT DOCUMENTS

| | | | |
|---|---|---|---|
| 2,361,036 A | 10/1944 | Kung | |
| 4,652,685 A | 3/1987 | Cawse et al. | |
| 6,117,658 A * | 9/2000 | Dennis et al. | 435/135 |
| 6,623,730 B1 | 9/2003 | Williams et al. | |
| 7,641,706 B1 | 1/2010 | McMurry et al. | |
| 8,084,626 B1 | 12/2011 | Fruchey et al. | |
| 8,100,990 B2 | 1/2012 | Ellens et al. | |
| 2009/0075351 A1 | 3/2009 | Burk et al. | |
| 2010/0228067 A1 | 9/2010 | Peterson et al. | |
| 2010/0304453 A1 | 12/2010 | Trawick et al. | |
| 2012/0315681 A1 | 12/2012 | Van Walsem et al. | |
| 2014/0024769 A1 | 1/2014 | van Walsem et al. | |

FOREIGN PATENT DOCUMENTS

| | | |
|---|---|---|
| EP | 2360137 A1 | 12/2010 |
| WO | WO 03/051813 A1 | 6/2003 |
| WO | WO 2010/092304 A2 | 8/2010 |
| WO | WO 2013/082284 A1 | 6/2013 |
| WO | WO 2013/085361 A2 | 6/2013 |

OTHER PUBLICATIONS

Zhang et al (Microbial production of 4-hydroxybutyrate, poly-4-hydroxybutyrate, and poly(3-hydroxybutyrate-co-4-hydroxybutyrate) by recombinant microorganisms, Applied genetics and biotechnology, Applied Microbiol Biotechnol (2009) 84: 909-916, published May 12, 2009.*
International Preliminary Report on Patentability, PCT/US2011/024612, date of mailing Aug. 23, 2012.
Kim et al., "Thermal Degradation of Poly-4-hydroxybutyrate", *Polymer Degradation and Stability*, 91, p. 2333, 2006.
Kim et al., "Effect of Metal Compounds on the Thermal Degradation Behavior of Aliphatic Poly(hydroxyalkanoic Acids", *Polymer Degradation and Stability*, 93, p. 776, 2008.
Abate et al., "Separation and Structural Characterization of Cyclic and Open Chain Oligomers Produced in Partial Pyrolysis of Microbial PHB's", *Macromolecules*, 28, p. 7911, 1995.
Notification of Transmittal of the International Search Report and the Written Opinion of the International Searching Authority, or the Declaration, for International Application No. PCT/US2011/024612, dated Jun. 28, 2011, consisting of 15 pages.
Abe, H., "Thermal Degradation of Environmentally Degradable Poly(Hydroxyalkanoic Acid)s," Macromolecular Bioscience, 6:469-486 (2006).
Morikawa, H., et al., "Pyrolysis of Bacterial Polyalkanoates," Canadian Journal of Chemistry, 59:2306-2313(1981).
Zhang, L., et al., "Microbial production of 4-hydroxybutyrate, poly-4-hydroxybutyrate, and poly (3-hydroxybutyrate-co-4-hydroxybutyrate) by recombinant microorganisms,"2 Applied Microbiology and Biotechnology, 84:909-916 (2009).

* cited by examiner

*Primary Examiner* — Gregory Listvoyb

(74) *Attorney, Agent, or Firm* — Hamilton, Brook, Smith & Reynolds, P.C.

(57) ABSTRACT

Processes and methods for making biobased gamma-butyrolactone from renewable carbon resources are described herein.

30 Claims, 7 Drawing Sheets

SEQUENCE LISTING

```
<160> NUMBER OF SEQ ID NOS: 12

<210> SEQ ID NO 1
<211> LENGTH: 2901
<212> TYPE: DNA
<213> ORGANISM: Medicago sativa

<400> SEQUENCE: 1
atggcaaaca aaatggaaaa gatggcaagc attgacgcgc aactgcgcca gttggtcccg      60
gcaaaagtca gcgaggacga caaattgatt gaatacgatg ctctgttgct ggaccgcttt     120
ctggacattc tgcaagatct gcatggcgag gatctgaagg attcggttca ggaagtttac     180
gaactgtctg cggagtatga gcgtaagcat gacccgaaga agctggaaga gctgggtaac     240
ttgattacga gctttgacgc gggcgacagc attgtcgtgg cgaaatcgtt ctctcatatg     300
ctgaatctgg cgaacctggc cgaagaagtt caaattgctc accgccgtcg taacaagctg     360
aagaagggtg attttcgtga tgagagcaat gcgaccaccg agtccgatat tgaggagact     420
ctgaagaaac tggtttttcga catgaagaag tctccgcaag aagtgtttga cgcgttgaag     480
aatcagaccg tggacctggt gctgacggca catcctaccc agagcgttcg ccgttccctg     540
ctgcaaaagc atggtcgtgt tcgtaattgc ttgagccagc tgtatgcgaa agacattacc     600
ccggatgaca aacaagagct ggacgaggca ctgcagcgtg aaatccaggc agcgttccgt     660
accgatgaaa tcaaacgtac cccgccgacc ccacaagacg aaatgcgtgc tggcatgagc     720
tatttccacg aaaccatctg gaagggcgtc ccgaagttcc tgcgtcgcgt ggacaccgcg     780
ttgaagaaca tcggcattaa cgaacgcgtg ccgtataacg ccccgctgat tcaattcagc     840
agctggatgg gtggcgaccg tgacggcaat ccgcgtgtta cgccagaagt gacccgtgat     900
gtttgtctgc tggcgcgtat gatggcggcg aatttgtact atagccagat tgaagatctg     960
```

-continued

```
atgtttgagc tgtctatgtg gcgctgtaat gatgagttgc gtgtgcgtgc cgaagaactg    1020
caccgcaata gcaagaaaga cgaagttgcc aagcactaca tcgagttctg gaagaagatc    1080
ccgttgaacg agccgtaccg tgttgttctg ggtgaggtcc gcgataagct gtatcgcacc    1140
cgtgagcgca gccgttatct gctggcacac ggttattgcg aaattccgga ggaggcgacc    1200
tttaccaacg tggatgaatt tctggaaccg ctggagctgt gttatcgtag cctgtgcgcg    1260
tgcggtgacc gcgcgattgc ggacggttct tgctggatt tcctgcgcca ggtgagcacg     1320
tttggtctga gcctggtccg tctggatatc cgtcaggaat cggaccgcca tacggatgtg    1380
atggacgcta ttaccaaaca cctggaaatt ggcagctacc aggagtggag cgaggagaaa    1440
cgtcaagagt ggctgctgag cgagctgatc ggtaagcgtc cgctgttcgg tccagatctg    1500
ccgcaaaccg acgaaatccg cgacgttctg gacacctttc gtgtgattgc cgaactgccg    1560
agcgacaact tcggcgcgta cattatctcc atggccaccg ccccgagcga tgtcctggca    1620
gtcgagctgc tgcaacgcga atgtaaggtc cgtaacccgt gcgcgtggt tccgctgttt     1680 gaaaagctgg atgacctgga gagcgcaccg gccgcactgg ctcgtctgtt tagcattgac    1740
tggtacatta accgtattga tggtaaacag gaagtgatga ttggttactc cgacagcggt    1800
aaagatgcgg gtcgttttag cgccgcatgg cagctgtaca aggcacaaga agatctgatc    1860
aaggttgcac agaagttcgg cgttaaactg accatgttcc acggtcgcgg tggtacggtt    1920
ggccgtggtg gcggcccaac ccacctggcg attctgagcc aaccgccgga gactatccat    1980
ggttccttgc gtgtcaccgt ccagggcgaa gtgattgagc aaagcttcgg cgaggaacat    2040
ctgtgctttc gcaccctgca gcgttttacg gccgcgactt tggaacacgg catgcgtccg    2100
ccatccagcc caaagccaga atggcgtgcg ctgatggacc aaatggcggt tatcgcgacc    2160
gaggagtatc gcagcattgt gttcaaagag ccgcgttttg tggagtattt ccgtttggca    2220
acgccggaga tggagtacgg ccgcatgaat atcggcagcc gtccggcaaa acgtcgcccg    2280
tccggcggca tcgagacgct gcgtgccatc ccgtggattt tcgcgtggac gcagacccgt    2340
ttccatttgc cggtgtggct gggtttcggt gccgcctttc gtcaagtcgt gcagaaggac    2400
gtgaagaatc tgcatatgct gcaggagatg tacaaccagt ggccgttctt tcgtgtcacc    2460
attgatctgg tggaaatggt cttttgcgaaa ggtgatccgg gcatcgcggc gttgaatgac    2520
cgtctgctgg tttccaaaga cctgtggcct tttggtgaac agctgcgtag caagtacgag    2580
gaaaccaaga aactgctgtt gcaagttgcg gcgcacaagg aggtgctgga aggtgaccct    2640
tatctgaagc aacgcctgcg tctgcgtgac tcgtacatca cgaccctgaa tgtctttcag    2700
gcgtataccc tgaagcgtat ccgtgacccg aattacaaag tggaagttcg ccctccgatc    2760
agcaaggaga gcgcggagac tagcaaacca gcggacgaac tggtcaccct gaatccgacc    2820
tcggagtatg ctccgggttt ggaagatacg ctgattctga cgatgaaggg tatcgcggct    2880
ggcatgcaga acacgggcta a                                              2901
```

<210> SEQ ID NO 2
<211> LENGTH: 966
<212> TYPE: PRT
<213> ORGANISM: Medicago sativa

<400> SEQUENCE: 2

Met Ala Asn Lys Met Glu Lys Met Ala Ser Ile Asp Ala Gln Leu Arg
  1               5                  10                  15

Gln Leu Val Pro Ala Lys Val Ser Glu Asp Asp Lys Leu Ile Glu Tyr

-continued

```
                20                  25                  30
Asp Ala Leu Leu Leu Asp Arg Phe Leu Asp Ile Leu Gln Asp Leu His
                35                  40                  45
Gly Glu Asp Leu Lys Asp Ser Val Gln Glu Val Tyr Glu Leu Ser Ala
            50                  55                  60
Glu Tyr Glu Arg Lys His Asp Pro Lys Lys Leu Glu Glu Leu Gly Asn
 65                  70                  75                  80
Leu Ile Thr Ser Phe Asp Ala Gly Asp Ser Ile Val Val Ala Lys Ser
                85                  90                  95
Phe Ser His Met Leu Asn Leu Ala Asn Leu Ala Glu Glu Val Gln Ile
                100                 105                 110
Ala His Arg Arg Asn Lys Leu Lys Lys Gly Asp Phe Arg Asp Glu
                115                 120                 125
Ser Asn Ala Thr Thr Glu Ser Asp Ile Glu Glu Thr Leu Lys Lys Leu
            130                 135                 140
Val Phe Asp Met Lys Lys Ser Pro Gln Glu Val Phe Asp Ala Leu Lys
145                 150                 155                 160
Asn Gln Thr Val Asp Leu Val Leu Thr Ala His Pro Thr Gln Ser Val
                165                 170                 175
Arg Arg Ser Leu Leu Gln Lys His Gly Arg Val Arg Asn Cys Leu Ser
            180                 185                 190
Gln Leu Tyr Ala Lys Asp Ile Thr Pro Asp Asp Lys Gln Glu Leu Asp
            195                 200                 205
Glu Ala Leu Gln Arg Glu Ile Gln Ala Ala Phe Arg Thr Asp Glu Ile
            210                 215                 220
Lys Arg Thr Pro Pro Thr Pro Gln Asp Glu Met Arg Ala Gly Met Ser
225                 230                 235                 240
Tyr Phe His Glu Thr Ile Trp Lys Gly Val Pro Lys Phe Leu Arg Arg
                245                 250                 255
Val Asp Thr Ala Leu Lys Asn Ile Gly Ile Asn Glu Arg Val Pro Tyr
                260                 265                 270
Asn Ala Pro Leu Ile Gln Phe Ser Ser Trp Met Gly Gly Asp Arg Asp
            275                 280                 285
Gly Asn Pro Arg Val Thr Pro Glu Val Thr Arg Asp Val Cys Leu Leu
            290                 295                 300
Ala Arg Met Met Ala Ala Asn Leu Tyr Tyr Ser Gln Ile Glu Asp Leu
305                 310                 315                 320
Met Phe Glu Leu Ser Met Trp Arg Cys Asn Asp Glu Leu Arg Val Arg
                325                 330                 335
Ala Glu Glu Leu His Arg Asn Ser Lys Lys Asp Glu Val Ala Lys His
            340                 345                 350
Tyr Ile Glu Phe Trp Lys Lys Ile Pro Leu Asn Glu Pro Tyr Arg Val
            355                 360                 365
Val Leu Gly Glu Val Arg Asp Lys Leu Tyr Arg Thr Arg Glu Arg Ser
            370                 375                 380
Arg Tyr Leu Leu Ala His Gly Tyr Cys Glu Ile Pro Glu Glu Ala Thr
385                 390                 395                 400
Phe Thr Asn Val Asp Glu Phe Leu Glu Pro Leu Glu Leu Cys Tyr Arg
                405                 410                 415
Ser Leu Cys Ala Cys Gly Asp Arg Ala Ile Ala Asp Gly Ser Leu Leu
            420                 425                 430
Asp Phe Leu Arg Gln Val Ser Thr Phe Gly Leu Ser Leu Val Arg Leu
            435                 440                 445
```

```
Asp Ile Arg Gln Glu Ser Asp Arg His Thr Asp Val Met Asp Ala Ile
            450                 455                 460
Thr Lys His Leu Glu Ile Gly Ser Tyr Gln Glu Trp Ser Glu Glu Lys
465                 470                 475                 480
Arg Gln Glu Trp Leu Leu Ser Glu Leu Ile Gly Lys Arg Pro Leu Phe
                485                 490                 495
Gly Pro Asp Leu Pro Gln Thr Asp Glu Ile Arg Asp Val Leu Asp Thr
            500                 505                 510
Phe Arg Val Ile Ala Glu Leu Pro Ser Asp Asn Phe Gly Ala Tyr Ile
        515                 520                 525
Ile Ser Met Ala Thr Ala Pro Ser Asp Val Leu Ala Val Glu Leu Leu
530                 535                 540
Gln Arg Glu Cys Lys Val Arg Asn Pro Leu Arg Val Val Pro Leu Phe
545                 550                 555                 560
Glu Lys Leu Asp Asp Leu Glu Ser Ala Pro Ala Ala Leu Ala Arg Leu
                565                 570                 575
Phe Ser Ile Asp Trp Tyr Ile Asn Arg Ile Asp Gly Lys Gln Glu Val
                580                 585                 590
Met Ile Gly Tyr Ser Asp Ser Gly Lys Asp Ala Gly Arg Phe Ser Ala
            595                 600                 605
Ala Trp Gln Leu Tyr Lys Ala Gln Glu Asp Leu Ile Lys Val Ala Gln
            610                 615                 620
Lys Phe Gly Val Lys Leu Thr Met Phe His Gly Arg Gly Gly Thr Val
625                 630                 635                 640
Gly Arg Gly Gly Gly Pro Thr His Leu Ala Ile Leu Ser Gln Pro Pro
                645                 650                 655
Glu Thr Ile His Gly Ser Leu Arg Val Thr Val Gln Gly Glu Val Ile
            660                 665                 670
Glu Gln Ser Phe Gly Glu Glu His Leu Cys Phe Arg Thr Leu Gln Arg
        675                 680                 685
Phe Thr Ala Ala Thr Leu Glu His Gly Met Arg Pro Pro Ser Ser Pro
        690                 695                 700
Lys Pro Glu Trp Arg Ala Leu Met Asp Gln Met Ala Val Ile Ala Thr
705                 710                 715                 720
Glu Glu Tyr Arg Ser Ile Val Phe Lys Glu Pro Arg Phe Val Glu Tyr
                725                 730                 735
Phe Arg Leu Ala Thr Pro Glu Met Glu Tyr Gly Arg Met Asn Ile Gly
                740                 745                 750
Ser Arg Pro Ala Lys Arg Arg Pro Ser Gly Gly Ile Glu Thr Leu Arg
            755                 760                 765
Ala Ile Pro Trp Ile Phe Ala Trp Thr Gln Thr Arg Phe His Leu Pro
770                 775                 780
Val Trp Leu Gly Phe Gly Ala Ala Phe Arg Gln Val Val Gln Lys Asp
785                 790                 795                 800
Val Lys Asn Leu His Met Leu Gln Glu Met Tyr Asn Gln Trp Pro Phe
                805                 810                 815
Phe Arg Val Thr Ile Asp Leu Val Glu Met Val Phe Ala Lys Gly Asp
                820                 825                 830
Pro Gly Ile Ala Ala Leu Asn Asp Arg Leu Leu Val Ser Lys Asp Leu
            835                 840                 845
Trp Pro Phe Gly Glu Gln Leu Arg Ser Lys Tyr Glu Glu Thr Lys Lys
            850                 855                 860
```

```
Leu Leu Leu Gln Val Ala Ala His Lys Glu Val Leu Glu Gly Asp Pro
865                 870                 875                 880

Tyr Leu Lys Gln Arg Leu Arg Leu Arg Asp Ser Tyr Ile Thr Thr Leu
            885                 890                 895

Asn Val Phe Gln Ala Tyr Thr Leu Lys Arg Ile Arg Asp Pro Asn Tyr
        900                 905                 910

Lys Val Glu Val Arg Pro Pro Ile Ser Lys Glu Ser Ala Glu Thr Ser
        915                 920                 925

Lys Pro Ala Asp Glu Leu Val Thr Leu Asn Pro Thr Ser Glu Tyr Ala
        930                 935                 940

Pro Gly Leu Glu Asp Thr Leu Ile Leu Thr Met Lys Gly Ile Ala Ala
945                 950                 955                 960

Gly Met Gln Asn Thr Gly
                965

<210> SEQ ID NO 3
<211> LENGTH: 1362
<212> TYPE: DNA
<213> ORGANISM: Clostridium kluyveri

<400> SEQUENCE: 3
atgtccaacg aggttagcat taaggagctg attgagaagg cgaaagtggc gcagaaaaag      60
ctggaagcgt atagccaaga gcaagttgac gttctggtca aggcgctggg taaagttgtg     120
tacgacaacg ccgagatgtt cgcgaaagag gcggtggagg aaaccgagat gggtgtttac     180
gaggataaag tggctaaatg tcatctgaaa tctggtgcaa tctggaatca cattaaagat     240
aagaaaaccg ttggtattat caaggaagaa ccggagcgtg cgctggtgta cgtcgcgaag     300
cctaaaggtg ttgtggcggc gacgacccct atcaccaatc ctgtggttac cccgatgtgt     360
aacgcgatgg cagcaattaa aggtcgcaac accatcattg tcgccccgca tccgaaggcg     420
aagaaggtga gcgcgcacac cgtggagctg atgaatgcag aactgaaaaa gttgggtgcg     480
ccggaaaaca ttatccagat cgttgaagcc ccaagccgtg aagcagccaa ggagttgatg     540
gagagcgcag acgtggttat cgccacgggt ggcgcaggcc gtgttaaagc agcgtactcc     600
tccggccgtc cggcatacgg tgtcggtccg ggcaattctc aggtcattgt cgataagggt     660
tacgattata taaaagctgc ccaggacatc attaccggcc gcaagtatga caacggtatc     720
atttgcagct ctgagcagag cgtgatcgca ccggcggagg actacgacaa ggtcatcgcg     780
gctttcgtcg agaatggcgc gttctatgtc gaggatgagg aaactgtgga gaaattccgt     840
agcacgctgt tcaaggatgg caagatcaat agcaaaatca tcggtaaatc cgtgcagatc     900
atcgctgacc tggctggtgt caaggtgccg gaaggcacca aggtgatcgt gttgaagggc     960
aagggtgccg tgaaaagga cgttctgtgc aaggagaaaa tgtgcccggt cctggttgcc    1020
ctgaaatatg acacctttga ggaggcggtc gagatcgcga tggccaacta tgtacgag      1080 ggtgcgggcc ataccgccgg tatccacagc gataacgacg agaatatccg ctacgcgggt    1140
acggtgctgc caatcagccg tctggttgtc aaccagccag caactacggc cggtggtagc    1200
tttaacaatg ttttaatcc gaccaccacc ttgggctgcg gtagctgggg ccgtaactcc    1260
attagcgaga acctgacgta tgagcatctg attaatgtca gccgtattgg ctatttcaat    1320
aaggaggcaa aagttcctag ctacgaggag atctggggtt aa                      1362

<210> SEQ ID NO 4
<211> LENGTH: 453
<212> TYPE: PRT
```

-continued

<213> ORGANISM: Clostridium kluyveri

<400> SEQUENCE: 4

Met Ser Asn Glu Val Ser Ile Lys Glu Leu Ile Glu Lys Ala Lys Val
1               5                   10                  15

Ala Gln Lys Lys Leu Glu Ala Tyr Ser Gln Glu Gln Val Asp Val Leu
            20                  25                  30

Val Lys Ala Leu Gly Lys Val Val Tyr Asp Asn Ala Glu Met Phe Ala
        35                  40                  45

Lys Glu Ala Val Glu Glu Thr Glu Met Gly Val Tyr Glu Asp Lys Val
    50                  55                  60

Ala Lys Cys His Leu Lys Ser Gly Ala Ile Trp Asn His Ile Lys Asp
65                  70                  75                  80

Lys Lys Thr Val Gly Ile Ile Lys Glu Glu Pro Glu Arg Ala Leu Val
                85                  90                  95

Tyr Val Ala Lys Pro Lys Gly Val Val Ala Ala Thr Thr Pro Ile Thr
            100                 105                 110

Asn Pro Val Val Thr Pro Met Cys Asn Ala Met Ala Ala Ile Lys Gly
        115                 120                 125

Arg Asn Thr Ile Ile Val Ala Pro His Pro Lys Ala Lys Lys Val Ser
130                 135                 140

Ala His Thr Val Glu Leu Met Asn Ala Glu Leu Lys Lys Leu Gly Ala
145                 150                 155                 160

Pro Glu Asn Ile Ile Gln Ile Val Glu Ala Pro Ser Arg Glu Ala Ala
                165                 170                 175

Lys Glu Leu Met Glu Ser Ala Asp Val Val Ile Ala Thr Gly Gly Ala
            180                 185                 190

Gly Arg Val Lys Ala Ala Tyr Ser Ser Gly Arg Pro Ala Tyr Gly Val
        195                 200                 205

Gly Pro Gly Asn Ser Gln Val Ile Val Asp Lys Gly Tyr Asp Tyr Asn
    210                 215                 220

Lys Ala Ala Gln Asp Ile Ile Thr Gly Arg Lys Tyr Asp Asn Gly Ile
225                 230                 235                 240

Ile Cys Ser Ser Glu Gln Ser Val Ile Ala Pro Ala Glu Asp Tyr Asp
                245                 250                 255

Lys Val Ile Ala Ala Phe Val Glu Asn Gly Ala Phe Tyr Val Glu Asp
            260                 265                 270

Glu Glu Thr Val Glu Lys Phe Arg Ser Thr Leu Phe Lys Asp Gly Lys
        275                 280                 285

Ile Asn Ser Lys Ile Ile Gly Lys Ser Val Gln Ile Ile Ala Asp Leu
    290                 295                 300

Ala Gly Val Lys Val Pro Glu Gly Thr Lys Val Ile Val Leu Lys Gly
305                 310                 315                 320

Lys Gly Ala Gly Glu Lys Asp Val Leu Cys Lys Glu Lys Met Cys Pro
                325                 330                 335

Val Leu Val Ala Leu Lys Tyr Asp Thr Phe Glu Glu Ala Val Glu Ile
            340                 345                 350

Ala Met Ala Asn Tyr Met Tyr Glu Gly Ala Gly His Thr Ala Gly Ile
        355                 360                 365

His Ser Asp Asn Asp Glu Asn Ile Arg Tyr Ala Gly Thr Val Leu Pro
    370                 375                 380

Ile Ser Arg Leu Val Val Asn Gln Pro Ala Thr Thr Ala Gly Gly Ser
385                 390                 395                 400

Phe Asn Asn Gly Phe Asn Pro Thr Thr Thr Leu Gly Cys Gly Ser Trp
                    405                 410                 415

Gly Arg Asn Ser Ile Ser Glu Asn Leu Thr Tyr Glu His Leu Ile Asn
                420                 425                 430

Val Ser Arg Ile Gly Tyr Phe Asn Lys Glu Ala Lys Val Pro Ser Tyr
            435                 440                 445

Glu Glu Ile Trp Gly
        450

<210> SEQ ID NO 5
<211> LENGTH: 870
<212> TYPE: DNA
<213> ORGANISM: Arabidopsis thaliana

<400> SEQUENCE: 5
atggaagtag gttttctggg tctgggcatt atgggtaaag ctatgtccat gaacctgctg      60
aaaaacggtt tcaaagttac cgtgtggaac cgcactctgt ctaaatgtga tgaactggtt     120
gaacacggtg caagcgtgtg cgagtctccg gctgaggtga tcaagaaatg caaatacacg     180
atcgcgatgc tgagcgatcc cgtgtgcagc tctgtctgtt gttttcgataa aggcggtgtt    240 ctggaacaga tctgcgaggg taagggctac atcgacatgt ctaccgtcga cgcggaaact     300
agcctgaaaa ttaacgaagc gatcacgggc aaaggtggcc gttttgtaga aggtcctgtt     360
agcggttcca aaaagccggc agaagacggc agctgatca tcctggcagc aggcgacaaa      420
gcactgttcg aggaatccat cccggccttt gatgtactgg caaacgttc cttttatctg      480 ggtcaggtgg gtaacggtgc gaaaatgaaa ctgattgtta acatgatcat gggttctatg     540
atgaacgcgt ttagcgaagg tctggtactg gcagataaaa gcggtctgtc tagcgacacg     600
ctgctggata ttctggatct gggtgctatg acgaatccga tgttcaaagg caaaggtccg     660
tccatgacta atccagcta cccaccggct ttcccgctga acaccagca gaaagacatg      720 cgtctggctc tggctctggg cgacgaaaac gctgttagca tgccggtcgc tgcggctgcg     780
aacgaagcct tcaagaaagc ccgtagcctg gcctgggcg atctggactt ttctgctgtt     840
atcgaagcgg taaaattctc tcgtgaataa                                     870

<210> SEQ ID NO 6
<211> LENGTH: 289
<212> TYPE: PRT
<213> ORGANISM: Arabidopsis thaliana

<400> SEQUENCE: 6

Met Glu Val Gly Phe Leu Gly Leu Gly Ile Met Gly Lys Ala Met Ser
1               5                   10                  15

Met Asn Leu Leu Lys Asn Gly Phe Lys Val Thr Val Trp Asn Arg Thr
            20                  25                  30

Leu Ser Lys Cys Asp Glu Leu Val Glu His Gly Ala Ser Val Cys Glu
        35                  40                  45

Ser Pro Ala Glu Val Ile Lys Lys Cys Lys Tyr Thr Ile Ala Met Leu
    50                  55                  60

Ser Asp Pro Cys Ala Ala Leu Ser Val Val Phe Asp Lys Gly Val
65                  70                  75                  80

Leu Glu Gln Ile Cys Glu Gly Lys Gly Tyr Ile Asp Met Ser Thr Val
            85                  90                  95

Asp Ala Glu Thr Ser Leu Lys Ile Asn Glu Ala Ile Thr Gly Lys Gly
            100                 105                 110

Gly Arg Phe Val Glu Gly Pro Val Ser Gly Ser Lys Lys Pro Ala Glu
            115                 120                 125

Asp Gly Gln Leu Ile Ile Leu Ala Ala Gly Asp Lys Ala Leu Phe Glu
        130                 135                 140

Glu Ser Ile Pro Ala Phe Asp Val Leu Gly Lys Arg Ser Phe Tyr Leu
145                 150                 155                 160

Gly Gln Val Gly Asn Gly Ala Lys Met Lys Leu Ile Val Asn Met Ile
                165                 170                 175

Met Gly Ser Met Met Asn Ala Phe Ser Glu Gly Leu Val Leu Ala Asp
            180                 185                 190

Lys Ser Gly Leu Ser Ser Asp Thr Leu Leu Asp Ile Leu Asp Leu Gly
        195                 200                 205

Ala Met Thr Asn Pro Met Phe Lys Gly Lys Gly Pro Ser Met Thr Lys
    210                 215                 220

Ser Ser Tyr Pro Pro Ala Phe Pro Leu Lys His Gln Gln Lys Asp Met
225                 230                 235                 240

Arg Leu Ala Leu Ala Leu Gly Asp Glu Asn Ala Val Ser Met Pro Val
                245                 250                 255

Ala Ala Ala Ala Asn Glu Ala Phe Lys Lys Ala Arg Ser Leu Gly Leu
            260                 265                 270

Gly Asp Leu Asp Phe Ser Ala Val Ile Glu Ala Val Lys Phe Ser Arg
        275                 280                 285

Glu

<210> SEQ ID NO 7
<211> LENGTH: 1053
<212> TYPE: DNA
<213> ORGANISM: Aspergillus terreus

<400> SEQUENCE: 7
atgccactgg ttgctcaaaa tccactgcca cgtgctattc tgggtctgat gactttcggt    60
ccgagcgaaa gcaaggtgc gcgtatcact tccctggatg agtttaacaa gtgcctggat   120
tacttccagc agcagggctt ccaggaaatc gataccgcgc gcatctacgt cggcggtgaa   180
caggaggcat tcacggcgca ggcaaagtgg aaagaacgcg gcctgacgct ggcgactaag   240
tggtatccgc agtacccggg tgcgcacaaa ccggatgtcc tgcgtcagaa cctggagctg   300
tccctgaaag aactgggcac gaaccaggtc gatatcttct atctgcacgc gcggatcgt   360 tctgtgccgt cgcggaaaac tctggaaact gttaacgaac tgcacaaaga aggcaaattt   420
gttcagctgg gtctgtctaa ctacaccgct ttcgaagtag ctgaaatcgt gaccctgtgt   480
aacgagcgtg gttgggttcg tccgactatc taccaggcga tgtataacgc tatcacccgt   540
aacatcgaaa ctgaactgat cccggcgtgc aagcgttacg gtattgacat gttatctac   600 aacccactgg cgggtggcct gttcagcggc aaatacaaag cacaggacat cccggctgaa   660
ggtcgttaca cgaccaatc ttccatgggc agatgtacc gcaaccgtta ctttaaggac   720
gcaacctttg acgctctgcg cctgatcgaa ccggttgttg cgaagcacgg cctgacgatg   780
ccggaaaccg cgttccgctg gtccaccac cactccgcac tgaacatgga agatggcggc   840
cgtgacggca tcattctggg tgtaagcagc ctggctcagc tggaaaacaa cctgaaagac   900
attcagaaag gtccgctgcc gcaggaggtt gtagacgtcc tggatcaggc ttggctggtg   960
gctaagccga cggctccaaa ctactggcat ctggacctga atacacgta cgacacccag  1020 gaagctctgt tcaaaccgaa atctaaggcg taa                              1053

<210> SEQ ID NO 8
<211> LENGTH: 357
<212> TYPE: PRT
<213> ORGANISM: Aspergillus terreus

<400> SEQUENCE: 8

```
Met Pro Leu Val Ala Gln Asn Pro Leu Pro Arg Ala Ile Leu Gly Leu
 1               5                  10                  15

Met Thr Phe Gly Pro Ser Glu Ser Lys Gly Ala Arg Ile Thr Ser Leu
            20                  25                  30

Asp Glu Phe Asn Lys Cys Leu Asp Tyr Phe Gln Gln Gly Phe Gln
        35                  40                  45

Glu Ile Asp Thr Ala Arg Ile Tyr Val Gly Gly Gln Glu Ala Phe
    50                  55                  60

Thr Ala Gln Ala Lys Trp Lys Glu Arg Gly Leu Thr Leu Ala Thr Lys
65                  70                  75                  80

Trp Tyr Pro Gln Tyr Pro Gly Ala His Lys Pro Asp Val Leu Arg Gln
                85                  90                  95

Asn Leu Glu Leu Ser Leu Lys Glu Leu Gly Thr Asn Gln Val Asp Ile
            100                 105                 110

Phe Tyr Leu His Ala Ala Asp Arg Ser Val Pro Phe Ala Glu Thr Leu
        115                 120                 125

Glu Thr Val Asn Glu Leu His Lys Gly Lys Phe Val Gln Leu Gly
    130                 135                 140

Leu Ser Asn Tyr Thr Ala Phe Glu Val Ala Glu Ile Val Thr Leu Cys
145                 150                 155                 160

Asn Glu Arg Gly Trp Val Arg Pro Thr Ile Tyr Gln Ala Met Tyr Asn
                165                 170                 175

Ala Ile Thr Arg Asn Ile Glu Thr Glu Leu Ile Pro Ala Cys Lys Arg
            180                 185                 190

Tyr Gly Ile Asp Ile Val Ile Tyr Asn Pro Leu Ala Gly Gly Leu Phe
        195                 200                 205

Ser Gly Lys Tyr Lys Ala Gln Asp Ile Pro Ala Glu Gly Arg Tyr Ser
    210                 215                 220

Asp Gln Ser Ser Met Gly Gln Met Tyr Arg Asn Arg Tyr Phe Lys Asp
225                 230                 235                 240

Ala Thr Phe Asp Ala Leu Arg Leu Ile Glu Pro Val Ala Lys His
                245                 250                 255

Gly Leu Thr Met Pro Glu Thr Ala Phe Arg Trp Val His His Ser
            260                 265                 270

Ala Leu Asn Met Glu Asp Gly Gly Arg Asp Gly Ile Ile Leu Gly Val
        275                 280                 285

Ser Ser Leu Ala Gln Leu Glu Asn Asn Leu Lys Asp Ile Gln Lys Gly
    290                 295                 300

Pro Leu Pro Gln Glu Val Val Asp Val Leu Asp Gln Ala Trp Leu Val
305                 310                 315                 320

Ala Lys Pro Thr Ala Pro Asn Tyr Trp His Leu Asp Leu Lys Tyr Thr
                325                 330                 335

Tyr Asp Thr Gln Glu Ala Leu Phe Lys Pro Lys Ser Lys Ala Ala Val
            340                 345                 350

Lys Phe Ser Arg Glu
        355
```

<210> SEQ ID NO 9

-continued

```
<211> LENGTH: 1104
<212> TYPE: DNA
<213> ORGANISM: Mus musculus

<400> SEQUENCE: 9
atgctgcgtg ctgcttctcg tgctgttggt cgtgctgctg tacgttccgc tcaacgttct      60
ggtactagcg ttggccgtcc gctggcgatg tcccgtccac cgccgcctcg cgcagctagc     120
ggtgccccgc tgcgtccggc aaccgtactg ggcactatgg agatgggtcg tcgcatggac     180
gcttctgcat ccgcggcaag cgttcgtgcg ttcctggaac gtggccatag cgaactggat     240
accgctttca tgtattgcga cggtcagtcc gaaaatatcc tgggtggcct gggcctgggt     300
ctgggctccg gtgattgtac cgttaaaatt gcgaccaagg cgaacccttg ggagggcaag     360
agcctgaagc cggattctgt gcgttctcag ctggagactt ctctgaaacg tctgcagtgt     420
ccgcgcgtag acctgttcta tctgcatgcg ccggaccaca gcactccggt agaggaaact     480
ctgcgtgcgt gtcatcagct gcaccaggaa ggcaagttcg tcgaactggg tctgtctaac     540
tacgcatctt gggaagtggc agaaatctgt acgctgtgta agtctaatgg ttggatcctg     600
ccaaccgtgt accagggcat gtacaacgct accacccgcc aggtagaagc agaactgctg     660
ccgtgcctgc gtcacttcgg cctgcgcttt tacgcttaca cccgctggc gggtggtctg     720
ctgacgggca atacaagta tgaagataaa gatggtaaac aaccggtcgg tcgtttcttt     780
ggtaacaact gggccgaaac ctaccgtaat cgcttctgga agagcacca ctttgaagcg     840
atcgcactgg ttgaaaaagc gctgcagacg acttatggca ctaacgcgcc gcgtatgacc     900
tccgctcgc tgcgttggat gtaccaccat agccagctgc agggtactcg cggcgatgcc     960
gttatcctgg gcatgagctc cctggaacag ctggaacaga acctggccgc gactgaagag    1020
ggcccgctgg aaccggcagt tgtcgaagct tttgaccagg catggaacat ggtggcgcac    1080
gaatgtccaa actatttccg ctaa                                           1104

<210> SEQ ID NO 10
<211> LENGTH: 367
<212> TYPE: PRT
<213> ORGANISM: Mus musculus

<400> SEQUENCE: 10

Met Leu Arg Ala Ala Ser Arg Ala Val Gly Arg Ala Ala Val Arg Ser
 1               5                  10                  15

Ala Gln Arg Ser Gly Thr Ser Val Gly Arg Pro Leu Ala Met Ser Arg
            20                  25                  30

Pro Pro Pro Arg Ala Ala Ser Gly Ala Pro Leu Arg Pro Ala Thr
        35                  40                  45

Val Leu Gly Thr Met Glu Met Gly Arg Arg Met Asp Ala Ser Ala Ser
    50                  55                  60

Ala Ala Ser Val Arg Ala Phe Leu Glu Arg Gly His Ser Glu Leu Asp
65                  70                  75                  80

Thr Ala Phe Met Tyr Cys Asp Gly Gln Ser Glu Asn Ile Leu Gly Gly
                85                  90                  95

Leu Gly Leu Gly Leu Gly Ser Gly Asp Cys Thr Val Lys Ile Ala Thr
            100                 105                 110

Lys Ala Asn Pro Trp Glu Gly Lys Ser Leu Lys Pro Asp Ser Val Arg
        115                 120                 125

Ser Gln Leu Glu Thr Ser Leu Lys Arg Leu Gln Cys Pro Arg Val Asp
    130                 135                 140
```

Leu Phe Tyr Leu His Ala Pro Asp His Ser Thr Pro Val Glu Glu Thr
145                 150                 155                 160

Leu Arg Ala Cys His Gln Leu His Gln Glu Gly Lys Phe Val Glu Leu
            165                 170                 175

Gly Leu Ser Asn Tyr Ala Ser Trp Glu Val Ala Glu Ile Cys Thr Leu
        180                 185                 190

Cys Lys Ser Asn Gly Trp Ile Leu Pro Thr Val Tyr Gln Gly Met Tyr
    195                 200                 205

Asn Ala Thr Thr Arg Gln Val Glu Ala Glu Leu Leu Pro Cys Leu Arg
210                 215                 220

His Phe Gly Leu Arg Phe Tyr Ala Tyr Asn Pro Leu Ala Gly Gly Leu
225                 230                 235                 240

Leu Thr Gly Lys Tyr Lys Tyr Glu Asp Lys Asp Gly Lys Gln Pro Val
            245                 250                 255

Gly Arg Phe Phe Gly Asn Asn Trp Ala Glu Thr Tyr Arg Asn Arg Phe
        260                 265                 270

Trp Lys Glu His His Phe Glu Ala Ile Ala Leu Val Glu Lys Ala Leu
    275                 280                 285

Gln Thr Thr Tyr Gly Thr Asn Ala Pro Arg Met Thr Ser Ala Ala Leu
290                 295                 300

Arg Trp Met Tyr His His Ser Gln Leu Gln Gly Thr Arg Gly Asp Ala
305                 310                 315                 320

Val Ile Leu Gly Met Ser Ser Leu Glu Gln Leu Glu Gln Asn Leu Ala
            325                 330                 335

Ala Thr Glu Glu Gly Pro Leu Gly Pro Ala Val Val Ala Phe Asp
        340                 345                 350

Gln Ala Trp Asn Met Val Ala His Glu Cys Pro Asn Tyr Phe Arg
    355                 360                 365

<210> SEQ ID NO 11
<211> LENGTH: 1821
<212> TYPE: DNA
<213> ORGANISM: Artificial Sequence
<220> FEATURE:
<223> OTHER INFORMATION: Pseudomonas putida/Ralstonia eutropha

<400> SEQUENCE: 11
atgactagaa ggaggtttca tatgagtaac aagaacaacg atgagctggc gacgggtaaa      60
ggtgctgctg catcttctac tgaaggtaaa tctcagccgt ttaaattccc accgggtccg     120
ctggacccgg ccacttggct ggaatggagc cgtcagtggc aaggtccgga gggcaatggc     180
ggtaccgtgc cgggtggctt ccgggtttc gaagcgttcg cggcgtcccc gctggcgggc     240
gtgaaaatcg acccggctca gctggcagag atccagcagc gttatatgcg tgatttcacc     300
gagctgtggc gtggtctggc aggcggtgac accgagagcg ctggcaaact gcatgaccgt     360
cgcttcgcgt ccgaagcgtg gcacaaaaac gcgccgtatc gctatactgc ggcattttac     420
ctgctgaacg cacgtgcact gacggaactg gctgatgcag tagaagcgga tccgaaaacc     480
cgtcagcgta tccgttttgc ggtttcccag tgggtagatg ctatgagccc ggctaacttc     540
ctggccacca acccggacgc tcagaaccgt ctgatcgaga gccgtggtga agcctgcgt      600 gccggcatgc gcaatatgct ggaagatctg acccgcggta aatttccca aaccgatgag     660 actgccttcg aagtaggccg taacatggca gttaccgaag gtgctgtggt attcgaaaac     720
gagttcttcc agctgctgca gtacaaacct ctgactgaca agtatacac ccgtccgctg      780 ctgctggtac cgccgtgcat taacaagttc tatattctgg acctgcagcc ggaaggttct     840

```
ctggtccgtt acgcagtcga acagggtcac actgtattcc tggtgagctg gcgcaatcca        900
gacgctagca tggctggctg tacctgggat gactatattg aaaacgcggc tatccgcgcc        960
atcgaggttg tgcgtgatat cagcggtcag gacaagatca acaccctggg cttttgtgtt       1020
ggtggcacga tcatctccac tgccctggcg gtcctggccg cccgtggtga gcacccggtg       1080
gcctctctga ccctgctgac taccctgctg gacttcaccg atactggtat cctggatgtt       1140
ttcgtggacg agccacacgt tcagctgcgt gaggcgactc tgggcggcgc cagcggcggt       1200
ctgctgcgtg gtgtcgagct ggccaatacc ttttccttcc tgcgcccgaa cgacctggtt       1260
tggaactacg ttgttgacaa ctatctgaaa ggcaacaccc cggtacccttt cgatctgctg       1320
ttctggaacg gtgatgcaac caacctgcct ggtccatggt actgttggta cctgcgtcat       1380
acttacctgc agaacgaact gaaagagccg ggcaaactga ccgtgtgtaa cgaacctgtg       1440
gacctgggcg cgattaacgt tcctacttac atctacggtt cccgtgaaga tcacatcgta       1500
ccgtggaccg cggcttacgc cagcaccgcg ctgctgaaga cgatctgcg tttcgtactg        1560
ggcgcatccg gccatatcgc aggtgtgatc aaccctcctg caaagaaaaa gcgttctcat       1620
tggaccaacg acgcgctgcc agaatccgcg caggattggc tggcaggtgc tgaggaacac       1680
catggttcct ggtggccgga ttggatgacc tggctgggta acaagccgg tgcaaaacgt        1740
gcagctccaa ctgaatatgg tagcaagcgt tatgctgcaa tcgagccagc gccaggccgt       1800
tacgttaaag cgaaagcata a                                                 1821
```

<210> SEQ ID NO 12
<211> LENGTH: 599
<212> TYPE: PRT
<213> ORGANISM: Artificial Sequence
<220> FEATURE:
<223> OTHER INFORMATION: Pseudomonas putida/Ralstonia eutropha

<400> SEQUENCE: 12

```
Met Ser Asn Lys Asn Asn Asp Glu Leu Ala Thr Gly Lys Gly Ala Ala
 1               5                  10                  15

Ala Ser Ser Thr Glu Gly Lys Ser Gln Pro Phe Lys Phe Pro Pro Gly
                20                  25                  30

Pro Leu Asp Pro Ala Thr Trp Leu Glu Trp Ser Arg Gln Trp Gln Gly
            35                  40                  45

Pro Glu Gly Asn Gly Gly Thr Val Pro Gly Gly Phe Pro Gly Phe Glu
        50                  55                  60

Ala Phe Ala Ala Ser Pro Leu Ala Gly Val Lys Ile Asp Pro Ala Gln
65                  70                  75                  80

Leu Ala Glu Ile Gln Gln Arg Tyr Met Arg Asp Phe Thr Glu Leu Trp
                85                  90                  95

Arg Gly Leu Ala Gly Gly Asp Thr Glu Ser Ala Gly Lys Leu His Asp
            100                 105                 110

Arg Arg Phe Ala Ser Glu Ala Trp His Lys Asn Ala Pro Tyr Arg Tyr
        115                 120                 125

Thr Ala Ala Phe Tyr Leu Leu Asn Ala Arg Ala Leu Thr Glu Leu Ala
    130                 135                 140

Asp Ala Val Glu Ala Asp Pro Lys Thr Arg Gln Arg Ile Arg Phe Ala
145                 150                 155                 160

Val Ser Gln Trp Val Asp Ala Met Ser Pro Ala Asn Phe Leu Ala Thr
                165                 170                 175
```

```
Asn Pro Asp Ala Gln Asn Arg Leu Ile Glu Ser Arg Gly Glu Ser Leu
            180                 185                 190

Arg Ala Gly Met Arg Asn Met Leu Glu Asp Leu Thr Arg Gly Lys Ile
        195                 200                 205

Ser Gln Thr Asp Glu Thr Ala Phe Glu Val Gly Arg Asn Met Ala Val
        210                 215                 220

Thr Glu Gly Ala Val Val Phe Glu Asn Glu Phe Gln Leu Leu Gln
225                 230                 235                 240

Tyr Lys Pro Leu Thr Asp Lys Val Tyr Thr Arg Pro Leu Leu Val
                245                 250                 255

Pro Pro Cys Ile Asn Lys Phe Tyr Ile Leu Asp Leu Gln Pro Glu Gly
            260                 265                 270

Ser Leu Val Arg Tyr Ala Val Glu Gln Gly His Thr Val Phe Leu Val
        275                 280                 285

Ser Trp Arg Asn Pro Asp Ala Ser Met Ala Gly Cys Thr Trp Asp Asp
        290                 295                 300

Tyr Ile Glu Asn Ala Ala Ile Arg Ala Ile Glu Val Val Arg Asp Ile
305                 310                 315                 320

Ser Gly Gln Asp Lys Ile Asn Thr Leu Gly Phe Cys Val Gly Gly Thr
                325                 330                 335

Ile Ile Ser Thr Ala Leu Ala Val Leu Ala Ala Arg Gly Glu His Pro
            340                 345                 350

Val Ala Ser Leu Thr Leu Leu Thr Thr Leu Leu Asp Phe Thr Asp Thr
        355                 360                 365

Gly Ile Leu Asp Val Phe Val Asp Glu Pro His Val Gln Leu Arg Glu
        370                 375                 380

Ala Thr Leu Gly Gly Ala Ser Gly Gly Leu Leu Arg Gly Val Glu Leu
385                 390                 395                 400

Ala Asn Thr Phe Ser Phe Leu Arg Pro Asn Asp Leu Val Trp Asn Tyr
                405                 410                 415

Val Val Asp Asn Tyr Leu Lys Gly Asn Thr Pro Val Pro Phe Asp Leu
            420                 425                 430

Leu Phe Trp Asn Gly Asp Ala Thr Asn Leu Pro Gly Pro Trp Tyr Cys
        435                 440                 445

Trp Tyr Leu Arg His Thr Tyr Leu Gln Asn Glu Leu Lys Glu Pro Gly
        450                 455                 460

Lys Leu Thr Val Cys Asn Glu Pro Val Asp Leu Gly Ala Ile Asn Val
465                 470                 475                 480

Pro Thr Tyr Ile Tyr Gly Ser Arg Glu Asp His Ile Val Pro Trp Thr
                485                 490                 495

Ala Ala Tyr Ala Ser Thr Ala Leu Leu Lys Asn Asp Leu Arg Phe Val
            500                 505                 510

Leu Gly Ala Ser Gly His Ile Ala Gly Val Ile Asn Pro Pro Ala Lys
        515                 520                 525

Lys Lys Arg Ser His Trp Thr Asn Asp Ala Leu Pro Glu Ser Ala Gln
        530                 535                 540

Asp Trp Leu Ala Gly Ala Glu Glu His His Gly Ser Trp Trp Pro Asp
545                 550                 555                 560

Trp Met Thr Trp Leu Gly Lys Gln Ala Gly Ala Lys Arg Ala Ala Pro
                565                 570                 575
```

```
Thr Glu Tyr Gly Ser Lys Arg Tyr Ala Ala Ile Glu Pro Ala Pro Gly
            580                 585                 590

Arg Tyr Val Lys Ala Lys Ala
            595
```

PROCESS FOR GAMMA-BUTYROLACTONE PRODUCTION

RELATED APPLICATIONS

This application is the U.S. National Stage of International Application No. PCT/US2011/024612, filed Feb. 11, 2011, which designates the U.S., published in English, and claims the benefit of U.S. Provisional Application No. 61/303,584, filed Feb. 11, 2010, U.S. Provisional Application No. 61/382,855, filed Sep. 14, 2010, and also U.S. Provisional Application No. 61/413,195, filed Nov. 12, 2010. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
   a) File name: 46141001001Sequence.txt; created Aug. 1, 2012, 36.57 KB in size.

BACKGROUND OF THE INVENTION

With dwindling petroleum resources, increasing energy prices, and environmental concerns, development of energy efficient biorefinery processes to produce biobased chemicals from renewable, low cost, carbon resources offers a unique solution to overcoming the increasing limitations of petroleum-based chemicals.

One chemical with wide industrial and pharmaceutical uses that could be manufactured using a biorefinery process is gamma-butyrolactone (GBL). The global market demand for GBL has been estimated at 850 million lbs/yr, translating to total sales of $1 billion annually. Gamma-buytrolactone is a colorless, weak odor liquid that is used predominantly as an intermediate in the manufacture of commercially important chemicals such as 1,4-butanediol (BDO), tetrahydrofuran (THF), N-methylpyrrolidone (NMP), N-ethylpyrrolidone (NEP), 2-pyrrolidinone, N-vinylpyrrolidone (NVP), polyvinylpyrrolidone (PVP) and so forth. These chemicals have applications in high performance solvents for electronics, lube oil extraction, magnetic wire coatings, engineering resins, pharmaceutical intermediates, cosmetics, hair spray and high valued polymers. GBL by itself has many uses including as a solvent for paint stripping, degreaser, viscosity modifier for polyurethanes, dispersant for water soluble inks, curing agent for urethanes and polyamides, etchant for metal coated plastics, rubber additive and herbicide ingredient.

Petroleum-based GBL is manufactured by several different chemical processes. For example, it is synthesized by dehydration of gamma-hydroxybutyric acid (GHB), by the reaction of acetylene with formaldehyde or vapor phase hydrogenation of maleic anhydride or succinic anhydride and their esters. The latter two methods are respectively known as the Reppe process and the Davy process. The Reppe process was developed in the 1940's and historically was the first commercial route to making 1,4-butanediol. The process starts by reacting acetylene and formaldehyde together which is then followed by a series of hydrogenation stages to obtain BDO and finally dehydrogenation to generate GBL. The main disadvantages of this process are that the starting reactants are quite hazardous and generally present the manufacturer with handling and environmental challenges. Additionally, acetylene is a relatively expensive starting material.

The Davy Process, developed in the 1990's, uses a multi-stage process that starts by reacting molten maleic anhydride with methanol to produce monomethyl maleate. Next the monomethyl maleate is converted from mono to dimethyl maleate in the presence of an acid resin catalyst. Using catalytic vapor phase hydrogenation, the dimethyl maleate is converted to dimethyl succinate and then finally through a series of additional reactions to a GBL. The final product is refined to obtain the high purity GBL. Many patents describe the various types of hydrogenation catalysts used to convert maleic anhydride or succinic anhydride to GBL. These include copper chromite (described in U.S. Pat. No. 3,065,243), copper chromite with nickel (U.S. Pat. No. 4,006,165), and mixtures of copper, zinc or aluminum oxides (U.S. Pat. No. 5,347,021) as well as reduced copper and aluminum oxides mixtures (U.S. Pat. No. 6,075,153).

Even with the large number of available hydrogenation catalysts for GBL production, there are deficiencies in catalyst performance which need to be overcome such as yield, selectivity, ease of product recovery and cost.

A need therefore exists to develop new GBL manufacturing processes that address not only improvements in the yield, purity, and cost of the product but also use sustainable starting materials that have a more positive impact on the environment.

SUMMARY OF THE INVENTION

The invention generally relates to integrated biorefinery processes for producing high purity, high yield, biobased, gamma-butyrolactone (GBL) product from renewable carbon resources. In one aspect, a process for the production of gamma-butyrolactone (GBL) product from a genetically engineered microbial biomass metabolizing glucose or any other renewable feedstock to produce 4-hydroxybutyrate homopolymer (P4HB) inside the microbial cells, followed by controlled heating of the biomass containing P4HB with a catalyst forming the gamma-butyrolactone (GBL) product is described. The level of P4HB in the biomass should be greater than 10% by weight of the total biomass. The advantages of this bioprocess are that it uses a renewable carbon source as the feedstock material, the genetically engineered microbe produces P4HB in very high yield without adverse toxicity effects to the host cell (which could limit process efficiency) and when combined with a catalyst and heated is capable of producing biobased GBL in high yield with high purity.

In certain aspects, a recombinant engineered P4HB biomass from a host organism serves as a renewable source for converting 4-hydroxybutyrate homopolymer to the useful intermediate GBL. In some embodiments, a source of the renewable feedstock is selected from glucose, fructose, sucrose, arabinose, maltose, lactose, xylose, fatty acids, vegetable oils, and biomass derived synthesis gas or a combination of two or more of these. The produced P4HB biomass is then treated in the presence of a catalyst to produce gamma-butyrolactone (GBL). In other embodiments, the P4HB biomass is dried prior to combining with the catalyst. In certain embodiment, the process further comprises recovering the gamma-butyrolactone product. In certain embodiments, the recovery is by condensation.

In some embodiments the GBL is further processed for production of other desired commodity and specialty products, for example 1,4-butanediol (BDO), tetrahydrofuran (THF), N-methylpyrrolidone (NMP), N-ethylpyrrolidone (NEP), 2-pyrrolidinone, N-vinylpyrrolidone (NVP), polyvinylpyrrolidone (PVP) and the like.

The host organism used to produce the biomass containing P4HB has been genetically modified by introduction of genes and/or deletion of genes in a wild-type or genetically engineered P4HB production organism creating strains that synthesize P4HB from inexpensive renewable feedstocks. An exemplary pathway for production of P4HB is provided in FIG. 1 and it is understood that additional enzymatic changes that contribute to this pathway can also be introduced or suppressed for a desired production of P4HB.

In one aspect, the present invention provides a process for production of biobased gamma-butyrolactone product. In certain embodiments, gamma-butyrolactone in the product has 100% biobased carbon content (e.g, as determined based on $^{14}C$ isotope analysis). The process includes combining a genetically engineered biomass comprising poly-4-hydroxybutyrate and a catalyst; heating the biomass with the catalyst to convert 4-hydroxybutyrate to gamma-butyrolactone product. In certain embodiments, a yield of gamma-butyrolactone product is about 85% by weight or greater based on one gram of a gamma-butyrolactone in the product per gram of the poly-4-hydroxybutyrate. The genetically engineered recombinant host produces a 4-hydroxybutyrate polymer.

In another aspect, the genetically engineered biomass for use in the processes of the invention is from a recombinant host having a poly-4-hydroxybutyrate pathway, wherein the host has an inhibiting mutation in its CoA-independent NAD-dependent succinic semialdehyde dehydrogenase gene or its CoA-independent NADP-dependent succinic semialdehyde dehydrogenase gene, or having inhibiting mutations in both genes, and having stably incorporated one or more genes encoding one or more enzymes selected from a succinyl-CoA:coenzyme A transferase wherein the succinyl-CoA:coenzyme A transferase is able to convert succinate to succinyl-CoA, a succinate semialdehyde dehydrogenase wherein the succinate semialdehyde dehydrogenase is able to convert succinyl-CoA to succinic semialdehyde, a succinic semialdehyde reductase wherein the succinic semialdehyde reductase is able to convert succinic semialdehyde to 4-hydroxybutyrate, a CoA transferase wherein the CoA transferase is able to convert 4-hydroxybutyrate to 4-hydroxybutyryl-CoA, and a polyhydroxyalkanoate synthase wherein the polyhydroxyalkanoate synthase is able to polymerize 4-hydroxybutyryl-CoA to poly-4-hydroxybutyrate. In a further aspect, the host has two or more, three or more, four or more or all five of the stably incorporating genes encoding the enzymes listed above.

In yet another aspect of the invention, the genetically engineered biomass for use in the processes of the invention is from a recombinant host having stably incorporated one or more genes encoding one or more enzymes selected from: a phosphoenolpyruvate carboxylase wherein the phosphoenolpyruvate carboxylase is able to convert phosphoenolpyruvate to oxaloacetate, an isocitrate lyase wherein the isocitrate lyase is able to convert isocitrate to glyoxalate, a malate synthase wherein the malate synthase is able to convert glyoxalate to malate and succinate, a succinate-CoA ligase (ADP-forming) wherein the succinate-CoA ligase (ADP-forming) is able to convert succinate to succinyl-CoA, an NADP-dependent glyceraldeyde-3-phosphate dehydrogenase wherein the NADP-dependent glyceraldeyde-3-phosphate dehydrogenase is able to convert glyceraldehyde 3-phosphate to 1,3-bisphosphoglycerate forming NADPH+H$^+$, an NAD-dependent glyceraldeyde-3-phosphate dehydrogenase wherein the NAD-dependent glyceraldeyde-3-phosphate dehydrogenase is able to convert glyceraldehyde 3-phosphate to 1,3-bisphosphoglycerate forming NADH+H$^+$, a butyrate kinase wherein the butyrate kinase is able to convert 4-hydroxybutyrate to 4-hydroxybutyryl-phosphate, a phosphotransbutyrylase wherein the phosphotransbutyrylase is able to convert 4-hydroxybutyryl-phosphate to 4-hydroxybutyryl-CoA; and optionally having a disruption in one or more genes selected from yneI, gabD, pykF, pykA, maeA and maeB.

In a further aspect, the genetically engineered biomass for use in the processes of the invention is from a recombinant host having a poly-4-hydroxybutyrate pathway and stably expressing two or more genes encoding two or more enzymes, three or more genes encoding three or more enzymes, four of more genes encoding four or more enzymes or five or more genes encoding five or more enzymes selected from: a phosphoenolpyruvate carboxylase wherein the phosphoenolpyruvate carboxylase is able to convert phosphoenol pyruvate to oxaloacetate, a isocitrate lyase wherein the isocitrate lyase is able to convert isocitrate to glyoxalate, a malate synthase wherein the malate synthase is able to convert glyoxalate to malate and succinate, an NADP-dependent glyceraldeyde-3-phosphate dehydrogenase wherein the NADP-dependent glyceraldeyde-3-phosphate dehydrogenase is able to convert glyceraldehyde 3-phosphate to 1,3 bisphosphoglycerate forming NADPH+H, an NAD-dependent glyceraldcyde-3-phosphate dehydrogenase wherein the NAD-dependent glyceraldeyde-3-phosphate dehydrogenase is able to convert glyceraldehyde 3-phosphate to 1,3 bisphosphoglycerate forming NADH+H; and optionally having a disruption in one or more genes, two or more genes, three or more genes, four or more genes, five or more gene, or six genes selected from yneI, gabD, pykF, pykA, maeA and maeB.

In another embodiment, the genetically engineered biomass for use in the processes of the invention is from a recombinant host having a poly-4-hydroxybutyrate pathway, wherein the host has an inhibiting mutation in its CoA-independent NAD-dependent succinic semialdehyde dehydrogenase gene or its CoA-independent NADP-dependent succinic semialdehyde dehydrogenase gene, or having inhibiting mutations in both genes, and having stably incorporated genes encoding the following enzymes: a succinyl-CoA:coenzyme A transferase wherein the succinyl-CoA:coenzyme A transferase is able to convert succinate to succinyl-CoA, a succinate semialdehyde dehydrogenase wherein the succinate semialdehyde dehydrogenase is able to convert succinyl-CoA to succinic semialdehyde, a succinic semialdehyde reductase wherein the succinic semialdehyde reductase is able to convert succinic semialdehyde to 4-hydroxybutyrate, a CoA transferase wherein the CoA transferase is able to convert 4-hydroxybutyrate to 4-hydroxybutyryl-CoA, and a polyhydroxyalkanoate synthase wherein the polyhydroxyalkanoate synthase is able to polymerize 4-hydroxybutyryl-CoA to poly-4-hydroxybutyrate.

In yet another embodiment, the genetically engineered biomass for use in the processes of the invention is from a recombinant host having stably incorporated genes encoding the following enzymes: a phosphoenolpyruvate carboxylase wherein the phosphoenolpyruvate carboxylase is able to convert phosphoenolpyruvate to oxaloacetate, an isocitrate lyase wherein the isocitrate lyase is able to convert isocitrate to glyoxalate, a malate synthase wherein the malate synthase is able to convert glyoxalate to malate and succinate, a succinate-CoA ligase (ADP-forming) wherein the succinate-CoA ligase (ADP-forming) is able to convert succinate to succinyl-CoA, an NADP-dependent glyceraldeyde-3-phosphate dehydrogenase wherein the NADP-dependent glyceraldeyde-3-phosphate dehydrogenase is able to convert glyceraldehyde 3-phosphate to 1,3-bisphosphoglycerate forming NADPH+H$^+$, an NAD-dependent glyceraldeyde-3-phosphate dehydrogenase wherein the NAD-dependent glyceraldeyde-3-phosphate dehydrogenase is able to convert glyceraldehyde 3-phosphate to 1,3-bisphosphoglycerate forming NADH+H$^+$, a butyrate kinase wherein the butyrate kinase is able to convert 4-hydroxybutyrate to 4-hydroxybutyryl-phosphate, a phosphotransbutyrylase wherein the phosphotransbutyrylase is able to convert 4-hydroxybutyryl-phosphate to 4-hydroxybutyryl-CoA; and optionally having a disruption in one or more genes selected from yneI, gabD, pykF, pykA, maeA and maeB.

In certain embodiments, wherein the genetically engineered biomass for use in the processes of the invention is from a recombinant host having a poly-4-hydroxybutyrate pathway, wherein the host has stably incorporated one or more genes encoding one or more enzymes selected from a succinyl-CoA:coenzyme A transferase wherein the succinyl-CoA:coenzyme A transferase is able to convert succinate to succinyl-CoA, a succinate semialdehyde dehydrogenase wherein the succinate semialdehyde dehydrogenase is able to convert succinyl-CoA to succinic semialdehyde, a succinic semialdehyde reductase wherein the succinic semialdehyde reductase is able to convert succinic semialdehyde to 4-hydroxybutyrate, a CoA transferase wherein the CoA transferase is able to convert 4-hydroxybutyrate to 4-hydroxybutyryl-CoA, and a polyhydroxyalkanoate synthase wherein the polyhydroxyalkanoate synthase is able to polymerize 4-hydroxybutyryl-CoA to poly-4-hydroxybutyrate.

In other embodiments, the genetically engineered biomass for use in the processes of the invention is from a recombinant host having stably incorporated one or more genes encoding one or more enzymes selected from: a phosphoenolpyruvate carboxylase wherein the phosphoenolpyruvate carboxylase is able to convert phosphoenolpyruvate to oxaloacetate, an isocitrate lyase wherein the isocitrate lyase is able to convert isocitrate to glyoxalate, a malate synthase wherein the malate synthase is able to convert glyoxalate to malate and succinate, a succinate-CoA ligase (ADP-forming) wherein the succinate-CoA ligase (ADP-forming) is able to convert succinate to succinyl-CoA, an NADP-dependent glyceraldeyde-3-phosphate dehydrogenase wherein the NADP-dependent glyceraldeyde-3-phosphate dehydrogenase is able to convert glyceraldehyde 3-phosphate to 1,3-bisphosphoglycerate forming NADPH+H$^+$, an NAD-dependent glyceraldeyde-3-phosphate dehydrogenase wherein the NAD-dependent glyceraldeyde-3-phosphate dehydrogenase is able to convert glyceraldehyde 3-phosphate to 1,3-bisphosphoglycerate forming NADH+H$^+$, a butyrate kinase wherein the butyrate kinase is able to convert 4-hydroxybutyrate to 4-hydroxybutyryl-phosphate, a phosphotransbutyrylase wherein the phosphotransbutyrylase is able to convert 4-hydroxybutyryl-phosphate to 4-hydroxybutyryl-CoA; and optionally having a disruption in one or more genes selected from yneI, gabD, pykF, pykA, maeA and maeB.

In a certain aspect of the invention, a recombinant host is cultered with a renewable feedstock to produce a 4-hydroxybutyrate biomass, the produced biomass is then treated in the presence of a catalyst to produce gamma-butyrolactone (GBL) product, wherein a yield of gamma-butyrolactone product is about 85% by weight.

In certain embodiments, the source of the renewable feedstock is selected from glucose, fructose, sucrose, arabinose, maltose lactose xylose, fatty acids, vegetable oils, and biomass derived synthesis gas or a combination thereof.

The invention also pertains to a biobased gamma-butyrolactone product produced by the processes described herein. In certain aspects, the amount of gamma-butyrolactone in the product produced is 85% or greater than 85%. In a further aspect, the invention pertains to a poly-4-hydroxybutyrate biomass produced from renewable resources which is suitable as a feedstock for producing gamma-butyrolactone product, wherein the level of poly-4-hydroxybutyrate in the biomass is greater than 50% by weight of the biomass.

In certain embodiments of the invention, the biomass host is bacteria, yeast, fungi, algae, cyanobacteria, or a mixture of any two or more thereof. The bacteria includes but is not limited to *Escherichia coli, Alcaligenes eutrophus* (renamed as *Ralstonia eutropha*), *Bacillus* spp., *Alcaligenes latus, Azotobacter, Aeromonas, Comamonas, Pseudomonads), Pseudomonas, Ralstonia, Klebsiella), Synechococcus* sp PCC7002, *Synechococcus* sp. PCC 7942, *Synechocystis* sp. PCC 6803, and *Thermosynechococcus elongatus* BP-I (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus*, and *Rhodopseudomonas palustris*. In other embodiments, the recombinant host is algae. The algae include but are not limited to *Chlorella minutissima, Chlorella emersonii, Chlorella sorokiniana, Chlorella ellipsoidea, Chlorella* sp., or *Chlorella protothecoides*.

In certain embodiments of the invention, the heating is at a temperature of about 100° C. to about 350° C. or about 200° C. to about 350° C., or from about 225° C. to 300° C. In some embodiments, the heating reduces the water content of the biomass to about 5 wt %, or less. In the embodiments described, the heating is for a time period from about 30 seconds to about 5 minutes or is from about 5 minutes to about 2 hours. In certain embodiments the gamma-butyrolactone comprises less than 5% of undesired side products. In certain embodiments, the catalyst is sodium carbonate or calcium hydroxide. The weight percent of catalyst is in the range of about 4% to about 50%. In particular embodiments, the weight % of the catalyst is in the range of about 4% to about 50%, and the heating is at about 300° C. In certain embodiments, the gamma-butyrolactone product is further recovered. In some embodiments, the catalyst is 4% by weight calcium hydroxide and the heating is at a temperature of 300° C.

Additionally, the expended (residual) PHA reduced biomass is further utilized for energy development, for example as a fuel to generate process steam and/or heat.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

"P4HB", poly-4-hydroxybutyrate. Numbered reactions: "1", glyceraldehyde-3-phosphate dehydrogenase; "2", pyruvate kinase; "3", phosphoenolpyruvate carboxylase; "4", malic enzyme; "5", isocitrate lyase; "6", malate dehydrogenase; "7", succinate semialdehyde dehydrogenase; "8", alpha-ketoglutarate decarboxylase; "9", succinic semialdehyde reductase; "10", CoA transferase; "11", polyhydroxyalkanoate synthase; "12", succinate-semialdehyde dehydrogenase, NADP+-dependent.

Figure 2:
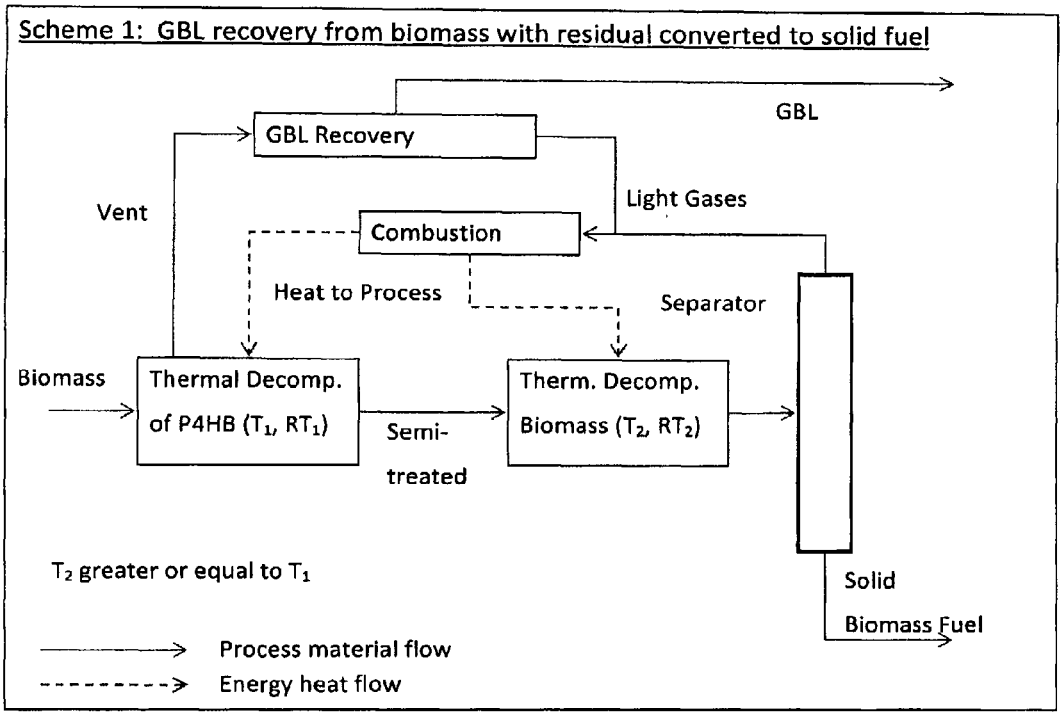

FIG. 2 is a schematic of GBL recovery from biomass with residual converted to solid fuel, according to various embodiments.

Figure 3:
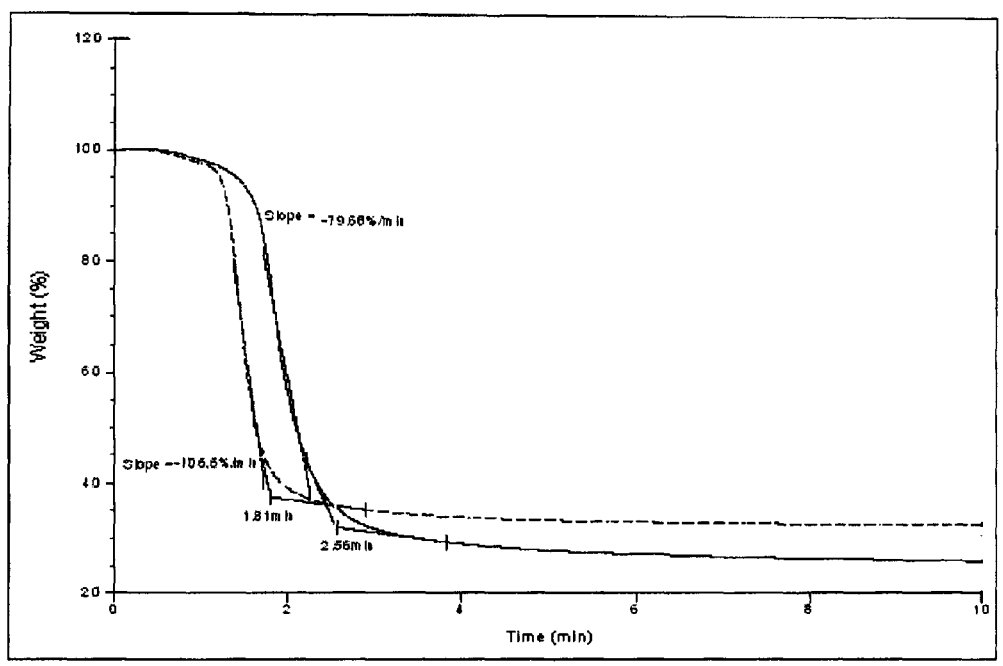

FIG. 3 is a weight loss vs. time curve at 300° C. in $N_2$ for dry P4HB fermentation broth without lime (solid curve) and with 5% lime addition (dashed curve), according to various embodiments. The curves show the weight loss slopes and onset times for completed weight loss.

Figure 4A:
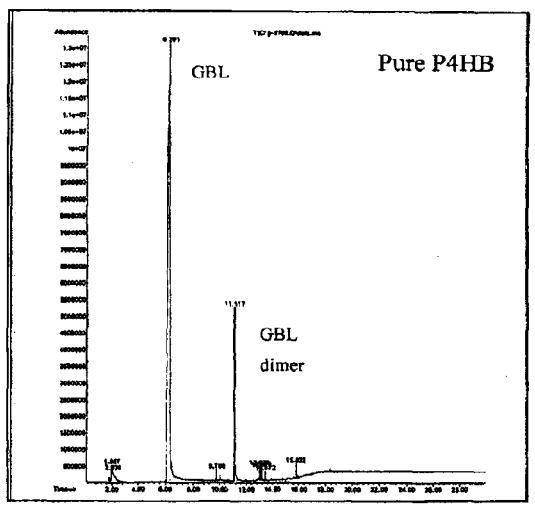
Figure 4B:
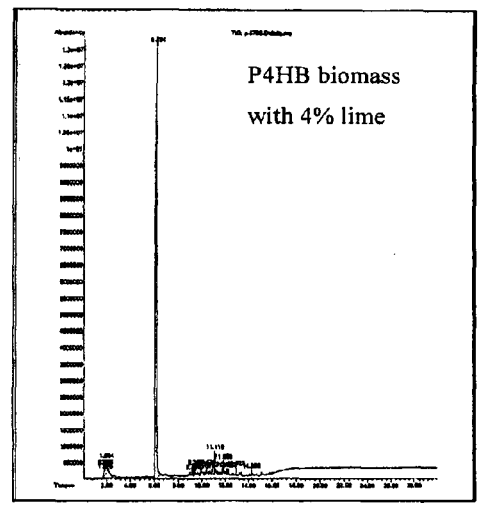
Figure 4C:
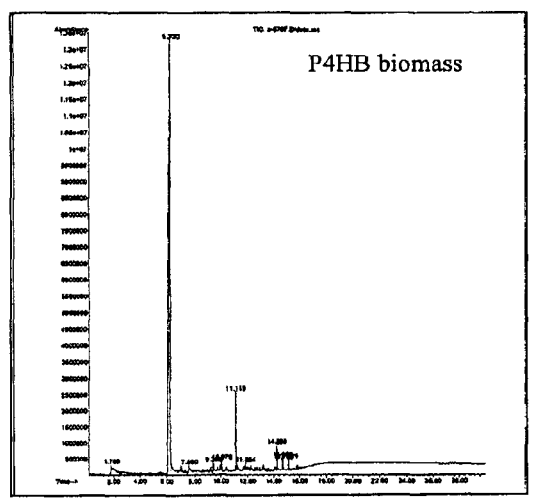

FIG. 4 (A-C) is a series of gas chromatograms of P4HB pure polymer, P4HB dry broth and P4HB dry broth+5% lime $(Ca(OH)_2)$ catalyst after pyrolysis at 300° C., according to one embodiment.

Figure 5:
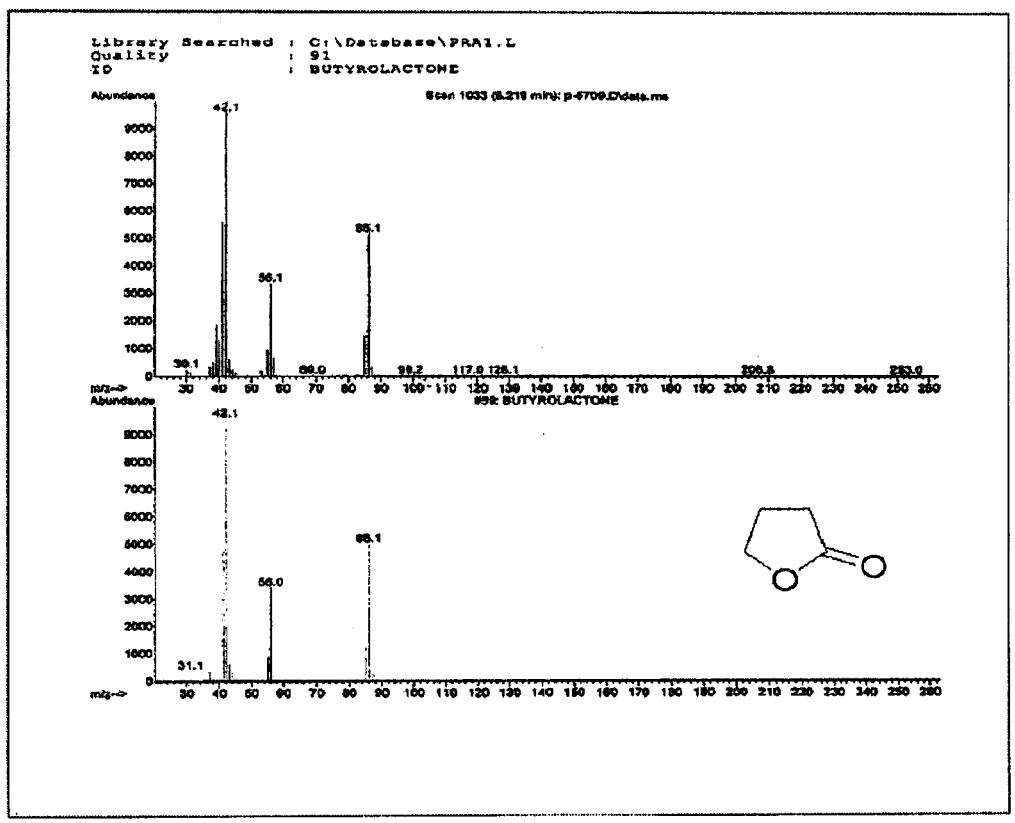

FIG. 5 is a mass spectral library match of GC-MS peak @6.2 min to GBL (gamma-butyrolactone) according to one embodiment.

Figure 6:
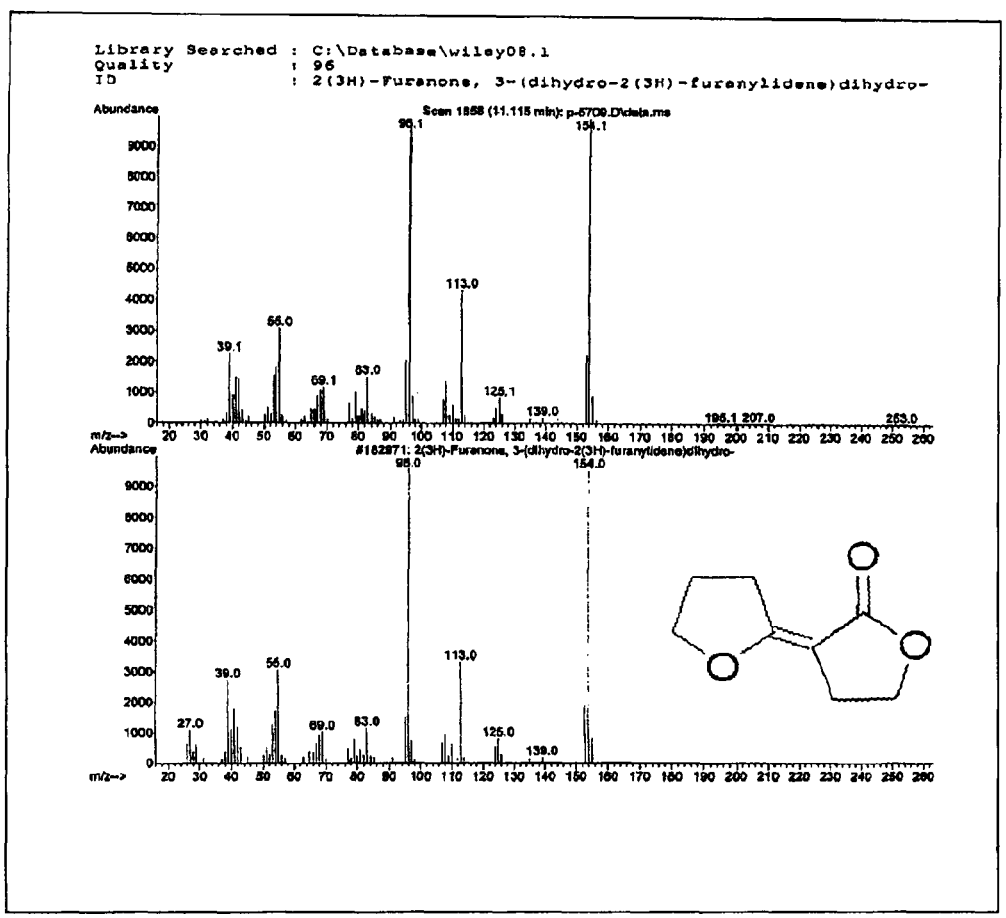

FIG. 6 is a mass spectral library match of GC-MS peak @11.1 min peak for GBL dimer according to one embodiment.

Figure 7:
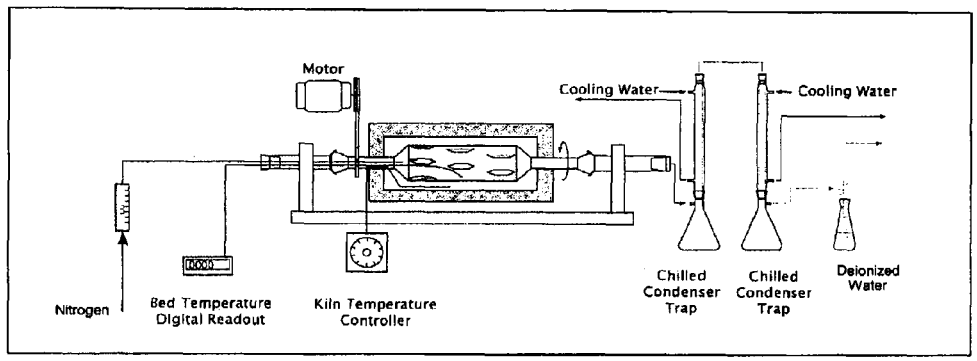

FIG. 7 is a schematic diagram of the equipment used for the scaled up pyrolysis of P4HB biomass.

DETAILED DESCRIPTION OF THE INVENTION

A description of example embodiments of the invention follows.

The present invention provides processes and methods for the manufacture of biobased gamma-butyrolactone (GBL) from a genetically engineered microbe producing poly-4-hydroxybutyrate polymer (P4HB biomass). For the purposes of this invention P4HB is defined to also include the copolymer of 4-hydroxybutyrate with 3-hydroxybutyrate where the % of 4-hydroxybutyrate in the copolymer is greater than 80%, 85%, 90% preferably greater than 95% of the monomers in the copolymer. In certain embodiments, the P4HB biomass is produced by improved P4HB production processes using the recombinant hosts described herein. These recombinant hosts have been genetically constructed to increase the yield of P4HB by manipulating (e.g., inhibition and/or overexpression) certain genes in the P4HB pathway to increase the yield of P4HB in the biomass. The P4HB biomass is produced in a fermentation process in which the genetically engineered microbe is fed a renewable substrate. Renewable substrates include fermentation feedstocks such as sugars, vegetable oils, fatty acids or synthesis gas produced from plant crop materials. The level of P4HB produced in the biomass from the sugar substrate is greater than 10% (e.g., about 20%, about 30%, about 40%, about 50%, about 60%, about 70%, about 80%) of the total dry weight of the biomass. The P4HB biomass is then combined with a catalyst and heated to thermally decompose the P4HB to biobased GBL.

Described herein are an alternative processes for manufacturing GBL based on using renewable carbon sources to produce a biobased poly-4-hydroxybutyrate (P4HB) polymer in a biomass that is then converted to biobased gamma-butyrolactone.

Biobased, biodegradable polymers such as polyhydroxyalkanoates (PHAs), are naturally produced in biomass systems, such as microbial biomass (e.g., bacteria including cyanobacteria, yeast, fungi), plant biomass, or algal biomass. Genetically-modified biomass systems have been developed which produce a wide variety of biodegradable PHA polymers and copolymers in high yield (Lee (1996), *Biotechnology & Bioengineering* 49:1-14; Braunegg et al. (1998), *J. Biotechnology* 65:127-161; Madison, L. L. and Huisman, G. W. (1999), Metabolic Engineering of Poly-3-Hydroxyalkanoates; From DNA to Plastic, in: *Microbiol. Mol. Biol. Rev,* 63:21-53). PHA polymers are well known to be thermally unstable compounds that readily degrade when heated up to and beyond their melting points (Cornelissen et al., *Fuel,* 87, 2523, 2008). This is usually a limiting factor when processing the polymers for plastic applications that can, however, be leveraged to create biobased, chemical manufacturing processes starting from 100% renewable resources.

When pure poly-4-hydroxybutyrate (P4HB), produced using petroleum derived 1,4-butanediol, is heated up to 250-350° C., it thermally degrades to volatile GBL exclusively by unzipping of the polymer chain (Kim et al. (2006), Polymer Degradation and Stability, 91:2333-2341). As described herein, the addition of low cost catalysts are added to a genetically engineered biomass with an increased production of P4HB to speed up the degradation reaction to gamma-butyrolactone. The gamma-butyrolactone is recovered and the inexpensive catalyst is left with the residual biomass or can optionally be recycled back to the process after suitable regeneration including thermal regeneration. Combining the catalyst reaction with specifically genetically modified, high yielding P4HB producing biomass is an economical and environmental alternative to the traditional petroleum-based processes.

Recombinant Hosts with Metabolic Pathways for Producing P4HB

Genetic engineering of hosts (e.g, bacteria, fungi, algae, plants and the like) as production platforms for modified and new materials provides a sustainable solution for high value eco-friendly industrial applications for production of chemicals. Described herein are process methods of producing biobased gamma-butyrolactone from a genetically modified recombinant polyhydroxyalkanoate P4HB biomass. The processes described herein avoid toxic effects to the host organism by producing the biobased chemical post culture or post harvesting, are cost effective and highly efficient (e.g., use less energy to make), decrease greenhouse gas emissions, use renewable resources and can be further processed to produce high purity products from GBL in high yield.

The PHA biomass utilized in the methods described herein is genetically engineered to produce poly-4-hydroxybutyrate (P4HB). An exemplary pathway for production of P4HB is provided in FIG. 1 and a more detailed description of the pathway, recombinant hosts that produce P4HB biomass is provided below. The pathway can be engineered to increase production of P4HB from carbon feed sources.

As used herein, "P4HB biomass" is intended to mean any genetically engineered biomass from a recombinant host (e.g., bacteria,) that includes a non-naturally occurring amount of the polyhydroxyalkanoate polymer e.g. poly-4-hydroxybutyrate (P4HB). In some embodiments, a source of the P4HB biomass is bacteria, yeast, fungi, algae, plant crop cyanobacteria, or a mixture of any two or more thereof. In certain embodiments, the biomass titer (g/L) of P4HB has been increased when compared to the host without the overexpression or inhibition of one or more genes in the P4HB pathway. In certain embodiments, the P4HB titer is reported as a percent dry cell weight (% dcw) or as grams of P4HB/Kg biomass.

"Overexpression" refers to the expression of a polypeptide or protein encoded by a DNA introduced into a host cell, wherein the polypeptide or protein is either not normally present in the host cell, or where the polypeptide or protein is present in the host cell at a higher level than that normally expressed from the endogenous gene encoding the polypeptide or protein. "Inhibition" or "down regulation" refers to the suppression or deletion of a gene that encodes a polypeptide or protein. In some embodiments, inhibition means inactivating the gene that produces an enzyme in the pathway. In certain embodiments, the genes introduced are from a heterologous organism.

Genetically engineered microbial PHA production systems with fast growing hosts such as *Escherichia coli* have been developed. In certain embodiments, genetic engineering also allows for the modification of wild-type microbes to improve the production of the P4HB polymer. Examples of PHA production modifications are described in Steinbuchel & Valentin, *FEMS Microbiol. Lett.* 128:219-28 (1995). PCT Publication No. WO 98/04713 describes methods for controlling the molecular weight using genetic engineering to control the level of the PHA synthase enzyme. Commercially useful strains, including *Alcaligenes eutrophus* (renamed as *Ralstonia eutropha*), *Alcaligenes latus, Azotobacter vinlandii,* and *Pseudomonads,* for producing PHAs are disclosed in Lee, *Biotechnology & Bioengineering,* 49:1-14 (1996) and Braunegg et al., (1998), *J. Biotechnology* 65: 127-161. U.S. Pat. Nos. 6,316,262, 7,229,804 6,759,219 and 6,689,589 describe biological systems for manufacture of PHA polymers containing 4-hydroxyacids, incorporated by reference herein.

Although there have been reports of producing 4-hydroxybutyrate copolymers from renewable resources such as sugar or amino acids, the level of 4HB in the copolymers produced from scalable renewable substrates has been much less than 50% of the monomers in the copolymers and therefore unsuitable for practicing the disclosed invention. Production of the P4HB biomass using an engineered microorganism with renewable resources where the level of P4HB in the biomass is sufficient to practice the disclosed invention (i.e., greater than 40%, 50%, 60% or 65% of the total biomass dry weight) has not previously been achieved.

The weight percent PHA in the wild-type biomass varies with respect to the source of the biomass. For microbial systems produced by a fermentation process from renewable resource-based feedstocks such as sugars, vegetable oils or glycerol, the amount of PHA in the wild-type biomass may be about 65 wt %, or more, of the total weight of the biomass. For plant crop systems, in particular biomass crops such as sugarcane or switchgrass, the amount of PHA may be about 3%, or more, of the total weight of the biomass. For algae or cyanobacterial systems, the amount of PHA may be about 40%, or more of the total weight of the biomass.

In certain aspects of the invention, the recombinant host has been genetically engineered to produce an increased amount of P4HB as compared to the wild-type host. The wild-type P4HB biomass refers to the amount of P4HB that an organism typically produces in nature.

For example, in certain embodiments, the P4HB is increased between about 20% to about 90% over the wild-type or between about 50% to about 80%. In other embodiments, the recombinant host produces at least about a 20% increase of P4HB over wild-type, at least about a 30% increase over wild-type, at least about a 40% increase over wild-type, at least about a 50% increase over wild-type, at least about a 60% increase over wild-type, at least about a 70% increase over wild-type, at least about a 75% increase over wild-type, at least about a 80% increase over wild-type or at least about a 90% increase over wild-type. In other embodiments, the P4HB is between about a 2 fold increase to about a 400 fold increase over the amount produced by the wild-type host. The amount of P4HB in the host or plant is determined by gas chromatography according to procedures described in Doi, Microbial Polyesters, John Wiley&Sons, p 24, 1990. In certain embodiments, a biomass titer of 100-120 g P4HB/Kg of biomass is achieved. In other embodiments, the amount of P4HB titer is presented as percent dry cell weight (% dcw).

Suitable Host Strains

In certain embodiments, the host strain is *E. coli* K-12 strain LS5218 (Spratt et al., *J. Bacteriol.* 146 (3):1166-1169 (1981); Jenkins and Nunn, *J. Bacteriol.* 169 (1):42-52 (1987)). Other suitable *E. coli* K-12 host strains include, but are not limited to, MG1655 (Guyer et al., *Cold Spr. Harb. Symp. Quant. Biol.* 45:135-140 (1981)), WG1 and W3110 (Bachmann *Bacteriol. Rev.* 36(4):525-57 (1972)). Alternatively, *E. coli* strain W (Archer et al., *BMC Genomics* 2011, 12:9 doi:10.1186/1471-2164-12-9) or *E. coli* strain B (Delbruck and Luria, Arch. Biochem. 1:111-141 (1946)) and their derivatives such as REL606 (Lenski et al., Am. Nat. 138: 1315-1341 (1991)) are other suitable *E. coli* host strains.

Other exemplary microbial host strains include but are not limited to: *Ralstonia eutropha, Zoogloea ramigera, Allochromatium vinosum, Rhodococcus ruber, Delftia acidovorans, Aeromonas caviae, Synechocystis* sp. PCC 6803, *Synechococcus elongatus* PCC 7942, *Thiocapsa pfenigii, Bacillus megaterium, Acinetobacter baumannii, Acinetobacter baylyi, Clostridium kluyveri, Methylobacterium extorquens, Nocardia corralina, Nocardia salmonicolor, Pseudomonas fluorescens, Pseudomonas oleovorans, Pseudomonas* sp. 6-19, *Pseudomonas* sp. 61-3 and *Pseudomonas putida, Rhodobacter sphaeroides, Alcaligenes latus, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor,* and *Clostridium acetobutylicum.* Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris.*

Exemplary algal strains species include but are not limited to: *Chlorella* strains, species selected from: *Chlorella minutissima, Chlorella emersonii, Chlorella sorokiniana, Chlorella ellipsoidea, Chlorella* sp., or *Chlorella protothecoides.*

Source of Recombinant Genes

Sources of encoding nucleic acids for a P4HB pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Clostridium kluyveri, Clostridium acetobutylicum, Clostridium beijerinckii, Clostridium saccharoperbutylacetonicum, Clostridium perjringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculo-* sis, *Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Chlorella minutissima, Chlorella emersonii, Chlorella sorokiniana, Chlorella ellipsoidea, Chlorella* sp., *Chlorella protothecoides, Homo sapiens, Oryctolagus cuniculus, Rhodobacter spaeroides, Thermoanaerobacter brockii, Metallosphaera sedula, Leuconostoc mesenteroides, ChloroJlexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salina rum, Geobacillus stearothermophilus, Aeropyrum pernix, Sus scrofa, Caenorhabditis elegans, Corynebacterium glutamicum, Acidaminococcusfermentans, Lactococcus lac tis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum* marine gamma proteobacterium, and butyrate-producing bacterium. For example, microbial hosts (e.g., organisms) having P4HB biosynthetic production are exemplified herein with reference to an *E. coli* host. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite P4HB biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of P4HB and other compounds of the invention described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

Production of Transgenic Host for Producing 4HB

Figure 1:
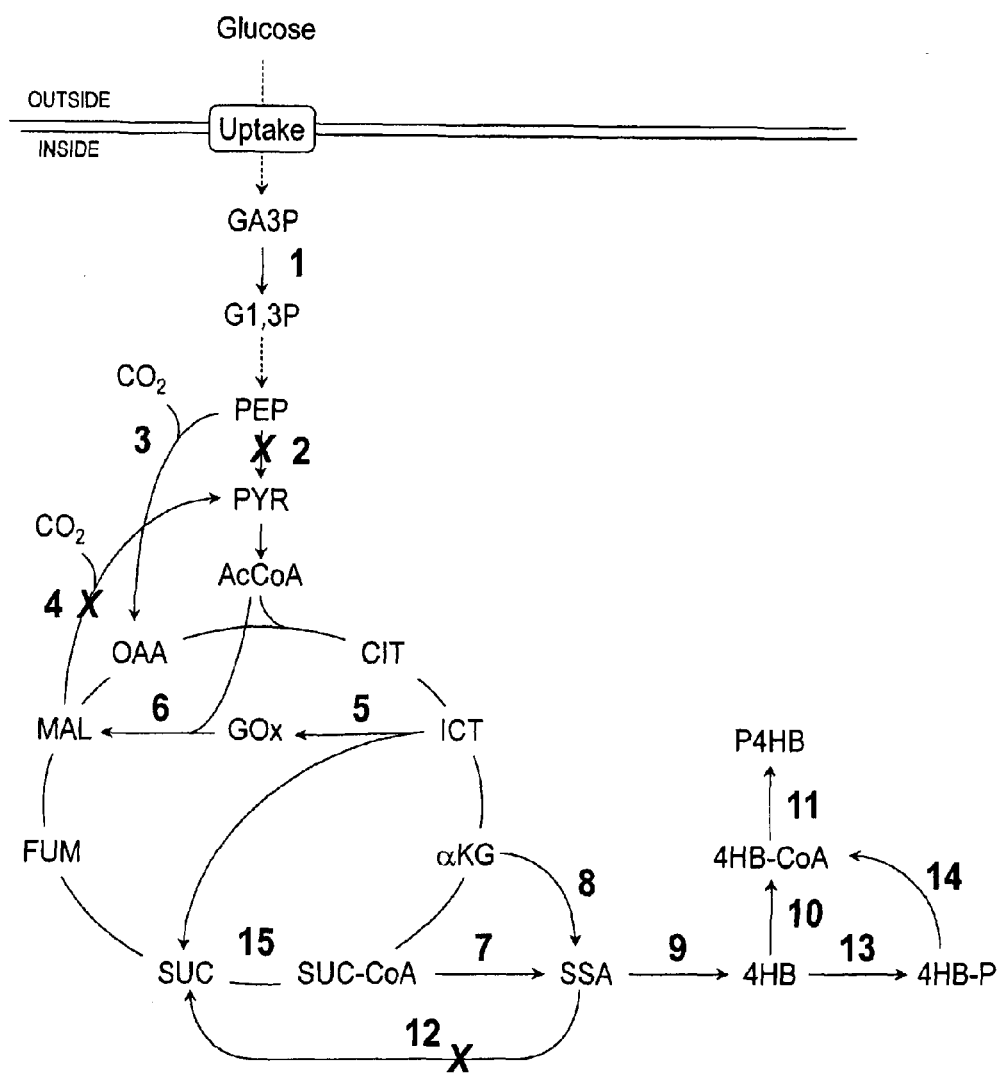
FIG. 1 is a schematic diagram of exemplary *E. coli* central metabolic pathways showing reactions that were modified or introduced in the Examples or could be modified. Numbers in the figure refer to reaction numbers in Table 1A. Reactions that were eliminated by deleting the corresponding genes are marked with an "X". Abbreviations: "GA3P", D-glyceraldehyde-3-phosphate; "G1,3P", 1,3-diphosphateglycerate; "PEP", phosphoenolpyruvate; "PYR", pyruvate; "AcCoA", acetyl-CoA; "CIT", citrate; "ICT", isocitrate; "aKG", alpha-ketoglutarate; "SUC-CoA", succinyl CoA; "SUC", succinate; "Fum", fumarate; "MAL", L-malate; "OAA", oxaloacetate; "SSA", succinic semialdehyde; "4HB", 4-hydroxybutyrate; "4HB-CoA", 4-hydroxybutyryl CoA.

Transgenic (Recombinant) hosts for producing P4HB are genetically engineered using conventional techniques known in the art. The genes cloned and/or assessed for host strains producing P4HB-containing PHA and 4-carbon chemicals are presented below in Table 1A, along with the appropriate Enzyme Commission number (EC number) and references. Some genes were synthesized for codon optimization while others were cloned via PCR from the genomic DNA of the native or wild-type host. As used herein, "heterologous" means from another host. The host can be the same or different species. FIG. 1 is an exemplary pathway for producing P4HB.

TABLE 1A

Genes in microbial host strains producing 4HB-containing PHA and 4-carbon chemicals. A star (*) after the gene name denotes that the nucleotide sequence was optimized for expression in *E. coli*.

| Reaction number (FIG. 1) | Gene Name | Enzyme Name | EC Number | Accession No. |
|---|---|---|---|---|
| 1 | gapA | Glyceraldehyde 3-phosphate dehydrogenase | 1.2.1.12 | NP_416293 |
| 1 | gdp1 | Glyceraldehyde-3-phosphate dehydrogenase | 1.2.1.12 | XP_455496 |
| 1 | gap2 | Glyceraldehyde-3-phosphate dehydrogenase (NADP+) (phosphorylating) | 1.2.1.59 | CAA58550 |
| 1 | gapB | Glyceraldehyde-3-phosphate dehydrogenase 2 | 1.2.1.59 | NP_390780 |
| 1 | gapN | Putative NADP-dependent glyceraldehyde-3-phosphate dehydrogenase | 1.2.1.12 | NP_664849 |
| 2 | pykF | Pyruvate kinase I | 2.7.1.40 | b1676 |
| 2 | pykA | Pyruvate kinase II | 2.7.1.40 | b1854 |
| 3 | ppc$_{Ec}$ | Phosphoenolpyruvate carboxylase | 4.1.1.31 | NP_418391 |
| 3 | ppc$_{Ms}$* | Phosphoenolpyruvate carboxylase | 4.1.1.31 | Gene/Protein ID 1; Q02735 |
| 4 | maeA | Malate dehydrogenase, NAD-requiring | 1.1.1.38 | b1479 |
| 4 | maeB | Malate dehydrogenase (oxaloacetate-decarboxylating) (NADP+) | 1.1.1.40 | b2463 |
| 5 | aceA | Isocitrate lyase | 4.1.3.1 | NP_418439 |
| 6 | aceB | Malate synthase A | 2.3.3.9 | NP_418438 |
| 7 | sucD* | Succinate semialdehyde dehydrogenase | 1.2.1.76 | Gene/Protein ID 2; YP_001396394 |
| 8 | kgdM | Alpha-ketoglutarate decarboxylase | 4.1.1.71 | NP_335730 |
| 9 | ssaR$_{At}$* | Succinic semialdehyde reductase | 1.1.1.61 | Gene/Protein ID 3; AAK94781 |
| 9 | 4hbD | Succinic semialdehyde reductase | 1.1.1.61 | YP_001396393 |
| 9 | ssaR$_{At2}$* | Succinic semialdehyde reductase | 1.1.1.61 | Gene/Protein ID 4; XP_001210625 |
| 9 | ssaR$_{Mm}$* | Succinic semialdehyde reductase | 1.1.1.61 | Gene/Protein ID 5; AKR7A5; |
| 9 | yqhD | Succinic semialdehyde reductase | 1.1.1.61 | NP_417484 |
| 10 | orfZ | CoA transferase | 2.8.3.n | AAA92344 |
| 11 | phaC1 | Polyhydroxyalkanoate synthase | 2.3.1.n | YP_725940 |
| 11 | phaC3/C1* | Polyhydroxyalkanoate synthase fusion protein | 2.3.1.n | Gene/Protein ID 6 |
| 12 | ynel | Succinate-semialdehyde dehydrogenase, NADP+-dependent | 1.2.1.24 | NP_416042 |
| 12 | gabD | Succinate-semialdehyde dehydrogenase, NADP+-dependent | 1.2.1.16 | NP_417147 |
| 13 | buk1 | Butyrate kinase I | 2.7.2.7 | NP_349675 |
| 13 | buk2 | Butyrate kinase II | 2.7.2.7 | NP_348286 |
| 14 | ptb | Phosphotransbutyrylase | 2.3.1.19 | NP_349676 |
| 15 | sucCD | Succinate-CoA ligase (ADP-forming) | 6.2.1.5 | NP_286444 NP_286445 |
| 15 | cat1 | Succinyl-CoA: coenzyme A transferase | 2.8.3.n | YP_001396395 |

Other proteins capable of catalyzing the reactions listed in Table 1A can be discovered by consulting the scientific literature, patents or by BLAST searches against e.g. nucleotide or protein databases at NCBI (www.ncbi.nlm.nih.gov/). Synthetic genes can then be created to provide an easy path from sequence databases to physical DNA. Such synthetic genes are designed and fabricated from the ground up, using codons to enhance heterologous protein expression, optimizing characteristics needed for the expression system and host. Companies such as e.g. DNA 2.0 (Menlo Park, Calif. 94025, USA) will provide such routine service. Proteins that may catalyze some of the biochemical reactions listed in Table 1A are provided in Tables 1B-1Z.

TABLE 1B

Suitable homologues for the GapA protein (glyceraldehyde 3-phosphate dehydrogenase-A, from *Escherichia coli*, EC No. 1.2.1.12, which acts on D-glyceraldehyde 3-phosphate to produce 1,3-diphosphateglycerate; protein acc. no. NP_416293.1)

| Protein Name | Protein Accession No. |
| --- | --- |
| glyceraldehyde-3-phosphate dehydrogenase | NP_456222 |
| glyceraldehyde-3-phosphate dehydrogenase A | ZP_04561688 |
| glyceraldehyde-3-phosphate dehydrogenase | CBK85249 |
| glyceraldehyde-3-phosphate dehydrogenase, type I | ZP_05729429 |
| glyceraldehyde-3-phosphate dehydrogenase | ZP_04613128 |
| glyceraldehyde-3-phosphate dehydrogenase | NP_929794 |
| glyceraldehyde-3-phosphate dehydrogenase A | YP_002648641 |
| glyceraldehyde-3-phosphate dehydrogenase A | CBA72924 |
| glyceraldehyde-3-phosphate dehydrogenase A | ZP_07394569 |

TABLE 1C

Suitable homologues for the Gdp1 protein (glyceraldehyde 3-phosphate dehydrogenase, from *Kluyveromyces lactis*, EC No. 1.2.1.12, which acts on D-glyceraldehyde 3-phosphate to produce 1,3-diphosphateglycerate; protein ace. no. XP_455496)

| Protein Name | Protein Accession No. |
| --- | --- |
| hypothetical protein | XP_446770 |
| unnamed protein product | CAA24607 |
| glyceraldehyde 3-phosphate dehydrogenase | EDN63283 |
| glyceraldehyde 3-phosphate dehydrogenase | Q9UVC0 |
| glyceraldehyde 3-phosphate dehydrogenase | XP_002171328 |
| glyceraldehyde 3-phosphate dehydrogenase | Q01077 |
| hypothetical protein CRE_18959 | XP_003115497 |
| glyceraldehyde 3-phosphate dehydrogenase | CAA06030 |
| glyceraldehyde 3-phosphate dehydrogenase | ABQ81648 |

TABLE 1D

Suitable homologues for the Gap2 protein (glyceraldehyde-3-phosphatedehydrogenase (NADP+) (phosphorylating), from *Synechocystis sp.*, EC No. 1.2.1.59, which acts on D-glyceraldehyde 3-phosphate to produce 1,3-diphosphateglycerate; protein ace. no. CAA58550)

| Protein Name | Protein Accession No. |
| --- | --- |
| glyceraldehyde 3-phosphate dehydrogenase | NP_442821 |
| glyceraldehyde 3-phosphate dehydrogenase | YP_003889819 |
| glyceraldehyde 3-phosphate dehydrogenase | YP_002372721 |
| unnamed protein product | CAO91151 |
| glyceraldehyde 3-phosphate dehydrogenase | ZP_01729953 |
| glyceraldehyde 3-phosphate dehydrogenase | YP_723521 |
| glyceraldehyde 3-phosphate dehydrogenase, type I | ZP_06309941 |
| glyceraldehyde 3-phosphate dehydrogenase | ZP_07113693 |
| glyceraldehyde 3-phosphate dehydrogenase | ZP_01623628 |

TABLE 1E

Suitable homologues for the GapB protein (glyceraldehyde-3-phosphate dehydrogenase 2, from *Bacillus subtilis*, EC No. 1.2.1.59, which acts on D-glyceraldehyde 3-phosphate to produce 1,3-diphosphateglycerate; protein acc. no. NP_390780)

| Protein Name | Protein Accession No. |
| --- | --- |
| glyceraldehyde 3-phosphate dehydrogenase | YP_003974321 |
| glyceraldehyde 3-phosphate dehydrogenase | YP_003921301 |
| glyceraldehyde 3-phosphate dehydrogenase | YP_001487767 |
| glyceraldehyde 3-phosphate dehydrogenase | YP_080196 |
| glyceraldehyde 3-phosphate dehydrogenase | YP_148579 |
| glyceraldehyde 3-phosphate dehydrogenase | YP_001376482 |
| glyceraldehyde 3-phosphate dehydrogenase | ZP_01173259 |
| glyceraldehyde 3-phosphate dehydrogenase, type I | ZP_06809473 |
| glyceraldehyde 3-phosphate dehydrogenase | YP_001126741 |

TABLE 1F

Suitable homologues for the GapN protein (putative NADP-dependent glyceraldehyde-3-phosphate dehydrogenase, from *Streptococcus pyogenes*, EC No. 1.2.1.12, which acts on D-glyceraldehyde 3-phosphate to produce 1,3-diphosphateglycerate; protein acc. no. NP_664849)

| Protein Name | Protein Accession No. |
| --- | --- |
| NADP-dependent glyceraldehyde-3-phosphate dehydrogenase | YP_002997128 |
| NADP-dependent glyceraldehyde-3-phosphate dehydrogenase | YP_002744716 |
| NADP-dependent glyceraldehyde-3-phosphate dehydrogenase | Q3C1A6 |
| glyceraldehyde-3-phosphate dehydrogenase (NADP+) | ZP_07725052 |
| NADP-dependent glyceraldehyde-3-phosphate dehydrogenase | YP_820625 |
| NADP-dependent glyceraldehyde-3-phosphate dehydrogenase, putative | YP_001034755 |
| NAD-dependent DNA ligase LigA | ZP_01825832 |
| glyceraldehyde-3-phosphate dehydrogenase (NADP+) | ZP_06011937 |
| aldehyde dehydrogenase | YP_003307897 |

TABLE 1G

Suitable homologues for the Ppc protein (phosphoenolpyruvate carboxylase, from *Escherichia coli*, EC No. 4.1.1.31, which acts on phosphoenolpyruvate and carbon dioxide to produce oxaloacetate; protein acc. no. NP_418391)

| Protein Name | Protein Accession No. |
| --- | --- |
| phosphoenolpyruvate carboxylase | ZP_02904134 |
| phosphoenolpyruvate carboxylase | YP_002384844 |
| phosphoenolpyruvate carboxylase | YP_003367228 |
| phosphoenolpyruvate carboxylase | ZP_02345134 |
| phosphoenolpyruvate carboxylase | ZP_04558550 |
| phosphoenolpyruvate carboxylase | YP_003615503 |
| phosphoenolpyruvate carboxylase | YP_002241183 |
| phosphoenolpyruvate carboxylase | CBK84190 |
| phosphoenolpyruvate carboxylase | YP_003208553 |

TABLE 1H

Suitable homologues for the Ppc protein (phosphoenolpyruvate carboxylase, from *Medicago saliva*, EC No. 4.1.1.31, which acts on phosphoenolpyruvate and carbon dioxide to produce oxaloacetate; protein acc. no. Q02909)

| Protein Name | Protein Accession No. |
| --- | --- |
| phosphoenolpyruvate carboxylase | CAA09588 |
| phosphoenolpyruvate carboxylase | P51061 |
| phosphoenolpyruvate carboxylase 3 | AAU07998 |
| phosphoenolpyruvate carboxylase | ACN32213 |
| phosphoenolpyruvate carboxylase | BAC20365 |
| predicted protein | XP_002330719 |
| phosphoenolpyruvate carboxylase | ABV80356 |
| phosphoenolpyruvate carboxylase | AAD31452 |
| phosphoenolpyruvate carboxylase | CAJ86550 |

TABLE 1I

Suitable homologues for the AceA protein (isocitrate lyase, from *Escherichia coli* K-12, EC No. 4.1.3.1, which acts on isocitrate to produce glyoxylate and succinate; protein acc. no. NP_418439)

| Protein Name | Protein Accession No. |
| --- | --- |
| isocitrate lyase | NP_290642 |
| isocitrate lyase | ZP_04558565 |
| isocitrate lyase | YP_002218096 |
| isocitrate lyase, putative | YP_002932565 |
| isocitrate lyase | YP_002241049 |
| hypothetical protein ESA_00054 | YP_001436195 |
| isocitrate lyase | YP_003261295 |
| isocitrate lyase family protein | ZP_07952710 |
| isocitrate lyase | YP_002514615 |
| isocitrate lyase | YP_001234628 |

TABLE 1J

Suitable homologues for the AceB protein (malate synthase A, from *Escherichia coli* K-12, EC No. 2.3.3.9, which acts on glyoxylate and acetyl-CoA to produce malate; protein acc. no. NP_418438)

| Protein Name | Protein Accession No. |
| --- | --- |
| malate synthase | YP_002385083 |
| malate synthase A | ZP_06356448 |
| malate synthase | YP_002917220 |
| malate synthase | YP_001480725 |
| malate synthase | YP_001399288 |
| malate synthase A | YP_003714066 |
| malate synthase | NP_933534 |
| malate synthase A | YP_002253716 |
| malate synthase | YP_081279 |

TABLE 1K

Suitable homologues for the SucD protein (succinate semialdehyde dehydrogenase, from *Clostridium kluyveri*, EC No. 1.2.1.76, which acts on succinyl-CoA to produce succinate semialdehyde; protein acc. no. YP_001396394)

| Protein Name | Protein Accession No. |
| --- | --- |
| CoA-dependent succinate semialdehyde dehydrogenase | AAA92347 |
| succinate-semialdehyde dehydrogenase [NAD(P)+] | ZP_06559980 |
| succinate-semialdehyde dehydrogenase [NAD(P)+] | ZP_05401724 |
| aldehyde-alcohol dehydrogenase family protein | ZP_07821123 |
| succinate-semialdehyde dehydrogenase [NAD(P)+] | ZP_06983179 |
| succinate-semialdehyde dehydrogenase | YP_001928839 |

TABLE 1K-continued

Suitable homologues for the SucD protein (succinate semialdehyde dehydrogenase, from *Clostridium kluyveri*, EC No. 1.2.1.76, which acts on succinyl-CoA to produce succinate semialdehyde; protein acc. no. YP_001396394)

| Protein Name | Protein Accession No. |
| --- | --- |
| hypothetical protein CLOHYLEM_05349 | ZP_03778292 |
| succinate-semialdehyde dehydrogenase [NAD(P)+] | YP_003994018 |
| succinate-semialdehyde dehydrogenase | NP_904963 |

TABLE 1L

Suitable homologues for the KgdM protein (alpha-ketoglutarate decarboxylase, from *Mycobacterium tuberculosis*, EC No. 4.1.1.71, which acts on alpha-ketoglutarate to produce succinate semialdehyde and carbon dioxide; protein acc. no. NP_335730)

| Protein Name | Protein Accession No. |
| --- | --- |
| alpha-ketoglutarate decarboxylase | YP_001282558 |
| alpha-ketoglutarate decarboxylase | NP_854934 |
| 2-oxoglutarate dehydrogenase sucA | ZP_06454135 |
| 2-oxoglutarate dehydrogenase sucA | ZP_04980193 |
| alpha-ketoglutarate decarboxylase | NP_961470 |
| alpha-ketoglutarate decarboxylase Kgd | YP_001852457 |
| alpha-ketoglutarate decarboxylase | NP_301802 |
| alpha-ketoglutarate decarboxylase | ZP_05215780 |
| alpha-ketoglutarate decarboxylase | YP_001702133 |

TABLE 1M

Suitable homologues for the SsaR$_{At}$ protein (succinic semialdehyde reductase, from *Arabidopsis thaliana*, EC No. 1.1.1.61, which acts on succinate semialdehyde to produce 4-hydroxybutyrate; protein acc. no. AAK94781)

| Protein Name | Protein Accession No. |
| --- | --- |
| 6-phosphogluconate dehydrogenase NAD-binding domain-containing protein | XP_002885728 |
| hypothetical protein isoform 1 | XP_002266252 |
| predicted protein | XP_002320548 |
| hypothetical protein isoform 2 | XP_002266296 |
| unknown | ACU22717 |
| 3-hydroxyisobutyrate dehydrogenase, putative | XP_002524571 |
| unknown | ABK22179 |
| unknown | ACJ85049 |
| predicted protein | XP_001784857 |

TABLE 1N

Suitable homologues for the 4hbD protein (succinic semialdehyde reductase, from *Clostridium kluyveri*, EC No. 1.1.1.61, which acts on succinate semialdehyde to produce 4-hydroxybutyrate ; protein acc. no. YP_001396393)

| Protein Name | Protein Accession No. |
| --- | --- |
| NAD-dependent 4-hydroxybutyrate dehydrogenase | NP_348201 |
| NAD-dependent 4-hydroxybutyrate dehydrogenase | ZP_05401720 |
| 4-hydroxybutyrate dehydrogenase | ZP_06902666 |
| NAD-dependent 4-hydroxybutyrate dehydrogenase | ZP_06983178 |
| NAD-dependent 4-hydroxybutyrate dehydrogenase | NP_904964 |
| NAD-dependent 4-hydroxybutyrate dehydrogenase | ZP_04389726 |
| alcohol dehydrogenase, iron-dependent | ZP_07821131 |

TABLE 1N-continued

Suitable homologues for the 4hbD protein (succinic semialdehyde reductase, from *Clostridium kluyveri*, EC No. 1.1.1.61, which acts on succinate semialdehyde to produce 4-hydroxybutyrate ; protein acc. no. YP_001396393)

| Protein Name | Protein Accession No. |
| --- | --- |
| NAD-dependent 4-hydroxybutyrate dehydrogenase | ZP_05427218 |
| hypothetical protein CLOL250_02815 | ZP_02076027 |

TABLE 1O

Suitable homologues for the SsaR$_{At2}$ protein (succinic semialdehyde reductase, from *Aspergillus terreus*, EC No. 1.1.1.61, which acts on succinate semialdehyde to produce 4-hydroxybutyrate; protein acc. no. XP_001210625)

| Protein Name | Protein Accession No. |
| --- | --- |
| aflatoxin B1-aldehyde reductase, putative | XP_001268918 |
| aflatoxin B1-aldehyde reductase, putative | XP_001264422 |
| hypothetical protein An08g06440 | XP_001392759 |
| Pc13g11860 | XP_002559603 |
| TPA: aflatoxin B1-aldehyde reductase GliO-like, putative | CBF89011 |
| aflatoxin B1 aldehyde reductase | EEH21318 |
| aflatoxin B1 aldehyde reductase member, putative | XP_003069315 |
| aldo/keto reductase | XP_002625767 |
| aflatoxin B1 aldehyde reductase member 2 | XP_002845070 |

TABLE 1P

Suitable homologues for the SsaR$_{Mm}$ protein (succinic semialdehyde reductase, from *Mus musculus*, EC No. 1.1.1.61, which acts on succinate semialdehyde to produce 4-hydroxybutyrate; protein acc. no. AKR7A5)

| Protein Name | Protein Accession No. |
| --- | --- |
| aflatoxin B1 aldehyde reductase member 2 | XP_001092177 |
| AKR7A2 protein | AAI49541 |
| similar to aflatoxin B1 aldehyde reductase member 3 | XP_001917301 |
| aldo-keto reductase family 7, member A3 | XP_002685838 |

TABLE 1Q

Suitable homologues for the YqhD protein (succinic semialdehyde reductase, from *Escherichia coli* K-12, EC No. 1.1.1.61, which acts on succinate semialdehyde to produce 4-hydroxybutyrate; protein acc. no. NP_417484)

| Protein Name | Protein Accession No. |
| --- | --- |
| alcohol dehydrogenase yqhD | ZP_02900879 |
| alcohol dehydrogenase, NAD(P)-dependent | YP_002384050 |
| putative alcohol dehydrogenase | YP_003367010 |
| alcohol dehydrogenase YqhD | ZP_02667917 |
| putative alcohol dehydrogenase | YP_218095 |
| hypothetical protein ESA_00271 | YP_001436408 |
| iron-containing alcohol dehydrogenase | YP_003437606 |
| hypothetical protein CKO_04406 | YP_001455898 |
| alcohol dehydrogenase | ZP_03373496 |

TABLE 1R

Suitable homologues for the OrfZ protein (CoA transferase, from *Clostridium kluyveri* DSM 555, EC No. 2.8.3.n, which acts on 4-hydroxybutyrate to produce 4-hydroxybutyryl CoA; protein acc. no. AAA92344)

| Protein Name | Protein Accession No. |
| --- | --- |
| 4-hydroxybutyrate coenzyme A transferase | YP_001396397 |
| acetyl-CoA hydrolase/transferase | ZP_05395303 |
| acetyl-CoA hydrolase/transferase | YP_001309226 |
| 4-hydroxybutyrate coenzyme A transferase | NP_781174 |
| 4-hydroxybutyrate coenzyme A transferase | ZP_05618453 |
| acetyl-CoA hydrolase/transferase | ZP_05634318 |
| 4-hydroxybutyrate coenzyme A transferase | ZP_00144049 |
| hypothetical protein ANASTE_01215 | ZP_02862002 |
| 4-hydroxybutyrate coenzyme A transferase | ZP_07455129 |

TABLE 1S

Suitable homologues for the PhaC1 protein (polyhydroxyalkanoate synthase, from *Ralstonia eutropha* H16, EC No. 2.3.1.n, which acts on (R)-3-hydroxybutyryl-CoA or 4-hydroxybutyryl-CoA + [(R)-3-hydroxybutanoate-co-4-hydroxybutanoate]$_n$ to produce [(R)-3-hydroxybutanoate-co-4-hydroxybutanoate]$_{(n+1)}$ + CoA and also acts on 4-hydroxybutyryl-CoA + [4-hydroxybutanoate]$_n$ to produce [4-hydroxybutanoate]$_{(n+1)}$ + CoA; Protein acc. no. YP_725940 (Peoples and Sinskey, J. Biol. Chem. 264:15298-15303 (1989))).

| Protein Name | Protein Accession No. |
| --- | --- |
| polyhydroxyalkanoic acid synthase | YP_002005374 |
| PHB synthase | BAB96552 |
| PhaC | AAF23364 |
| Polyhydroxyalkanoate synthase protein PhaC | AAC83658 |
| polyhydroxybutyrate synthase | AAL17611 |
| poly(R)-hydroxyalkanoic acid synthase, class I | YP_002890098 |
| poly-beta-hydroxybutyrate polymerase | YP_159697 |
| PHB synthase | CAC41638 |
| PHB synthase | YP_001100197 |

TABLE 1T

Suitable homologues for the PhaC3/C1 protein (Polyhydroxyalkanoate synthase fusion protein from *Pseudomonas putida* and *Ralstonia eutropha* JMP134, EC No. 2.3.1.n, which acts on (R)-3-hydroxybutyryl-CoA or 4-hydroxybutyryl-CoA + [(R)-3-hydroxybutanoate-co-4-hydroxybutanoate]$_n$ to produce [(R)-3-hydroxybutanoate-co-4-hydroxybutanoate]$_{(n+1)}$ + CoA and also acts on 4-hydroxybutyryl-CoA + [4-hydroxybutanoate]$_n$ to produce [4-hydroxybutanoate]$_{(n+1)}$ + CoA

| Protein Name | Protein Accession No. |
| --- | --- |
| Poly(R)-hydroxyalkanoic acid synthase, class I | YP_295561 |
| Poly(3-hydroxybutyrate) polymerase | YP_725940 |
| polyhydroxyalkanoic acid synthase | AAW65074 |
| polyhydroxyalkanoic acid synthase | YP_002005374 |
| Poly(R)-hydroxyalkanoic acid synthase, class I | YP_583508 |
| intracellular polyhydroxyalkanoate synthase | ADM24646 |
| Poly(3-hydroxyalkanoate) polymerase | ZP_00942942 |
| polyhydroxyalkanoic acid synthase | YP_003752369 |
| PhaC | AAF23364 |

TABLE 1U

Suitable homologues for the Buk1 protein (butyrate kinase I, from *Clostridium acetobutylicum* ATCC824, EC No. 2.7.2.7, which acts on 4-hydroxybutyrate to produce 4-hydroxybutyryl phosphate

| Protein Name | Protein Accession No. |
| --- | --- |
| butyrate kinase | YP_001788766 |
| butyrate kinase | YP_697036 |
| butyrate kinase | YP_003477715 |
| butyrate kinase | YP_079736 |
| acetate and butyrate kinase | ZP_01667571 |
| butyrate kinase | YP_013985 |
| butyrate kinase | ZP_04670620 |
| butyrate kinase | ZP_04670188 |
| butyrate kinase | ZP_07547119 |

TABLE 1V

Suitable homologues for the Buk2 protein (butyrate kinase II, from *Clostridium acetobutylicum* ATCC824, EC No. 2.7.2.7, which acts on 4-hydroxybutyrate to produce 4-hydroxybutyryl phosphate

| Protein Name | Protein Accession No. |
| --- | --- |
| butyrate kinase | YP_001311072 |
| hypothetical protein CLOSPO_00144 | ZP_02993103 |
| hypothetical protein COPEUT_01429 | ZP_02206646 |
| butyrate kinase | EFR5649 |
| butyrate kinase | ZP_0720132 |
| butyrate kinase | YP_0029418 |
| butyrate kinase | YP_002132418 |
| butyrate kinase | ZP_05389806 |
| phosphate butyryltransferase | ADQ27386 |

TABLE 1W

Suitable homologues for the Ptb protein (phosphotransbutyrylase, from *Clostridium acetobutylicum* ATCC824, EC No. 2.3.1.19, which acts on 4-hydroxybutyryl phosphate to produce 4-hydroxybutyryl CoA

| Protein Name | Protein Accession No. |
| --- | --- |
| phosphate butyryltransferase | YP_001884531 |
| hypothetical protein COPCOM_01477 | ZP_03799220 |
| phosphate butyryltransferase | YP_00331697 |
| phosphate butyryltransferase | YP_004204177 |
| phosphate acetyl/butyryltransferase | ZP_05265675 |
| putative phosphate acetyl/butyryltransferase | ZP_05283680 |
| bifunctional enoyl-CoA hydratase/phosphate acetyltransferase | YP_426556 |
| hypothetical protein CLOBOL_07039 | ZP_02089466 |
| phosphate butyryltransferase | YP_003564887 |

TABLE 1X

Suitable homologues for the SucC protein (succinate-CoA ligase (ADP-forming), beta subunit, from *Escherichia coli* K-12, EC No. 6.2.1.5, which acts on succinate and CoA to produce succinyl-CoA

| Protein Name | Protein Accession No. |
| --- | --- |
| succinyl-CoA synthetase, beta chain | YP_003942629 |
| succinyl-CoA synthetase subunit beta | YP_003005213 |
| succinyl-CoA synthetase subunit beta | YP_002150340 |
| succinyl-CoA ligase (ADP-forming) | ZP_06124567 |
| succinyl-CoA synthetase subunit beta | YP_001187988 |
| succinyl-CoA synthetase subunit beta | ZP_01075062 |
| succinyl-CoA ligase (ADP-forming) | ZP_05984280 |
| succinyl-CoA synthetase subunit beta | YP_003699804 |
| succinyl-CoA synthetase subunit beta | YP_003443470 |

TABLE 1Y

Suitable homologues for the SucD protein (succinate-CoA ligase (ADP-forming), alpha subunit, from *Escherichia coli* K-12, EC No. 6.2.1.5, which acts on succinate and CoA to produce succinyl-CoA

| Protein Name | Protein Accession No. |
| --- | --- |
| succinyl-CoA synthetase subunit alpha | YP_402344 |
| succinate-CoA ligase | ZP_07949625 |
| succinyl-CoA synthetase subunit alpha | NP_792024 |
| succinyl-CoA synthetase, alpha subunit | YP_001784751 |
| succinyl-CoA synthetase alpha chain | ZP_03822017 |
| succinyl-CoA ligase | ZP_07004580 |
| hypothetical protein ARALYDRAFT_489184 | XP_002872045 |
| succinyl-CoA synthetase subunit alpha | YP_896208 |
| succinyl-CoA synthetase (ADP-forming) alpha subunit | YP_611746 |

TABLE 1Z

Suitable homologues for the Cat1 protein (succinyl-CoA: coenzyme A transferase, from *Clostridium kluyveri* DSM 555, EC No. 2.8.3.n, which acts on succinate and acetyl-CoA to produce succinyl-CoA and acetate

| Protein Name | Protein Accession No. |
| --- | --- |
| succinyl-CoA synthetase subunit alpha | YP_402344 |
| succinate-CoA ligase | ZP_07949625 |
| succinyl-CoA synthetase subunit alpha | NP_792024 |
| succinyl-CoA synthetase, alpha subunit | YP_001784751 |
| succinyl-CoA synthetase alpha chain | ZP_03822017 |
| succinyl-CoA ligase | ZP_07004580 |
| hypothetical protein ARALYDRAFT_489184 | XP_002872045 |
| succinyl-CoA synthetase subunit alpha | YP_896208 |
| succinyl-CoA synthetase (ADP-forming) alpha subunit | YP_611746 |

Suitable Extrachromosomal Vectors and Plasmids

A "vector," as used herein, is an extrachromosomal replicon, such as a plasmid, phage, or cosmid, into which another DNA segment may be inserted so as to bring about the replication of the inserted segment. Vectors vary in copy number and depending on the origin of their replication they contain, their size, and the size of insert. Vectors with different origin of replications can be propagated in the same microbial cell unless they are closely related such as pMB1 and ColE1. Suitable vectors to express recombinant proteins can constitute pUC vectors with a pMB1 origin of replication having 500-700 copies per cell, pBluescript vectors with a ColE1 origin of replication having 300-500 copies per cell, pBR322 and derivatives with a pMB1 origin of replication having 15-20 copies per cell, pACYC and derivatives with a p15A origin of replication having 10-12 copies per cell, and pSC101 and derivatives with a pSC101 origin of replication having about 5 copies per cell as described in the QIAGEN® Plasmid Purification Handbook (found on the world wide web at: //kirshner.med.harvard.edu/files/protocols/QIAGEN_QIAGENPlasmidPurification_EN.pdf).

Suitable Strategies and Expression Control Sequences for Recombinant Gene Expression Strategies for achieving expression of recombinant genes in *E. coli* have been extensively described in the literature (Gross, Chimica Oggi 7(3):21-29 (1989); Olins and Lee, Cur. Op. Biotech. 4:520-525 (1993); Makrides, Microbiol. Rev. 60(3):512-538 (1996); Hannig and Makrides, Trends in Biotech, 16:54-60 (1998)). Expression control sequences can include constitutive and inducible promoters, transcription enhancers, transcription terminators, and the like which are well known in the art. Suitable promoters include, but are not limited to, $P_{lac}$, $P_{tac}$, $P_{trc}$, $P_R$, $P_L$, $P_{trp}$, $P_{phoA}$, $P_{ara}$, $P_{uspA}$, $P_{rspU}$, $P_{syn}$ (Rosenberg and Court, Ann. Rev. Genet. 13:319-353 (1979); Hawley and McClure, Nucl. Acids Res. 11 (8):2237-2255 (1983); Harley and Raynolds, Nucl. Acids Res. 15:2343-2361 (1987); also ecocyc.org and partsregistry.org.

Construction of Recombinant Hosts

Recombinant hosts containing the necessary genes that will encode the enzymatic pathway for the conversion of a carbon substrate to P4HB may be constructed using techniques well known in the art.

Methods of obtaining desired genes from a source organism (host) are common and well known in the art of molecular biology. Such methods can be found described in, for example, Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999). For example, if the sequence of the gene is known, the DNA may be amplified from genomic DNA using polymerase chain reaction (Mullis, U.S. Pat. No. 4,683,202) with primers specific to the gene of interest to obtain amounts of DNA suitable for ligation into appropriate vectors. Alternatively, the gene of interest may be chemically synthesized de novo in order to take into consideration the codon bias of the host organism to enhance heterologous protein expression. Expression control sequences such as promoters and transcription terminators can be attached to a gene of interest via polymerase chain reaction using engineered primers containing such sequences. Another way is to introduce the isolated gene into a vector already containing the necessary control sequences in the proper order by restriction endonuclease digestion and ligation. One example of this latter approach is the BioBrick™ technology (see the world wide web at biobricks.org) where multiple pieces of DNA can be sequentially assembled together in a standardized way by using the same two restriction sites.

In addition to using vectors, genes that are necessary for the enzymatic conversion of a carbon substrate to P4HB can be introduced into a host organism by integration into the chromosome using either a targeted or random approach. For targeted integration into a specific site on the chromosome, the method generally known as Red/ET recombineering is used as originally described by Datsenko and Wanner (Proc. Natl. Acad. Sci. USA, 2000, 97, 6640-6645). Random integration into the chromosome involved using a mini-Tn5 transposon-mediated approach as described by Huisman et al. (U.S. Pat. Nos. 6,316,262 and 6,593,116).

Culturing of Host to Produce P4HB Biomass

In general, the recombinant host is cultured in a medium with a carbon source and other essential nutrients to produce the P4HB biomass by fermentation techniques either in batches or continuously using methods known in the art. Additional additives can also be included, for example, antifoaming agents and the like for achieving desired growth conditions. Fermentation is particularly useful for large scale production. An exemplary method uses bioreactors for culturing and processing the fermentation broth to the desired product. Other techniques such as separation techniques can be combined with fermentation for large scale and/or continuous production.

As used herein, the term "feedstock" refers to a substance used as a carbon raw material in an industrial process. When used in reference to a culture of organisms such as microbial or algae organisms such as a fermentation process with cells, the term refers to the raw material used to supply a carbon or other energy source for the cells. Carbon sources useful for the production of GBL include simple, inexpensive sources, for example, glucose, sucrose, lactose, fructose, xylose, maltose, arabinose and the like alone or in combination. In other embodiments, the feedstock is molasses or starch, fatty acids, vegetable oils or a lignocelluloses material and the like. It is also possible to use organisms to produce the P4HB biomass that grow on synthesis gas ($CO_2$, CO and hydrogen) produced from renewable biomass resources.

Introduction of P4HB pathway genes allows for flexibility in utilizing readily available and inexpensive feedstocks. A "renewable" feedstock refers to a renewable energy source such as material derived from living organisms or their metabolic byproducts including material derived from biomass, often consisting of underutilized components like chaff or stover. Agricultural products specifically grown for use as renewable feedstocks include, for example, corn, soybeans, switchgrass and trees such as poplar, wheat, flaxseed and rapeseed, sugar cane and palm oil. As renewable sources of energy and raw materials, agricultural feedstocks based on crops are the ultimate replacement of declining oil reserves. Plants use solar energy and carbon dioxide fixation to make thousands of complex and functional biochemicals beyond the current capability of modern synthetic chemistry. These include fine and bulk chemicals, pharmaceuticals, nutraceuticals, flavanoids, vitamins, perfumes, polymers, resins, oils, food additives, bio-colorants, adhesives, solvents, and lubricants.

Combining P4HB Biomass with Catalyst

In general, during or following production (e.g., culturing) of the P4HB biomass, the biomass is combined with a catalyst under suitable conditions to help convert the P4HB polymer to high purity gamma-butyrolactone product. The catalyst (in solid or solution form) and biomass are combined for example by mixing, flocculation, centrifuging or spray drying, or other suitable method known in the art for promoting the interaction of the biomass and catalyst driving an efficient and specific conversion of P4HB to gamma-butyrolactone. In some embodiments, the biomass is initially dried, for example at a temperature between about 100° C. and about 150° C. and for an amount of time to reduce the water content of the biomass. The dried biomass is then re-suspended in water prior to combining with the catalyst. Suitable temperatures and duration for drying are determined for product purity and yield and can in some embodiments include low temperatures for removing water (such as between 25° C. and 150° C.) for an extended period of time or in other embodiments can include drying at a high temperature (e.g., above 450° C.) for a short duration of time. Under "suitable conditions" refers to conditions that promote the catalytic reaction. For example, under conditions that maximize the generation of the product gamma-butyrolactone such as in the presence of co-agents or other material that contributes to the reaction efficiency. Other suitable conditions include in the absence of impurities, such as metals or other materials that would hinder the reaction from progression.

As used herein, "catalyst" refers to a substance that initiates or accelerates a chemical reaction without itself being affected or consumed in the reaction. Examples of useful catalysts include metal catalysts. In certain embodiments, the catalyst lowers the temperature for initiation of thermal decomposition and increases the rate of thermal decomposition at certain pyrolysis temperatures (e.g., about 200° C. to about 325° C.).

In some embodiments, the catalyst is a chloride, oxide, hydroxide, nitrate, phosphate, sulphonate, carbonate or stearate compound containing a metal ion. Examples of suitable metal ions include aluminum, antimony, barium, bismuth, cadmium, calcium, cerium, chromium, cobalt, copper, gallium, iron, lanthanum, lead, lithium, magnesium, molybdenum, nickel, palladium, potassium, silver, sodium, strontium, tin, tungsten, vanadium or zinc and the like. In some embodiments, the catalyst is an organic catalyst that is an amine, azide, enol, glycol, quaternary ammonium salt, phenoxide, cyanate, thiocyanate, dialkyl amide and alkyl thiolate. In some embodiments, the catalyst is calcium hydroxide. In other embodiments, the catalyst is sodium carbonate. Mixtures of two or more catalysts are also included.

In certain embodiments, the amount of metal catalyst is about 0.1% to about 15% or about 1% to about 25%, or 4% to about 50%, or about 4% to about 50% based on the weight of metal ion relative to the dry solid weight of the biomass. In some embodiments, the amount of catalyst is between about 7.5% and about 12%. In other embodiments, the amount of catalyst is about 0.5% dry cell weight, about 1%, about 2%, about 3%, about 4%, about 5, about 6%, about 7%, about 8%, about 9%, or about 10%, or about 11%, or about 12%, or about 13%, or about 14%, or about 15%, or about 20%, or about 30%, or about 40% or about 50% or amounts in between these.

As used herein, the term "sufficient amount" when used in reference to a chemical reagent in a reaction is intended to mean a quantity of the reference reagent that can meet the demands of the chemical reaction and the desired purity of the product.

Thermal Degradation of the P4HB Biomass

"Heating," "pyrolysis", "thermolysis" and "torrefying" as used herein refer to thermal degradation (e.g., decomposition) of the P4HB biomass for conversion to GBL. In general, the thermal degradation of the P4HB biomass occurs at an elevated temperature in the presence of a catalyst. For example, in certain embodiments, the heating temperature for the processes described herein is between about 200° C. to about 400° C. In some embodiments, the heating temperature is about 200° C. to about 350° C. In other embodiments, the heating temperature is about 300° C. "Pyrolysis" typically refers to a thermochemical decomposition of the biomass at elevated temperatures over a period of time. The duration can range from a few seconds to hours. In certain conditions, pyrolysis occurs in the absence of oxygen or in the presence of a limited amount of oxygen to avoid oxygenation. The processes for P4HB biomass pyrolysis can include direct heat transfer or indirect heat transfer. "Flash pyrolysis" refers to quickly heating the biomass at a high temperature for fast decomposition of the P4HB biomass, for example, depolymerization of a P4HB in the biomass. Another example of flash pyrolysis is RTP™ rapid thermal pyrolysis. RTP™ technology and equipment from Envergent Technologies, Des Plaines, Ill. converts feedstocks into bio-oil. "Torrefying" refers to the process of torrefaction, which is an art-recognized term that refers to the drying of biomass at elevated temperature with loss of water and organic volatiles to produce a torrefied biomass with enhanced solid fuel properties. The torrefied biomass typically has higher heating value, greater bulk density, improved grindability for pulverized fuel boilers, increased mold resistance and reduced moisture sensitivity compared to biomass dried to remove free water only (e.g. conventional oven drying at 105° C.). The torrefaction process typically involves heating a biomass in a temperature range from 200-350° C., over a relatively long duration (e.g., 10-30 minutes), typically in the absence of oxygen.

The process results for example, in a torrefied biomass having a water content that is less than 7 wt % of the biomass. The torrefied biomass may then be processed further. In some embodiments, the heating is done in a vacuum, at atmospheric pressure or under controlled pressure. In certain embodiments, the heating is accomplished without the use or with a reduced use of petroleum generated energy.

In certain embodiments, the P4HB biomass is dried prior to heating. Alternatively, in other embodiments, drying is done during the thermal degradation (e.g., heating, pyrolysis or torrefaction) of the P4HB biomass. Drying reduces the water content of the biomass. In certain embodiments, the biomass is dried at a temperature of between about 100° C. to about 350° C., for example, between about 200° C. and about 275° C. In some embodiments, the dried 4PHB biomass has a water content of 5 wt %, or less.

In certain embodiments, the heating of the P4HB biomass/catalyst mixture is carried out for a sufficient time to efficiently and specifically convert the P4HB biomass to GBL. In certain embodiments, the time period for heating is from about 30 seconds to about 1 minute, from about 30 seconds to about 1.5 minutes, from about 1 minute to about 10 minutes, from about 1 minute to about 5 minutes or a time between, for example, about 1 minute, about 2 minutes, about 1.5 minutes, about 2.5 minutes, about 3.5 minutes.

In other embodiments, the time period is from about 1 minute to about 2 minutes. In still other embodiments, the heating time duration is for a time between about 5 minutes and about 30 minutes, between about 30 minutes and about 2 hours, or between about 2 hours and about 10 hours or for greater that 10 hours (e.g., 24 hours).

In certain embodiments, the heating temperature is at a temperature of about 200° C. to about 350° C. including a temperature between, for example, about 205° C., about 210° C., about 215° C., about 220° C., about 225° C., about 230° C., about 235° C., about 240° C., about 245° C., about 250° C., about 255° C. about 260° C., about 270° C., about 275° C., about 280° C., about 290° C., about 300° C., about 310° C., about 320° C., about 330° C., about 340° C., or 345° C. In certain embodiments, the temperature is about 250° C. In certain embodiments, the temperature is about 275° C. In other embodiments, the temperature is about 300° C.

In certain embodiments, the process also includes flash pyrolyzing the residual biomass for example at a temperature of 500° C. or greater for a time period sufficient to decompose at least a portion of the residual biomass into pyrolysis liquids. In certain embodiments, the flash pyrolyzing is conducted at a temperature of 500° C. to 750° C. In some embodiments, a residence time of the residual biomass in the flash pyrolyzing is from 1 second to 15 seconds, or from 1 second to 5 seconds or for a sufficient time to pyrolyze the biomass to generate the desired pyrolysis precuts, for example, pyrolysis liquids. In some embodiments, the flash pyrolysis can take place instead of torrefaction. In other embodiments, the flash pyrolysis can take place after the torrrefication process is complete.

As used herein, "pyrolysis liquids" are defined as a low viscosity fluid with up to 15-20% water, typically containing sugars, aldehydes, furans, ketones, alcohols, carboxylic acids and lignins. Also known as bio-oil, this material is produced by pyrolysis, typically fast pyrolysis of biomass at a temperature that is sufficient to decompose at least a portion of the biomass into recoverable gases and liquids that may solidify on standing. In some embodiments, the temperature that is sufficient to decompose the biomass is a temperature between 400° C. to 800° C.

In certain embodiments, "recovering" the gamma-butyrolactone vapor includes condensing the vapor. As used herein, the term "recovering" as it applies to the vapor means to isolate it from the P4HB biomass materials, for example including but not limited to: recovering by condensation, separation methodologies, such as the use of membranes, gas (e.g., vapor) phase separation, such as distillation, and the like. Thus, the recovering may be accomplished via a condensation mechanism that captures the monomer component vapor, condenses the monomer component vapor to a liquid form and transfers it away from the biomass materials.

As a non-limiting example, the condensing of the gamma-butyrolactone vapor may be described as follows. The incoming gas/vapor stream from the pyrolysis/torrefaction chamber enters an interchanger, where the gas/vapor stream may be pre-cooled. The gas/vapor stream then passes through a chiller where the temperature of the gas/vapor stream is lowered to that required to condense the designated vapors from the gas by indirect contact with a refrigerant. The gas and condensed vapors flow from the chiller into a separator, where the condensed vapors are collected in the bottom. The gas, free of the vapors, flows from the separator, passes through the Interchanger and exits the unit. The recovered liquids flow, or are pumped, from the bottom of the separator to storage. For some of the products, the condensed vapors solidify and the solid is collected.

In certain embodiments, recovery of the catalyst is further included in the processes of the invention. For example, when a calcium catalyst is used calcination is a useful recovery technique. Calcination is a thermal treatment process that is carried out on minerals, metals or ores to change the materials through decarboxylation, dehydration, devolatilization of organic matter, phase transformation or oxidation. The process is normally carried out in reactors such as hearth furnaces, shaft furnaces, rotary kilns or more recently fluidized beds reactors. The calcination temperature is chosen to be below the melting point of the substrate but above its decomposition or phase transition temperature. Often this is taken as the temperature at which the Gibbs free energy of reaction is equal to zero. For the decomposition of CaCO₃ to CaO, the calcination temperature at ΔG=0 is calculated to be ~850° C. Typically for most minerals, the calcination temperature is in the range of 800-1000° C. but calcinations can also refer to heating carried out in the 200-800° C. range.

To recover the calcium catalyst from the biomass after recovery of the GBL, one would transfer the spent biomass residue directly from pyrolysis or torrefaction into a calcining reactor and continue heating the biomass residue in air to 825-850° C. for a period of time to remove all traces of the organic biomass. Once the organic biomass is removed, the catalyst could be used as is or purified further by separating the metal oxides present (from the fermentation media and catalyst) based on density using equipment known to those in the art.

In certain embodiments, the process is selective for producing gamma-butyrolactone product with a relatively small amount of undesired side products (e.g., dimerized product of GBL (3-(dihydro-2(3H)-furanylidene)dihydro-2(3H)-furanone), other oligomers of GBL or other side products). For example, in some embodiments the use of a specific catalyst in a sufficient amount will reduce the production of undesired side products and increase the yield of gamma-butyrolactone by at least about 2 fold. In some embodiments, the production of undesired side products will be reduced to at least about 50%, at least about 40%, at least about 30%, at least about 20% at least about 10%, or at least about 5%. In certain embodiment, the undesired side products will be less than about 5% of the recovered gamma-butyrolactone, less than about 4% of the recovered gamma-butyrolactone, less than about 3% of the recovered gamma-butyrolactone, less than about 2% of the recovered gamma-butyrolactone, or less than about 1% of the recovered gamma-butyrolactone.

The processes described herein can provide a yield of GBL express as a percent yield, for example, when grown from glucose as a carbon source, the yield is up to 95% based gram GBL recovered per gram P4HB contained in the biomass feed to the process (reported as percent). In other embodiments, the yield is in a range between about 40% and about 95%, for example between about 50% and about 70%, or between about 60% and 70%. In other embodiment, the yield is about 75%, about 70%, about 65%, about 60%, about 55%, about 50%, about 45% or about 40%.

As used herein, "gamma-butyrolactone" or GBL refers to the compound with the following chemical structure:

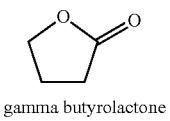

gamma butyrolactone

The term "gamma-butyrolactone product" refers to a product that contains at least about 70 up to 100 weight percent gamma-butyrolactone. For example, in a certain embodiment, the gamma-butyrolactone product may contain 95% by weight gamma-butyrolactone and 5% by weight side products. In some embodiments, the amount of gamma-butyrolactone in the gamma-butyrolactone product is about 71% by weight, about 72% by weight, about 73% by weight, about, 74% by weight, about 75% by weight, about 76% by weight, about 77% by weight, about 78% by weight, about 79% by weight, about 80% by weight, 81% by weight, about 82% by weight, about 83% by weight, about, 84% by weight, about 85% by weight, about 86% by weight, about 87% by weight, about 88% by weight, about 89% by weight, about 90% by weight, 91% by weight, about 92% by weight, about 93% by weight, about, 94% by weight, about 95% by weight, about 96% by weight, about 97% by weight, about 98% by weight, about 99% by weight or about 100% by weight. In particular embodiments, the weight percent of gamma-butyrolactone product produced by the processes described herein is 85% or greater than 85%.

In other embodiments, the gamma-butyrolactone product can be further purified if needed by additional methods known in the art, for example, by distillation, by reactive distillation (e.g., the gamma-butryolactone product is acidified first to oxidize certain components (e.g., for ease of separation) and then distilled) by treatment with activated carbon for removal of color and/or odor bodies, by ion exchange treatment, by liquid-liquid extraction—with GBL immiscible solvent (e.g., nonpolar solvents, like cyclopentane or hexane) to remove fatty acids etc, for purification after GBL recovery, by vacuum distillation, by extraction distillation or using similar methods that would result in further purifying the gamma-butyrolactone product to increase the yield of gamma-butyrolactone. Combinations of these treatments can also be utilized.

In certain embodiments, GBL is further chemically modified and/or substituted to other four carbon products (4C products) and derivatives including but not limited to succinic acid, 1,4-butanediamide, succinonitrile, succinamide, N-vinyl-2-pyrrolidone (NVP), 2-pyrrolidone (2-Py), N-methyl-2-pyrrolidone (NMP), tetrahydrofuran (THF), 1,4-butanediol (BDO). Methods and reactions for production of these derivatives from gamma-butyrolactone are readily known by one skilled in the art.

As used herein, the term "residual biomass" refers to the biomass after PHA conversion to the small molecule intermediates. The residual biomass may then be converted via torrefaction to a useable, fuel, thereby reducing the waste from PHA production and gaining additional valuable commodity chemicals from typical torrefaction processes. The torrefaction is conducted at a temperature that is sufficient to densify the residual biomass. In certain embodiments, processes described herein are integrated with a torrefaction process where the residual biomass continues to be thermally treated once the volatile chemical intermediates have been released to provide a fuel material. Fuel materials produced by this process are used for direct combustion or further treated to produce pyrolysis liquids or syngas. Overall, the process has the added advantage that the residual biomass is converted to a higher value fuel which can then be used for the production of electricity and steam to provide energy for the process thereby eliminating the need for waste treatment.

A "carbon footprint" is a measure of the impact the processes have on the environment, and in particular climate change. It relates to the amount of greenhouse gases produced.

In certain embodiments, it may be desirable to label the constituents of the biomass. For example, it may be useful to deliberately label with an isotope of carbon (e.g., $^{13}C$) to facilitate structure determination or for other means. This is achieved by growing microorganisms genetically engineered to express the constituents, e.g., polymers, but instead of the usual media, the bacteria are grown on a growth medium with $^{13}C$-containing carbon source, such as glucose, pyruvic acid, etc. In this way polymers can be produced that are labeled with $^{13}C$ uniformly, partially, or at specific sites. Additionally, labeling allows the exact percentage in bioplastics that came from renewable sources (e.g., plant derivatives) can be known via ASTM D6866—an industrial application of radiocarbon dating. ASTM D6866 measures the Carbon 14 content of biobased materials; and since fossil-based materials no longer have Carbon 14, ASTM D6866 can effectively dispel inaccurate claims of biobased content

EXAMPLES

The present technology is further illustrated by the following examples, which should not be construed as limiting in any way.

Experimental Methods

Measurement of Thermal Degradation Behavior by Thermogravimetric Analysis (TGA)

The isothermal weight loss versus time for biomass samples was measured using a TA Instruments Q500 Thermogravimetric Analyzer (TGA). TGA is a technique commonly used to measure the thermal degradation behavior of materials such as PHA's. The instrument consists of a sensitive balance from which a sample is suspended. A furnace is then brought up around the sample and programmed to heat at a specified rate (ramp conditions) or to a certain temperature and hold (isothermal conditions). A purge gas is swept across the sample during heating which is typically nitrogen or air. As the sample is heated, it begins to lose weight which is recorded by the balance. At the end of the analysis, the results can then be plotted as percent sample weight loss versus temperature or time. When plotted as weight loss versus time, the rate of degradation can then be determined from the slope of this curve. For the following examples, 5-10 mg of dry biomass was weighed into a platinum pan and then loaded onto the TGA balance. The purge gas used was nitrogen at a flow rate of 60 ml/min. For isothermal test conditions, the biomass sample was preheated from room temperature to the programmed isothermal temperature at a heating rate of 150-200° C./min and held at the isothermal temperature for 10-30 min. The data was then plotted as % sample weight loss vs. time and the thermal degradation rate calculated from the initial slope of the curve.

Measurement of Thermal Degradation Products by Pyrolysis-Gas Chromatography-Mass Spectroscopy (Py-GC-MS).

In order to identify and semi-quantitate the monomer compounds generated from dry biomass while being heated at various temperatures, an Agilent 7890A/5975 GC-MS equipped with a Frontier Lab PY-2020iD pyrolyzer was used. For this technique, a sample is weighed into a steel cup and loaded into the pyrolyzer autosampler. When the pyrolyzer and GC-MS are started, the steel cup is automatically placed into the pyrolyzer which has been set to a specific temperature. The sample is held in the pyrolyzer for a short period of time while volatiles are released by the sample. The volatiles are then swept using helium gas into the GC column where they condense onto the column which is at room temperature. Once the pyrolysis is over, the GC column is heated at a certain rate in order to elute the volatiles released from the sample. The volatile compounds are then swept using helium gas into an electro ionization/mass spectral detector (mass range 10-700 daltons) for identification and quantitation.

For the following examples, 200-400 µg of dry biomass was weighed into a steel pyrolyzer cup using a microbalance. The cup was then loaded into the pyrolyzer autosampler. The pyrolyzer was programmed to heat to temperatures ranging from 225-350° C. for a duration of 0.2-1 minutes. The GC column used in the examples was either a Frontier Lab Ultra Alloy capillary column or an HP-5MS column (length 30 m, ID 0.25 µm, film thickness 0.25 µm). The GC was then programmed to heat from room temperature to 70° C. over 5 minutes, then to 240° C. at 10° C./min for 4 min. and finally to 270° C. at 20° C./min for 1.5 min. Total GC run time was 25 minutes. Peaks showing in the chromatogram were identified by the best probability match to spectra from a NIST mass spectral library. GBL 'purity' was measured by taking the area counts for GBL peak and dividing it by the area counts for GBL dimer peak.

These examples describe a number of biotechnology tools and methods for the construction of strains that generate a product of interest. Suitable host strains, the potential source and a list of recombinant genes used in these examples, suitable extrachromosomal vectors, suitable strategies and regulatory elements to control recombinant gene expression, and a selection of construction techniques to overexpress genes in or inactivate genes from host organisms are described. These biotechnology tools and methods are well known to those skilled in the art.

Example 1

4HB Polymer Production Before Modification

This example shows the 4HB polymer production capability of microbial strains have not been optimized to incorporate high mole % 4HB from renewable carbon resources. The strains used in this example are listed in Table 2. Strains 1 and 2 were described by Dennis and Valentin (U.S. Pat. No. 6,117,658).

TABLE 2

Strains used in Example 1

| Strains | Relevant host genome modifications | Genes overexpressed |
|---|---|---|
| 1 | | $P_{lac}$-phaCAB |
| | | $P_{lac}$-orfZ-'cat1-sucD-4hbD |
| 2 | yneI-negative | $P_{lac}$-phaCAB |
| | | $P_{lac}$-orfZ-'cat1-sucD-4hbD |
| 3 | ΔyneI ΔgabD | $P_x$-phaC, $P_{12}$-phaAB |
| | | $P_{lac}$-orfZ-'cat1-sucD-4hbD |

Strain 3 contained deletions of both the yneI and gabD chromosomal genes (FIG. 1 and Table 1A, Reaction Number 12) which encode the CoA-independent, NAD-dependent succinate semialdehyde (SSA) dehydrogenase and the CoA-independent, NADP-dependent SSA dehydrogenase, respectively. To accomplish this, a derivative strain of LS5218 (Jenkins and Nunn J. Bacteriol. 169:42-52 (1987)) was used that expressed phaA, phaB and phaC as described previously by Huisman et al. (U.S. Pat. No. 6,316,262). Single null gabD and yneI mutants were constructed as described by Farmer et al. (WO Patent No. 2010/068953) and used the Red/ET recombineering method described by Datsenko and Wanner (*Proc. Natl. Acad. Sci. USA.* 97:6640-6645 (2000)), a method well known to those skilled in the art. This resulted in strain 3 that had the entire coding sequences of both the yneI and gabD genes removed from the genome. Note that strains 1, 2, and 3 contain the same gene cassette $P_{lac}$-orfZ-'cat1-sucD-4hbD as described by Dennis and Valentin, where sucD is not codon-optimized for expression in *E. coli*.

To examine production of P3HB-co-4HB (poly-3-hydroxybutyrate-co-4-hydroxybutyrate), strain 3 was cultured overnight in a sterile tube containing 3 mL of LB and appropriate antibiotics. From this, 50 μL was added in triplicate to Duetz deep-well plate wells containing 450 μL of LB and antibiotics. This was grown for 6 hours at 30° C. with shaking. Then, 25 μL of each LB culture replicate was added to 3 additional wells containing 475 μL of LB medium supplemented with 10 g/L glucose, 100 μM IPTG, 100 μg/mL ampicillin, and 25 μg/mL chloramphenicol, and incubated at 30° C. with shaking for 72 hours. Thereafter, production well sets were combined (1.5 mL total) and analyzed for polymer content. At the end of the experiment, cultures were spun down at 4150 rpm, washed once with distilled water, frozen at −80° C. for at least 30 minutes, and lyophilized overnight. The next day, a measured amount of lyophilized cell pellet was added to a glass tube, followed by 3 mL of butanolysis reagent that consists of an equal volume mixture of 99.9% n-butanol and 4.0 N HCl in dioxane with 2 mg/mL diphenylmethane as internal standard. After capping the tubes, they were vortexed briefly and placed on a heat block set to 93° C. for six hours with periodic vortexing. Afterwards, the tube was cooled down to room temperature before adding 3 mL distilled water. The tube was vortexed for approximately 10 s before spinning down at 620 rpm (Sorvall Legend RT benchtop centrifuge) for 2 min. 1 mL of the organic phase was pipetted into a GC vial, which was then analyzed by gas chromatography-flame ionization detection (GC-FID) (Hewlett-Packard 5890 Series H). The quantity of PHA in the cell pellet was determined by comparing against a standard curve for 4HB (for P4HB analysis) or by comparing against standard curves for both 3HB and 4HB (for PHB-co-4HB analysis). The 4HB standard curve was generated by adding different amounts of a 10% solution of γ-butyrolactone (GBL) in butanol to separate butanolysis reactions. The 3HB standard curve was generated by adding different amounts of 99% ethyl 3-hydroxybutyrate to separate butanolysis reactions.

The results in Table 3 show that strain 3 incorporated similarly low mole % 4HB into the copolymer as was described in U.S. Pat. No. 6,117,658.

TABLE 3

P3HB-co-4HBpolymer production from microbial strains

| Strains | Mole % 3HB | Mole % 4HB |
|---|---|---|
| 1 | 98.5 | 1.5 |
| 2 | 95.0 | 5.0 |
| 3 | 97.6 ± 0.9 | 2.4 ± 0.9 |

Example 2

P4HB Production Via an α-Ketoglutarate Decarboxylase or a Succinyl-CoA dehydrogenase Several metabolic pathways were proposed to generate succinic semialdehyde (SSA) from the tricarboxylic acid (TCA) cycle (reviewed by Steinbüchel and Lütke-Eversloh, *Biochem. Engineering J.* 16:81-96 (2003) and Efe et al., *Biotechnology and Bioengineering* 99:1392-1406 (2008). One pathway converts succinyl-CoA to SSA via a succinyl-CoA dehydrogenase, which is encoded by sucD (Söhling and Gottschalk, *J. Bacteriol.* 178:871-880 (1996); FIG. 1, Reaction number 7). A second pathway converts alpha-ketoglutarate to SSA via an alpha-ketoglutarate decarboxylase that is encoded by kgdM (Tian et al. *Proc. Natl. Acad. Sci. U.S.A.* 102:10670-10675 (2005); FIG. 1, Reaction number 8). A third pathway converts alpha-ketoglutarate to SSA via L-glutamate and 4-aminobutyrate using a glutamate dehydrogenase (EC 1.4.1.4), a glutamate decarboxylase (EC 4.1.1.15), and a 4-aminobutyrate transaminase (EC 2.6.1.19), or a 4-aminobutyrate aminotransferase (EC 2.6.1.19). Van Dien et al. (WO Patent No. 2010/141920) showed that both the sucD and the kgdM pathways worked independently of each other and were additive when combined to produce 4HB. Note that kgdM is called sucA in van Dien et al.

In this example, the two metabolic pathways via sucD or kgdM were compared to see which one could produce the highest P4HB titers. The following three strains were thus constructed using the well known biotechnology tools and methods described above, all of which contained chromosomal deletions of yneI and gabD and overexpressed a PHA synthase, and a CoA transferase, and either an alpha-ketoglutarate decarboxylase with an SSA reductase (strain 5), or a succinyl-CoA dehydrogenase with an SSA reductase (strain 6). Strain 4 served as a negative control and just contained the empty vector instead of $P_{trc}$-kgdM-ssa$R_{At}$* or $P_{trc}$-sucD*-ssa$R_{At}$* (see Table 4).

TABLE 4

Microbial Strains used in Example 2

| Strains | Relevant host genome modifications | Genes overexpressed |
|---|---|---|
| 4 | ΔyneI ΔgabD | $P_{rpsU}$-orfZ; $P_{syn1}$-phaC1 |
| 5 | ΔyneI ΔgabD | $P_{rpsU}$-orfZ; $P_{syn1}$-phaC1; $P_{trc}$-kgdM-ssa$R_{At}$* |
| 6 | ΔyneI ΔgabD | $P_{rpsU}$-orfZ; $P_{syn1}$-phaC1; $P_{trc}$-sucD*-ssa$R_{At}$* |

The strains were grown in a 24 hour shake plate assay. The production medium consisted of 1×E2 minimal salts solution containing 10 g/L glucose, 5 g/L sodium 4-hydroxybutyrate, 2 mM $MgSO_4$, 1× Trace Salts Solution, and 100 μM IPTG. 50×E2 stock solution consists of 1.275 M $NaNH_4HPO_4.4H_2O$, 1.643 M $K_2HPO_4$, and 1.36 M $KH_2PO_4$. 1000× stock Trace Salts Solution is prepared by adding per 1 L of 1.5 N HCL: 50 g $FeSO_4.7H_2O$, 11 g $ZnSO_4.7H_2O$, 2.5 g $MnSO_4.4H_2O$, 5 g $CuSO_4.5H_2O$, 0.5 g $(NH_4)_6Mo_7O_{24}.4H_2O$, 0.1 g $Na_2B_4O_7$, and 10 g $CaCl_2.2H_2O$. At the end of the growth phase, the biomass and P4HB titers were determined as described in Example 1.

The results in Table 5 surprisingly show that only strain 6 expressing the sucD pathway produced significant amounts of P4HB. In contrast to the strains described by van Dien et al. (WO Patent No. 2010/141920) that produced 4HB via both the kgdM and sucD pathways in similar amounts, the alpha-ketoglutarate decarboxylase pathway used here produced only very low amounts of P4HB.

TABLE 5

Biomass and P4HB titer

| Strains | Biomass Titer (g/L) | P4HB Titer (% dcw) |
|---|---|---|
| 4 | 2.33 ± 0.02 | 0.0 ± 0.0 |
| 5 | 2.06 ± 0.03 | 0.1 ± 0.0 |
| 6 | 2.59 ± 0.01 | 6.9 ± 0.1 |

Example 3

Improvement in P(4HB) Production by Overexpressing Certain Succinic Semialdehyde Reductase Genes Effect of 4hbd on P4HB Production The succinic semialdehyde (SSA) reductase gene 4hbD was used by Dermis and Valentin (U.S. Pat. No. 6,117,658) to produce P3HB-co-4HB copolymer. To see how effective overproduction of this SSA reductase was for P4HB homopolymer production, the 4hbD gene was overexpressed by the IPTG-inducible $P_{trc}$ promoter (strain 8). An empty vector containing strain served as a control (strain 7). The host strain used contained chromosomal deletions of genes yneI and gabD and also overexpressed the recombinant genes orfZ, sucD* and phaC3/C1* as shown in Table 6.

TABLE 6

Microbial Strains used in this section of Example 3

| Strains | Relevant host genome modifications | Genes overexpressed |
|---|---|---|
| 7 | ΔyneI ΔgabD | $P_{rpsU}$-orfZ, $P_{uspA}$-phaC3/C1*-sucD* |
| 8 | ΔyneI ΔgabD | $P_{rpsU}$-orfZ, $P_{uspA}$-phaC3/C1*-sucD*, $P_{trc}$-4hbD |

The strains were grown in a 48 hour shake plate assay. The production medium consisted of 1×E2 minimal salts solution containing 20 g/L glucose, 1× Trace Salts Solution and 100 μM IPTG. Both E2 medium and trace elements are described in Example 2. At the end of the growth phase, the biomass and P4HB titers were determined as described in Example 1.

As shown in Table 7, strain 8 expressing 4hbD incorporated low amounts of 4HB into the polymer, similar to the strains described in U.S. Pat. No. 6,117,658 and verified in Example 1. However, very unexpectedly, the empty vector control strain 7, which did not express the 4hbd gene, produced significantly increased P4HB titers.

TABLE 7

Biomass and P4HB titer for microbial strains 7 and 8

| Strains | Biomass Titer (g/L) | P4HB Titer (% dcw) |
|---|---|---|
| 7 | 2.64 ± 0.04 | 17.09 ± 0.06 |
| 8 | 4.20 ± 0.09 | 3.17 ± 0.24 |

Effect of Other SSA Reductase Genes on P4HB Production

Since the 4hbD-encoded SSA reductase unexpectedly did not produce higher amounts of P4HB than its parental strain, another known SSA reductase from *Arabidopsis thaliana* (Breitkreuz et al., J. Biol. Chem. 278:41552-41556 (2003)) was cloned in search of a catalytically more active enzyme. In addition, several genes whose protein sequences were found to be homologous to the *A. thaliana* enzyme were tested. These included putative SSA reductase genes from *Mus musculus* and *Aspergillus terreus*. Furthermore, to investigate if an unspecific aldehyde dehydrogenase from *E. coli* that did not show significant homology to the *Arabidopsis* enzyme could catalyze the SSA to 4HB reaction, gene yqhD was also cloned. YqhD was shown previously to have a catalytic activity to convert 3-hydroxypropionaldehyde to 1,3-propanediol (Emptage et al., U.S. Pat. No. 7,504,250). The resulting strains are listed in Table 8.

TABLE 8

Microbial strains used in Example 3

| Strains | Relevant host genome modifications | Genes overexpressed |
|---|---|---|
| 9 | ΔyneI ΔgabD | $P_{rpsU}$-orfZ, $P_{uspA}$-phaC3/C1*-sucD* |
| 10 | ΔyneI ΔgabD | $P_{rpsU}$-orfZ, $P_{uspA}$-phaC3/C1*-sucD*, $P_{trc}$-ssaR$_{At}$* |
| 11 | ΔyneI ΔgabD | $P_{rpsU}$-orfZ, $P_{uspA}$-phaC3/C1*-sucD*, $P_{trc}$-ssaR$_{Mm}$* |
| 12 | ΔyneI ΔgabD | $P_{rpsU}$-orfZ, $P_{uspA}$-phaC3/C1*-sucD*, $P_{trc}$-ssaR$_{At2}$* |
| 13 | ΔyneI ΔgabD | $P_{rpsU}$-orfZ, $P_{uspA}$-phaC3/C1*-sucD*, $P_{trc}$-yqhD |

Strains 9 to 13 were grown and the biomass and P4HB titers were determined as described above. Table 9 shows that unlike the 4hbD-encoded SSA reductase, overproduction of the SSA reductase from *A. thaliana* significantly increased P4HB production. This clearly illustrates how unpredictable the metabolic engineering outcome is albeit the known function of both the *C. kluyveri* and *A. thaliana* enzymes. The putative SSA reductase genes from *M. musculus* and *A. terreus* also improved P4HB production to various degrees. Unexpectedly, the unspecific *E. coli* aldehyde dehydrogenase YqhD increased P4HB production to a similar degree as was observed for the *A. thaliana* SSA reductase.

TABLE 9

Biomass and P4HB titer for microbial strains 9-13

| Strains | Biomass Titer (g/L) | P4HB Titer (% dcw) |
|---|---|---|
| 9 | 2.64 ± 0.04 | 17.09 ± 0.06 |
| 10 | 4.80 ± 0.12 | 28.46 ± 0.65 |
| 11 | 3.96 ± 0.79 | 23.31 ± 4.32 |

TABLE 9-continued

Biomass and P4HB titer for microbial strains 9-13

| Strains | Biomass Titer (g/L) | P4HB Titer (% dcw) |
|---|---|---|
| 12 | 3.60 ± 0.29 | 19.74 ± 0.43 |
| 13 | 5.07 ± 0.07 | 27.99 ± 1.36 |

Example 4

Improved P4HB Production by Deletion of Pyruvate Kinases

Removal of pyruvate kinase I encoded by pykF and pyruvate kinase II encoded by pykA (FIG. 1, Reaction number 2) has been shown to reduce the production of acetate and favor the generation of $CO_2$ (Zhu et al. (2001) *Biotechnol. Prog.* 17:624-628). These results indicate that removal of pykF and pykA causes carbon flux to be diverted to the TCA cycle, and so these genetic modifications have been described as being useful for the microbial production of succinate and 1,4-butanediol (Park et al., WO Patent No. 2009/031766). To determine if deleting the pyruvate kinase genes pykF and pykA would lead to improved P4HB titers, the following two strains were constructed using the well known biotechnology tools and methods described above. Both of these strains contained chromosomal deletions of yneI and gabD and overexpressed a PHA synthase, a succinyl-CoA dehydrogenase, an SSA reductase and a CoA-transferase. Strain 14 retained its native unmodified copies of pykF and pykA on the chromosome, while strain 15 has both of these genes removed (Table 10).

TABLE 10

Microbial strains used in Example 4

| Strains | Relevant host genome modifications | Genes overexpressed |
|---|---|---|
| 14 | ΔyneI ΔgabD | $P_{syn1}$-phaC1-$P_{uspA}$-sucD*-ssaR$_{At}$*; $P_{rpsU}$-orfZ |
| 15 | ΔyneI ΔgabD ΔpykF ΔpykA | $P_{syn1}$-phaC1-$P_{uspA}$-sucD*-ssaR$_{At}$*; $P_{rpsU}$-orfZ |

The strains were grown in a 48 hour shake plate assay. The production medium consisted of 1×E2 minimal salts solution containing 30 g/L glucose and 1× Trace Salts Solution. Both E2 medium and trace elements are described in Example 2. At the end of the growth phase, the biomass and P4HB titers were determined as described in Example 1.

The results in Table 11 show that strain 15 which lacks pykF and pykA produced more P4HB than strain 14 that retained these two genes.

TABLE 11

Biomass and P4HB titer for microbial strains 14 and 15.

| Strain | Biomass Titer (g/L) | P4HB Titer (% dew) |
|---|---|---|
| 14 | 10.26 ± 0.44 | 25.6 ± 4.8 |
| 15 | 14.17 ± 0.11 | 46.3 ± 2.2 |

Example 5

Improved P4HB Production by Overexpression of PEP Carboxylase

Overexpression of PEP carboxylase (FIG. 1, Reaction number 3) has been used to enhance the production of both the aspartate family of amino acids and succinate by increasing carbon flow into the TCA cycle. However, since many wild-type homologues of PEP carboxylase are feedback-regulated by L-aspartate or other TCA cycle-derived metabolites, a considerable amount of prior art has been created regarding the identification of either feedback-desensitized mutants (Sugimoto et al., U.S. Pat. No. 5,876,983; San et al., US Patent No. 2005/0170482) or alternative homologues that naturally exhibit less allosteric regulation (Rayapati and Crafton, US Patent No. 2002/0151010). To determine whether overexpression of PEP carboxylase would lead to improved P4HB titer, the following three strains were constructed using the well known biotechnology tools and methods described above. These strains contained chromosomal deletions of yneI and gabD and overexpressed a PHA synthase, a succinyl-CoA dehydrogenase, an SSA reductase, a CoA-transferase, and either wild-type PEP carboxylase ($ppc_{Ec}$) from *E. coli* (strain 17) or wild-type PEP carboxylase ($ppc_{Ms}$) from *Medicago sativa* (strain 18) which has reduced allosteric regulation (Rayapati and Crafton, US20020151010 A1). Strain 16 served as a negative control and contained only an empty vector instead of $P_{syn1}$-$ppc_{Ec}$ or $P_{syn1}$-$ppc_{Ms}$ (Table 12).

TABLE 12

Microbial strains used in Example 5

| Strains | Relevant host genome modifications | Genes overexpressed |
|---|---|---|
| 16 | ΔyneI ΔgabD | $P_{syn1}$-phaC1-$P_{uspA}$-sucD*-ssaR$_{At}$*; $P_{rpsU}$-orfZ |
| 17 | ΔyneI ΔgabD | $P_{syn1}$-phaC1-$P_{uspA}$-sucD*-ssaR$_{At}$*; $P_{rpsU}$-orfZ; $P_{syn1}$-$ppc_{Ec}$ |
| 18 | ΔyneI ΔgabD | $P_{syn1}$-phaC1-$P_{uspA}$-sucD*-ssaR$_{At}$*; $P_{rpsU}$-orfZ; $P_{syn1}$-$ppc_{Ms}$* |

The strains were grown in a 44 hour shake plate assay. The production medium consisted of 1×E2 minimal salts solution containing 25 g/L glucose and 1× Trace Salts Solution. Both E2 medium and trace elements are described in Example 2. At the end of the growth phase, the biomass and P4HB titers were determined as described in Example 1.

The results in Table 13 show that both strains 17 and 18, which express either wild-type *E. coli* PEP carboxylase or a less-regulated homologue thereof, produced significantly higher amounts of P4HB than control strain 16.

TABLE 13

Biomass and P4HB titer for microbial strains 16, 17 and 18.

| Strains | Biomass Titer (g/L) | P4HB Titer (% dcw) |
|---|---|---|
| 16 | 2.31 ± 0.01 | 14.93 ± 0.83 |
| 17 | 2.85 ± 0.29 | 25.57 ± 1.59 |
| 18 | 3.02 ± 0.13 | 24.31 ± 0.65 |

Example 6

Improved P4HB Production by Deleting Malic Enzymes

*E. coli* possesses two isoforms of malic enzyme which require either $NAD^+$ (maeA) or $NADP^+$ (maeB) as reducing cofactor (Bologna et al., *J. Bacteriol.* 189(16):5937-5946 (2007) for the reversible conversion of malate to pyruvate (FIG. 1, Reaction number 4). Deletion of both maeA and maeB has been shown to enhance the production of L-lysine and L-threonine in *E. coli*, presumably by preventing the loss of carbon from the TCA cycle (van Dien et al., WO Patent No. 2005/010175). To determine if deleting both malic enzymes would also lead to improved P4HB titers, the following two strains were constructed using the well known biotechnology tools and methods described above. Both of these strains contained chromosomal deletions of yneI and gabD and overexpressed a PHA synthase, a succinyl-CoA dehydrogenase, an SSA reductase and a CoA-transferase. Strain 19 retained its native unmodified copies of maeA and maeB on the chromosome, while strain 20 has both of these genes removed (Table 14).

TABLE 14

Microbial strains used in Example 6

| Strains | Relevant host genome modifications | Genes overexpressed |
|---|---|---|
| 19 | ΔyneI ΔgabD | $P_{synI}$-phaC1-$P_{uspA}$-sucD*-ssaR$_{At}$*; $P_{rpsU}$-orfZ |
| 20 | ΔyneI ΔgabD ΔmaeA ΔmaeB | $P_{synI}$-phaC1-$P_{uspA}$-sucD*-ssaR$_{At}$*; $P_{rpsU}$-orfZ |

The strains were grown in a 48 hour shake plate assay. The production medium consisted of 1×E2 minimal salts solution containing 30 g/L glucose and 1× Trace Salts Solution. Both E2 medium and trace elements are described in Example 2. At the end of the growth phase, the biomass and P4HB titers were determined as described in Example 1.

The results in Table 15 show that strain 20 which lacks maeA and maeB produced more P4HB than strain 19 which retained these two genes.

TABLE 15

Biomass and P4HB titer for microbial strains 19 and 20

| Strain | Biomass Titer (g/L) | P4HB Titer (% dcw) |
|---|---|---|
| 19 | 10.26 ± 0.44 | 25.6 ± 4.8 |
| 20 | 12.50 ± 1.15 | 40.0 ± 4.6 |

Example 7

Improved P4HB Production by Overexpressing the Glyoxylate Bypass Effect of Removing the Glyoxylate Bypass Genes Noronha et al. (*Biotechnology and Bioengineering* 68(3): 316-327 (2000)) concluded that the glyoxylate shunt is inactive in a fadR-positive (and iclR-positive) *E. coli* strain using 13C-NMR/MS. However, mutants of *E. coli* that are fadR-negative were described by Maloy et al. (*J. Bacteriol.* 143: 720-725 (1980)) to have elevated levels of the glyoxylate shunt enzymes, isocitrate lyase and malate synthase. Since the LS5218 host strain parent used in these examples contains an unknown mutation in the fadR gene, called fadR601 (*E. coli* Genetic Resources at Yale, The *Coli* Genetic Stock Center, CGSC#: 6966; found at the world wide web: //cgsc.biology.yale.edu/index.php), it was of interest to investigate if carbon was channeled through the glyoxylate shunt (FIG. 1, Reaction numbers 5 and 6) and/or the oxidative branch of the TCA cycle via alpha-ketoglutarate towards succinyl-CoA. Two strains were thus constructed, both of which contained chromosomal deletions of yneI, gabD, pykF, pykA, maeA, maeB and overexpressed a PHA synthase, a succinyl-CoA dehydrogenase, an SSA reductase, a CoA-transferase and a PEP carboxylase (strain 21). Strain 22 contained additional deletions of the aceA and aceB genes encoding isocitrate lyase and malate synthase, respectively (Table 16).

TABLE 16

Microbial strains used in this section of Example 7

| Strains | Relevant host genome modifications | Genes overexpressed |
|---|---|---|
| 21 | fadR601, ΔgabD, ΔyneI, ΔpykF, ΔpykA, ΔmaeA, ΔmaeB | $P_{rpsU}$-orfZ, $P_{synI}$-ppc$_{Ec}$, $P_{synI}$-phaC1-$P_{uspA}$-sucD*-ssaR$_{At}$* |
| 22 | fadR601, ΔgabD, ΔyneI, ΔpykF, ΔpykA, ΔmaeA, ΔmaeB, ΔaceB, ΔaceA | $P_{rpsU}$-orfZ, $P_{synI}$-ppc$_{EC}$, $P_{synI}$-phaC1-$P_{uspA}$-sucD*-ssaR$_{At}$* |

The strains were grown in a 24 hour shake plate assay. The production medium consisted of 1×E2 minimal salts solution containing 15 g/L glucose, 1× Trace Salts Solution. Both E2 medium and trace elements are described in Example 2. At the end of the growth phase, the biomass and P4HB titers were determined as described in Example 1.

The results in Table 17 show that strain 22 containing an inactive glyoxylate shunt had highly reduced P4HB titers as compared to its parental strain 21.

TABLE 17

Biomass and P4HB titer for microbial strains 21 and 22

| Strains | Biomass Titer (g/L) | P4HB Titer (% dcw) |
|---|---|---|
| 21 | 3.5 ± 0.3 | 20.2 ± 7.0 |
| 22 | 3.0 ± 0.1 | 7.9 ± 0.3 |

Effect of Overexpressing the Glyoxylate Bypass Genes

Two strains were constructed both of which contained chromosomal deletions of yneI, gabD, pykF, pykA and overexpressed a PHA synthase, a succinyl-CoA dehydrogenase, an SSA reductase, a CoA-synthetase and a PEP carboxylase (strain 23). Strain 24 overexpressed in addition the aceBA genes from the IPTG-inducible $P_{trc}$ promoter while strain 23 contained an empty vector (Table 18).

TABLE 18

Microbial strains used in this section of Example 7

| Strains | Relevant host genome modifications | Genes overexpressed |
|---|---|---|
| 23 | fadR601, ΔgabD, ΔyneI, ΔpykF, ΔpykA | $P_{rpsU}$-orfZ, $P_{synI}$-ppc$_{Ec}$, $P_{synI}$-phaC1-$P_{uspA}$-sucD*-ssaR$_{At}$* |
| 24 | fadR601, ΔgabD, ΔyneI, ΔpykF, ΔpykA | $P_{rpsU}$-orfZ, $P_{synI}$-ppc$_{Ec}$, $P_{synI}$-phaC1-$P_{uspA}$-sucD*-ssaR$_{At}$*, $P_{trc}$-aceBA |

The strains were grown in a 24 hour shake plate assay. The production medium consisted of 1×E2 minimal salts solution containing 15 g/L glucose, 1× Trace Salts Solution and 100 µM IPTG. Both E2 medium and trace elements are described in Example 2. At the end of the growth phase, the biomass and P4HB titers were determined as described in Example 1.

The results in Table 19 show that strain 24 overexpressing the two glyoxylate shunt pathway enzymes produced higher P4HB titers than its parent strain 23 that did not express the aceBA genes from the $P_{trc}$ promoter.

TABLE 19

Biomass and P4HB titer for microbial strains 23 and 24

| Strains | Biomass Titer (g/L) | P4HB Titer (% dcw) |
|---|---|---|
| 23 | 3.12 ± 0.03 | 21.0 ± 1.2 |
| 24 | 3.27 ± 0.09 | 27.0 ± 1.0 |

Example 8

Improved P4HB Production by Overexpressing Glyceraldehydes-3-Phosphate Dehydrogenase Martinez et al., (Metab. Eng. 10:352-359 (2009)) genetically engineered an *Escherichia coli* strain to increase NADPH availability to improve the productivity of lycopene and s-caprolactone that require NADPH in its biosynthesis. Their approach involved an alteration of the glycolysis step where glyceraldehyde-3-phosphate is oxidized to 1,3 bisphosphoglycerate. This reaction is catalyzed by NAD-dependent endogenous glyceraldehyde-3-phosphate dehydrogenase (GAPDH) encoded by the gapA gene (FIG. 1, Reaction number 1). They constructed a recombinant *E. coli* strain by replacing the native NAD-dependent gapA gene with a NADP-dependent GAPDH from *Clostridium acetobutylicum* and demonstrated significant higher lycopene and ε-caprolactone productivity than the parent strains.

To determine whether the overexpression of an NADPH-generating GAPDH would lead to improved P4HB titer, the following six strains were constructed using the well known biotechnology tools and methods described earlier. All strains contained chromosomal deletions of yneI and gabD and overexpressed a PHA synthase, a succinyl-CoA dehydrogenase, an SSA reductase, a CoA-transferase. Strain 25 contained an empty vector and served as a negative control where no other recombinant gene was expressed. Strains 26 to 29 overexpressed a gene from an IPTG-inducible promoter that encodes an NADPH-generating GAPDH from various organisms, i.e. gdp1 from *Kluyveromyces lactis*, gap2 from *Synechocystis* sp. PCC6803, gapB from *Bacillus subtilis*, and gapN from *Streptococcus pyogenes*, respectively. As another control, strain 30 overexpressed the *E. coli* gapA gene that encodes the NADH-generating GAPDH (Table 20).

TABLE 20

Microbial strains used in Example 8

| Strains | Relevant host genome modifications | Genes overexpressed |
|---|---|---|
| 25 | ΔgabD, ΔyneI | $P_{rpsU}$-orfZ, $P_{synI}$-phaC1-$P_{uspA}$-sucD*-ssaR$_{At}$* |
| 26 | ΔgabD, ΔyneI | $P_{rpsU}$-orfZ, $P_{synI}$-phaC1-$P_{uspA}$-sucD*-ssaR$_{At}$*$P_{trc}$-gdp1 |
| 27 | ΔgabD, ΔyneI | $P_{rpsU}$-orfZ, $P_{synI}$-phaC1-$P_{uspA}$-sucD*-ssaR$_{At}$*$P_{trc}$-gap2 |
| 28 | ΔgabD, ΔyneI | $P_{rpsU}$-orfZ, $P_{synI}$-phaC1-$P_{uspA}$-sucD*-ssaR$_{At}$*$P_{trc}$-gapB |
| 29 | ΔgabD, ΔyneI | $P_{rpsU}$-orfZ, $P_{synI}$-phaC1-$P_{uspA}$-sucD*-ssaR$_{At}$*$P_{trc}$-gapN |
| 30 | ΔgabD, ΔyneI | $P_{rpsU}$-orfZ, $P_{synI}$-phaC1-$P_{uspA}$-sucD*-ssaR$_{At}$*$P_{trc}$-gapA |

The strains were grown in a 24 hour shake plate assay. The production medium consisted of 1×E2 minimal salts solution containing 10 g/L glucose and 1× Trace Salts Solution and 100 µM IPTG. Both E2 medium and trace elements are described in Example 2. At the end of the growth phase, the biomass and P4HB titers were determined as described in Example 1.

The results in Table 21 show that strains 26, 27, and 29 produced higher amounts of P4HB than control strain 25. Interestingly, strain 28 produced much less P4HB than strain 25. Surprisingly, overexpression of the endogenous gapA gene encoding the NADH-generating GAPDH in strain 30 outperformed all other strains.

TABLE 21

Biomass and P4HB titer for microbial strains 25-30

| Strains | Biomass Titer (g/L) | P4HB Titer (% dcw) |
|---|---|---|
| 25 | 2.52 ± 0.03 | 14.0 ± 0.3 |
| 26 | 2.84 ± 0.01 | 25.0 ± 1.0 |
| 27 | 2.50 ± 0.10 | 21.5 ± 0.9 |
| 28 | 2.20 ± 0.10 | 2.3 ± 0.1 |
| 29 | 2.48 ± 0.01 | 21.0 ± 1.0 |
| 30 | 3.03 ± 0.08 | 32.5 ± 0.6 |

Gene ID 001 Nucleotide Sequence: *Medicago sativa* phosphoenolpyruvate carboxylase ppc*

(SEQ ID NO. 1)

ATGGCAAACAAAATGGAAAAGATGGCAAGCATTGACGCGCAACTGCGCCAGTTGGTCCCGGCAAA

AGTCAGCGAGGACGACAAATTGATTGAATACGATGCTCTGTTGCTGGACCGCTTTCTGGACATTC

TGCAAGATCTGCATGGCGAGGATCTGAAGGATTCGGTTCAGGAAGTTTACGAACTGTCTGCGGAG

TATGAGCGTAAGCATGACCCGAAGAAGCTGGAAGAGCTGGGTAACTTGATTACGAGCTTTGACGC

GGGCGACAGCATTGTCGTGGCGAAATCGTTCTCTCATATGCTGAATCTGGCGAACCTGGCCGAAG

AAGTTCAAATTGCTCACCGCCGTCGTAACAAGCTGAAGAAGGGTGATTTTCGTGATGAGAGCAAT

-continued

```
GCGACCACCGAGTCCGATATTGAGGAGACTCTGAAGAAACTGGTTTTCGACATGAAGAAGTCTCC

GCAAGAAGTGTTTGACGCGTTGAAGAATCAGACCGTGGACCTGGTGCTGACGGCACATCCTACCC

AGAGCGTTCGCCGTTCCCTGCTGCAAAAGCATGGTCGTGTTCGTAATTGCTTGAGCCAGCTGTAT

GCGAAAGACATTACCCCGGATGACAAACAAGAGCTGGACGAGGCACTGCAGCGTGAAATCCAGGC

AGCGTTCCGTACCGATGAAATCAAACGTACCCCGCCGACCCCACAAGACGAAATGCGTGCTGGCA

TGAGCTATTTCCACGAAACCATCTGGAAGGGCGTCCCGAAGTTCCTGCGTCGCGTGGACACCGCG

TTGAAGAACATCGGCATTAACGAACGCGTGCCGTATAACGCCCCGCTGATTCAATTCAGCAGCTG

GATGGGTGGCGACCGTGACGGCAATCCGCGTGTTACGCCAGAAGTGACCCGTGATGTTTGTCTGC

TGGCGCGTATGATGGCGGCGAATTTGTACTATAGCCAGATTGAAGATCTGATGTTTGAGCTGTCT

ATGTGGCGCTGTAATGATGAGTTGCGTGTGCGTGCCGAAGAACTGCACCGCAATAGCAAGAAAGA

CGAAGTTGCCAAGCACTACATCGAGTTCTGGAAGAAGATCCCGTTGAACGAGCCGTACCGTGTTG

TTCTGGGTGAGGTCCGCGATAAGCTGTATCGCACCCGTGAGCGCAGCCGTTATCTGCTGGCACAC

GGTTATTGCGAAATTCCGGAGGAGGCGACCTTTACCAACGTGGATGAATTTCTGGAACCGCTGGA

GCTGTGTTATCGTAGCCTGTGCGCGTGCGGTGACCGCGCGATTGCGGACGGTTCTTTGCTGGATT

TCCTGCGCCAGGTGAGCACGTTTGGTCTGAGCCTGGTCCGTCTGGATATCCGTCAGGAATCGGAC

CGCCATACGGATGTGATGGACGCTATTACCAAACACCTGGAAATTGGCAGCTACCAGGAGTGGAG

CGAGGAGAAACGTCAAGAGTGGCTGCTGAGCGAGCTGATCGGTAAGCGTCCGCTGTTCGGTCCAG

ATCTGCCGCAAACCGACGAAATCCGCGACGTTCTGGACACCTTTCGTGTGATTGCCGAACTGCCG

AGCGACAACTTCGGCGCGTACATTATCTCCATGGCCACCGCCCCGAGCGATGTCCTGGCAGTCGA

GCTGCTGCAACGCGAATGTAAGGTCCGTAACCCGTTGCGCGTGGTTCCGCTGTTTGAAAAGCTGG

ATGACCTGGAGAGCGCACCGGCCGCACTGGCTCGTCTGTTTAGCATTGACTGGTACATTAACCGT

ATTGATGGTAAACAGGAAGTGATGATTGGTTACTCCGACAGCGGTAAAGATGCGGGTCGTTTTAG

CGCCGCATGGCAGCTGTACAAGGCACAAGAAGATCTGATCAAGGTTGCACAGAAGTTCGGCGTTA

AACTGACCATGTTCCACGGTCGCGCGTGGTACGGTTGGCCGTGGTGGCGGCCCAACCCACCTGGCG

ATTCTGAGCCAACCGCCGGAGACTATCCATGGTTCCTTGCGTGTCACCGTCCAGGGCGAAGTGAT

TGAGCAAAGCTTCGGCGAGGAACATCTGTGCTTTCGCACCCTGCAGCGTTTTACGGCCGCGACTT

TGGAACACGGCATGCGTCCGCCATCCAGCCCAAAGCCAGAATGGCGTGCGCTGATGGACCAAATG

GCGGTTATCGCGACCGAGGAGTATCGCAGCATTGTGTTCAAAGAGCCGCGTTTTGTGGAGTATTT

CCGTTTGGCAACGCCGGAGATGGAGTACGGCCGCATGAATATCGGCAGCCGTCCGGCAAAACGTC

GCCCGTCCGGCGGCATCGAGACGCTGCGTGCCATCCCGTGGATTTTCGCGTGGACGCAGACCCGT

TTCCATTTGCCGGTGTGGCTGGGTTTCGGTGCCGCCTTTCGTCAAGTCGTGCAGAAGGACGTGAA

GAATCTGCATATGCTGCAGGAGATGTACAACCAGTGGCCGTTCTTTCGTGTCACCATTGATCTGG

TGGAAATGGTCTTTGCGAAAGGTGATCCGGGCATCGCGGCGTTGAATGACCGTCTGCTGGTTTCC

AAAGACCTGTGGCCTTTTGGTGAACAGCTGCGTAGCAAGTACGAGGAAACCAAGAAACTGCTGTT

GCAAGTTGCGGCGCACAAGGAGGTGCTGGAAGGTGACCCTTATCTGAAGCAACGCCTGCGTCTGC

GTGACTCGTACATCACGACCCTGAATGTCTTTCAGGCGTATACCCTGAAGCGTATCCGTGACCCG

AATTACAAAGTGGAAGTTCGCCCTCCGATCAGCAAGGAGAGCGCGGAGACTAGCAAACCAGCGGA

CGAACTGGTCACCCTGAATCCGACCTCGGAGTATGCTCCGGGTTTGGAAGATACGCTGATTCTGA

CGATGAAGGGTATCGCGGCTGGCATGCAGAACACGGGCTAA
```

Gene ID 001 Protein Sequence: *Medicago sativa* phosphoenolpyruvate carboxylase ppc*
(SEQ ID NO. 2)

MANKMEKMASIDAQLRQLVPAKVSEDDKLIEYDALLLDRFLDILQDLHGEDLKDSVQEVYELSAE

YERKHDPKKLEELGNLITSFDAGDSIVVAKSFSHMLNLANLAEEVQIAHRRRNKLKKGDFRDESN

ATTESDIEETLKKLVFDMKKSPQEVFDALKNQTVDLVLTAHPTQSVRRSLLQKHGRVRNCLSQLY

AKDITPDDKQELDEALQREIQAAFRTDEIKRTPPTPQDEMRAGMSYFHETIWKGVPKFLRRVDTA

LKNIGINERVPYNAPLIQFSSWMGGDRDGNPRVTPEVTRDVCLLARMMAANLYYSQIEDLMFELS

MWRCNDELRVRAEELHRNSKKDEVAKHYIEFWKKIPLNEPYRVVLGEVRDKLYRTRERSRYLLAH

GYCEIPEEATFTNVDEFLEPLELCYRSLCACGDRAIADGSLLDFLRQVSTFGLSLVRLDIRQESD

RHTDVMDAITKHLEIGSYQEWSEEKRQEWLLSELIGKRPLFGPDLPQTDEIRDVLDTFRVIAELP

SDNFGAYIISMATAPSDVLAVELLQRECKVRNPLRVVPLFEKLDDLESAPAALARLFSIDWYINR

IDGKQEVMIGYSDSGKDAGRFSAAWQLYKAQEDLIKVAQKFGVKLTMFHGRGGTVGRGGGPTHLA

ILSQPPETIHGSLRVTVQGEVIEQSFGEEHLCFRTLQRFTAATLEHGMRPPSSPKPEWRALMDQM

AVIATEEYRSIVFKEPRFVEYFRLATPEMEYGRMNIGSRPAKRRPSGGIETLRAIPWIFAWTQTR

FHLPVWLGFGAAFRQVVQKDVKNLHMLQEMYNQWPFFRVTIDLVEMVFAKGDPGIAALNDRLLVS

KDLWPFGEQLRSKYEETKKLLLQVAAHKEVLEGDPYLKQRLRLRDSYITTLNVFQAYTLKRIRDP

NYKVEVRPPISKESAETSKPADELVTLNPTSEYAPGLEDTLILTMKGIAAGMQNTG

Gene ID 002 Nucleotide Sequence: *Clostridium kluyveri* succinate
semialdehyde dehydrogenase sucD*
(SEQ ID NO. 3)
ATGTCCAACGAGGTTAGCATTAAGGAGCTGATTGAGAAGGCGAAAGTGGCGCAGAAAAGCTGGA

AGCGTATAGCCAAGAGCAAGTTGACGTTCTGGTCAAGGCGCTGGGTAAAGTTGTGTACGACAACG

CCGAGATGTTCGCGAAAGAGGCGGTGGAGGAAACCGAGATGGGTGTTTACGAGGATAAAGTGGCT

AAATGTCATCTGAAATCTGGTGCAATCTGGAATCACATTAAAGATAAGAAAACCGTTGGTATTAT

CAAGGAAGAACCGGAGCGTGCGCTGGTGTACGTCGCGAAGCCTAAAGGTGTTGTGGCGGCGACGA

CCCCTATCACCAATCCTGTGGTTACCCCGATGTGTAACGCGATGGCAGCAATTAAAGGTCGCAAC

ACCATCATTGTCGCCCCGCATCCGAAGGCGAAGAAGGTGAGCGCGCACACCGTGGAGCTGATGAA

TGCAGAACTGAAAAAGTTGGGTGCGCCGGAAAACATTATCCAGATCGTTGAAGCCCCAAGCCGTG

AAGCAGCCAAGGAGTTGATGGAGAGCGCAGACGTGGTTATCGCCACGGGTGGCGCAGGCCGTGTT

AAAGCAGCGTACTCCTCCGGCCGTCCGGCATACGGTGTCGGTCCGGGCAATTCTCAGGTCATTGT

CGATAAGGGTTACGATTATAACAAAGCTGCCCAGGACATCATTACCGGCCGCAAGTATGACAACG

GTATCATTTGCAGCTCTGAGCAGAGCGTGATCGCACCGGCGGAGGACTACGACAAGGTCATCGCG

GCTTTCGTCGAGAATGGCGCGTTCTATGTCGAGGATGAGGAAACTGTGGAGAAATTCCGTAGCAC

GCTGTTCAAGGATGGCAAGATCAATAGCAAAATCATCGGTAAATCCGTGCAGATCATCGCTGACC

TGGCTGGTGTCAAGGTGCCGGAAGGCACCAAGGTGATCGTGTTGAAGGGCAAGGGTGCCGGTGAA

AAGGACGTTCTGTGCAAGGAGAAAATGTGCCCGGTCCTGGTTGCCCTGAAATATGACACCTTTGA

GGAGGCGGTCGAGATCGCGATGGCCAACTATATGTACAGAGGGTGCGGGCCATACCGCCGGTATCC

ACAGCGATAACGACGAGAATATCCGCTACGCGGGTACGGTGCTGCCAATCAGCCGTCTGGTTGTC

AACCAGCCAGCAACTACGGCCGGTGGTAGCTTTAACAATGGTTTTAATCCGACCACCACCTTGGG

CTGCGGTAGCTGGGGCCGTAACTCCATTAGCGAGAACCTGACGTATGAGCATCTGATTAATGTCA

GCCGTATTGGCTATTTCAATAAGGAGGCAAAAGTTCCTAGCTACGAGGAGATCTGGGGTTAA

Gene ID 002 Protein Sequence: *Clostridium kluyveri* succinate semialdehyde dehydrogenase sucD*

(SEQ ID NO. 4)

MSNEVSIKELIEKAKVAQKKLEAYSQEQVDVLVKALGKVVYDNAEMFAKEAVEETEMGVYEDKVA

KCHLKSGAIWNHIKDKKTVGIIKEEPERALVYVAKPKGVVAATTPITNPVVTPMCNAMAAIKGRN

TIIVAPHPKAKKVSAHTVELMNAELKKLGAPENIIQIVEAPSREAAKELMESADVVIATGGAGRV

KAAYSSGRPAYGVGPGNSQVIVDKGYDYNKAAQDIITGRKYDNGIICSSEQSVIAPAEDYDKVIA

AFVENGAFYVEDEETVEKFRSTLFKDGKINSKIIGKSVQIIADLAGVKVPEGTKVIVLKGKGAGE

KDVLCKEKMCPVLVALKYDTFEEAVEIAMANYMYEGAGHTAGIHSDNDENIRYAGTVLPISRLVV

NQPATTAGGSFNNGFNPTTTLGCGSWGRNSISENLTYEHLINVSRIGYFNKEAKVPSYEEIWG

Gene ID 003 Nucleotide Sequence: *Arabidopsis thaliana* succinic semialdehyde reductase ssaR$_{At}$*

(SEQ ID NO. 5)

ATGGAAGTAGGTTTTCTGGGTCTGGGCATTATGGGTAAAGCTATGTCCATGAACCTGCTGAAAAA

CGGTTTCAAAGTTACCGTGTGGAACCGCACTCTGTCTAAATGTGATGAACTGGTTGAACACGGTG

CAAGCGTGTGCGAGTCTCCGGCTGAGGTGATCAAGAAATGCAAATACACGATCGCGATGCTGAGC

GATCCGTGTGCAGCTCTGTCTGTTGTTTTCGATAAAGGCGGTGTTCTGGAACAGATCTGCGAGGG

TAAGGGCTACATCGACATGTCTACCGTCGACGCGGAAACTAGCCTGAAAATTAACGAAGCGATCA

CGGGCAAAGGTGGCCGTTTTGTAGAAGGTCCTGTTAGCGGTTCCAAAAAGCCGGCAGAAGACGGC

CAGCTGATCATCCTGGCAGCAGGCGACAAAGCACTGTTCGAGGAATCCATCCCGGCCTTTGATGT

ACTGGGCAAACGTTCCTTTTATCTGGGTCAGGTGGGTAACGGTGCGAAAATGAAACTGATTGTTA

ACATGATCATGGGTTCTATGATGAACGCGTTTAGCGAAGGTCTGGTACTGGCAGATAAAAGCGGT

CTGTCTAGCGACACGCTGCTGGATATTCTGGATCTGGGTGCTATGACGAATCCGATGTTCAAAGG

CAAAGGTCCGTCCATGACTAAATCCAGCTACCCACCGGCTTTCCCGCTGAAACACCAGCAGAAAG

ACATGCGTCTGGCTCTGGCTCTGGGCGACGAAAACGCTGTTAGCATGCCGGTCGCTGCGGCTGCG

AACGAAGCCTTCAAGAAAGCCCGTAGCCTGGGCCTGGGCGATCTGGACTTTTCTGCTGTTATCGA

AGCGGTAAAATTCTCTCGTGAATAA

Gene ID 003 Protein Sequence: *Arabidopsis thaliana* succinic semialdehyde reductase ssaR$_{At}$*

(SEQ ID NO. 6)

MEVGFLGLGIMGKAMSMNLLKNGFKVTVWNRTLSKCDELVEHGASVCESPAEVIKKCKYTIAMLS

DPCAALSVVFDKGGVLEQICEGKGYIDMSTVDAETSLKINEAITGKGGRFVEGPVSGSKKPAEDG

QLIILAAGDKALFEESIPAFDVLGKRSFYLGQVGNGAKMKLIVNMIMGSMMNAFSEGLVLADKSG

LSSDTLLDILDLGAMTNPMFKGKGPSMTKSSYPPAFPLKHQQKDMRLALALGDENAVSMPVAAAA

NEAFKKARSLGLGDLDFSAVIEAVKFSRE

Gene ID 004 Nucleotide Sequence: *Aspergillus terreus* succinic semialdehyde reductase ssaR$_{At2}$*

(SEQ ID NO. 7)

ATGCCACTGGTTGCTCAAAATCCACTGCCACGTGCTATTCTGGGTCTGATGACTTTCGGTCCGAG

CGAAAGCAAAGGTGCGCGTATCACTTCCCTGGATGAGTTTAACAAGTGCCTGGATTACTTCCAGC

AGCAGGGCTTCCAGGAAATCGATACCGCGCGCATCTACGTCGGCGGTGAACAGGAGGCATTCACG

-continued

```
GCGCAGGCAAAGTGGAAAGAACGCGGCCTGACGCTGGCGACTAAGTGGTATCCGCAGTACCCGGG

TGCGCACAAACCGGATGTCCTGCGTCAGAACCTGGAGCTGTCCCTGAAAGAACTGGGCACGAACC

AGGTCGATATCTTCTATCTGCACGCCGCGGATCGTTCTGTGCCGTTCGCGGAAACTCTGGAAACT

GTTAACGAACTGCACAAAGAAGGCAAATTTGTTCAGCTGGGTCTGTCTAACTACACCGCTTTCGA

AGTAGCTGAAATCGTGACCCTGTGTAACGAGCGTGGTTGGGTTCGTCCGACTATCTACCAGGCGA

TGTATAACGCTATCACCCGTAACATCGAAACTGAACTGATCCCGGCGTGCAAGCGTTACGGTATT

GACATTGTTATCTACAACCCACTGGCGGGTGGCCTGTTCAGCGGCAAATACAAAGCACAGGACAT

CCCGGCTGAAGGTCGTTACAGCGACCAATCTTCCATGGGCCAGATGTACCGCAACCGTTACTTTA

AGGACGCAACCTTTGACGCTCTGCGCCTGATCGAACCGGTTGTTGCGAAGCACGGCCTGACGATG

CCGGAAACCGCGTTCCGCTGGGTCCACCACCACTCCGCACTGAACATGGAAGATGGCGGCCGTGA

CGGCATCATTCTGGGTGTAAGCAGCCTGGCTCAGCTGGAAAACAACCTGAAAGACATTCAGAAAG

GTCCGCTGCCGCAGGAGGTTGTAGACGTCCTGGATCAGGCTTGGCTGGTGGCTAAGCCGACGGCT

CCAAACTACTGGCATCTGGACCTGAAATACACGTACGACACCCAGGAAGCTCTGTTCAAACCGAA

ATCTAAGGCGTAA
```

Gene ID 004 Protein Sequence: *Aspergillus terreus* succinic semialdehyde reductase ssaR$_{At2}$*

(SEQ ID NO. 8)

```
MPLVAQNPLPRAILGLMTFGPSESKGARITSLDEFNKCLDYFQQQGFQEIDTARIYVGGEQEAFT

AQAKWKERGLTLATKWYPQYPGAHKPDVLRQNLELSLKELGTNQVDIFYLHAADRSVPFAETLET

VNELHKEGKFVQLGLSNYTAFEVAEIVTLCNERGWVRPTIYQAMYNAITRNIETELIPACKRYGI

DIVIYNPLAGGLFSGKYKAQDIPAEGRYSDQSSMGQMYRNRYFKDATFDALRLIEPVVAKHGLTM

PETAFRWVHHHSALNMEDGGRDGIILGVSSLAQLENNLKDIQKGPLPQEVVDVLDQAWLVAKPTA

PNYWHLDLKYTYDTQEALFKPKSKAAVKFSRE
```

Gene ID 005 Nucleotide Sequence: *Mus musculus* succinic semialdehyde reductase ssaR$_{Mm}$*

(SEQ ID NO. 9)

```
ATGCTGCGTGCTGCTTCTCGTGCTGTTGGTCGTGCTGCTGTACGTTCCGCTAACGTTCTGGTAC

TAGCGTTGGCCGTCCGCTGGCGATGTCCCGTCCACCGCCGCCTCGCGCAGCTAGCGGTGCCCCGC

TGCGTCCGGCAACCGTACTGGGCACTATGGAGATGGGTCGTCGCATGGACGCTTCTGCATCCGCG

GCAAGCGTTCGTGCGTTCCTGGAACGTGGCCATAGCGAACTGGATACCGCTTTCATGTATTGCGA

CGGTCAGTCCGAAAATATCCTGGGTGGCCTGGGCCTGGGTCTGGGCTCCGGTGATTGTACCGTTA

AAATTGCGACCAAGGCGAACCCTTGGGAGGGCAAGAGCCTGAAGCCGGATTCTGTGCGTTCTCAG

CTGGAGACTTCTCTGAAACGTCTGCAGTGTCCGCGCGTAGACCTGTTCTATCTGCATGCGCCGGA

CCACAGCACTCCGGTAGAGGAAACTCTGCGTGCGTCATCAGCTGCACCAGGAAGGCAAGTTCG

TCGAACTGGGTCTGTCTAACTACGCATCTTGGGAAGTGGCAGAAATCTGTACGCTGTGTAAGTCT

AATGGTTGGATCCTGCCAACCGTGTACCAGGGCATGTACAACGCTACCACCCGCCAGGTAGAAGC

AGAACTGCTGCCGTGCCTGCGTCACTTCGGCCTGCGCTTTTACGCTTACAACCCGCTGGCGGGTG

GTCTGCTGACGGGCAAATACAAGTATGAAGATAAAGATGGTAAACAACCGGTCGGTCGTTTCTTT

GGTAACAACTGGGCCGAAACCTACCGTAATCGCTTCTGGAAAGAGCACCACTTTGAAGCGATCGC
```

-continued

ACTGGTTGAAAAAGCGCTGCAGACGACTTATGGCACTAACGCGCCGCGTATGACCTCCGCTGCGC

TGCGTTGGATGTACCACCATAGCCAGCTGCAGGGTACTCGCGGCGATGCCGTTATCCTGGGCATG

AGCTCCCTGGAACAGCTGGAACAGAACCTGGCCGCGACTGAAGAGGGCCCGCTGGAACCGGCAGT

TGTCGAAGCTTTTGACCAGGCATGGAACATGGTGGCGCACGAATGTCCAAACTATTTCCGCTAA

Gene ID 005 Protein Sequence: *Mus musculus* succinic semialdehyde
reductase ssaR$_{Mm}$*

(SEQ ID NO. 10)

MLRAASRAVGRAAVRSAQRSGTSVGRPLAMSRPPPPRAASGAPLRPATVLGTMEMGRRMDASASA

ASVRAFLERGHSELDTAFMYCDGQSENILGGLGLGLGSGDCTVKIATKANPWEGKSLKPDSVRSQ

LETSLKRLQCPRVDLFYLHAPDHSTPVEETLRACHQLHQEGKFVELGLSNYASWEVAEICTLCKS

NGWILPTVYQGMYNATTRQVEAELLPCLRHFGLRFYAYNPLAGGLLTGKYKYEDKDGKQPVGRFF

GNNWAETYRNRFWKEHHFEAIALVEKALQTTYGTNAPRMTSAALRWMYHHSQLQGTRGDAVILGM

SSLEQLEQNLAATEEGPLEPAVVEAFDQAWNMVAHECPNYFR

Gene ID 006 Nucleotide Sequence: *Pseudomonas putida/Ralstonia eutropha*
JMP134 Polyhydroxyalkanoate synthase fusion protein phaC3/C1

(SEQ ID NO. 11)

ATGACTAGAAGGAGGTTTCATATGAGTAACAAGAACAACGATGAGCTGGCGACGGGTAAAGGTGC

TGCTGCATCTTCTACTGAAGGTAAATCTCAGCCGTTTAAATTCCCACCGGGTCCGCTGGACCCGG

CCACTTGGCTGGAATGGAGCCGTCAGTGGCAAGGTCCGGAGGGCAATGGCGGTACCGTGCCGGGT

GGCTTTCCGGGTTTCGAAGCGTTCGCGGCGTCCCCGCTGGCGGGCGTGAAAATCGACCCGGCTCA

GCTGGCAGAGATCCAGCAGCGTTATATGCGTGATTTCACCGAGCTGTGGCGTGGTCTGGCAGGCG

GTGACACCGAGAGCGCTGGCAAACTGCATGACCGTCGCTTCGCGTCCGAAGCGTGGCACAAAAAC

GCGCCGTATCGCTATACTGCGGCATTTTACCTGCTGAACGCACGTGCACTGACGGAACTGGCTGA

TGCAGTAGAAGCGGATCCGAAAACCCGTCAGCGTATCCGTTTTGCGGTTTCCCAGTGGGTAGATG

CTATGAGCCCGGCTAACTTCCTGGCCACCAACCCGGACGCTCAGAACCGTCTGATCGAGAGCCGT

GGTGAAAGCCTGCGTGCCGGCATGCGCAATATGCTGGAAGATCTGACCCGCGGTAAAATTTCCCA

AACCGATGAGACTGCCTTCGAAGTAGGCCGTAACATGGCAGTTACCGAAGGTGCTGTGGTATTCG

AAAACGAGTTCTTCCAGCTGCTGCAGTACAAACCTCTGACTGACAAAGTATACACCCGTCCGCTG

CTGCTGGTACCGCCGTGCATTAACAAGTTCTATATTCTGGACCTGCAGCCGGAAGGTTCTCTGGT

CCGTTACGCAGTCGAACAGGGTCACACTGTATTCCTGGTGAGCTGGCGCAATCCAGACGCTAGCA

TGGCTGGCTGTACCTGGGATGACTATATTGAAAACGCGGCTATCCGCGCCATCGAGGTTGTGCGT

GATATCAGCGGTCAGGACAAGATCAACACCCTGGGCTTTTGTGTTGGTGGCACGATCATCTCCAC

TGCCCTGGCGGTCCTGGCCGCCCGTGGTGAGCACCCGGTGGCCTCTCTGACCCTGCTGACTACCC

TGCTGGACTTCACCGATACTGGTATCCTGGATGTTTTCGTGGACGAGCCACACGTTCAGCTGCGT

GAGGCGACTCTGGGCGGCGCCAGCGGCGGTCTGCTGCGTGGTGTCGAGCTGGCCAATACCTTTTC

CTTCCTGCGCCCGAACGACCTGGTTTGGAACTACGTTGTTGACAACTATCTGAAAGGCAACACCC

CGGTACCTTTCGATCTGCTGTTCTGGAACGGTGATGCAACCAACCTGCCTGGTCCATGGTACTGT

TGGTACCTGCGTCATACTTACCTGCAGAACGAACTGAAAGAGCCGGGCAAACTGACCGTGTGTAA

CGAACCTGTGGACCTGGGCGCGATTAACGTTCCTACTTACATCTACGGTTCCCGTGAAGATCACA

TCGTACCGTGGACCGCGGCTTACGCCAGCACCGCGCTGCTGAAGAACGATCTGCGTTTCGTACTG

-continued
```
GGCGCATCCGGCCATATCGCAGGTGTGATCAACCCTCCTGCAAAGAAAAAGCGTTCTCATTGGAC

CAACGACGCGCTGCCAGAATCCGCGCAGGATTGGCTGGCAGGTGCTGAGGAACACCATGGTTCCT

GGTGGCCGGATTGGATGACCTGGCTGGGTAAACAAGCCGGTGCAAAACGTGCAGCTCCAACTGAA

TATGGTAGCAAGCGTTATGCTGCAATCGAGCCAGCGCCAGGCCGTTACGTTAAAGCGAAAGCATA

A
```

Gene ID 006 Protein Sequence: *Pseudomonas putida/Ralstonia eutropha* JMP134 Polyhydroxyalkanoate synthase fusion protein phaC3/C1
(SEQ ID NO. 12)

```
MSNKNNDELATGKGAAASSTEGKSQPFKFPPGPLDPATWLEWSRQWQGPEGNGGTVPGGFPGFEA

FAASPLAGVKIDPAQLAEIQQRYMRDFTELWRGLAGGDTESAGKLHDRRFASEAWHKNAPYRYTA

AFYLLNARALTELADAVEADPKTRQRIRFAVSQWVDAMSPANFLATNPDAQNRLIESRGESLRAG

MRNMLEDLTRGKISQTDETAFEVGRNMAVTEGAVVFENEFFQLLQYKPLTDKVYTRPLLLVPPCI

NKFYILDLQPEGSLVRYAVEQGHTVFLVSWRNPDASMAGCTWDDYIENAAIRAIEVVRDISGQDK

INTLGFCVGGTIISTALAVLAARGEHPVASLTLLTTLLDFTDTGILDVFVDEPHVQLREATLGGA

SGGLLRGVELANTFSFLRPNDLVWNYVVDNYLKGNTPVPFDLLFWNGDATNLPGPWYCWYLRHTY

LQNELKEPGKLTVCNEPVDLGAINVPTYIYGSREDHIVPWTAAYASTALLKNDLRFVLGASGHIA

GVINPPAKKKRSHWTNDALPESAQDWLAGAEEHHGSWWPDWMTWLGKQAGAKRAAPTEYGSKRYA

AIEPAPGRYVKAKA
```

Example 9

Generation of Gamma-Butyrolactone from the Pyrolysis of a Genetically Engineered Microbe Producing Poly-4-Hydroxybutyrate Biomass containing poly(4-hydroxybutyrate) (P4HB) was produced in a 20 L New Brunswick Scientific fermentor (BioFlo 4500) using a genetically modified *E. coli* strain specifically designed for production of poly-4HB from glucose syrup as a carbon feed source. Examples of the *E. coli* strains, fermentation conditions, media and feed conditions are described in U.S. Pat. Nos. 6,316,262; 6,689,589; 7,081,357; and 7,229,804 incorporated by reference herein. The *E. coli* strain generated a fermentation broth which had a P4HB titer of approximately 100-120 g of P4HB/kg of broth. After the fermentation was complete, 100 g of the fermentation broth (e.g. P4HB biomass) was mixed with an aqueous slurry containing 10% by weight lime (Ca(OH)$_2$ 95+%, Sigma Aldrich). A 2 g portion of the broth+lime mixture was then dried in an aluminum weigh pan at 150° C. using an infrared heat balance (MB-45 Ohaus Moisture Analyzer) to constant weight. Residual water remaining was <5% by weight. The final lime concentration in the dry broth was 50 g lime/kg of dry solids or 5% by wt. A sample containing only dried fermentation broth (no lime addition) was prepared as well. Additionally, a sample of pure poly-4HB was recovered by solvent extraction as described in U.S. Pat. Nos. 7,252,980 and 7,713,720, followed by oven drying to remove the residual solvent.

The dry P4HB biomass samples were analyzed by TGA using an isothermal temperature of 300° C. under a N$_2$ gas purge. FIG. 3 shows the TGA weight loss vs. time curves for the dry fermentation broth with lime (dashed curve), and without lime (solid curve). Each dry broth sample showed a single major weight loss event. Also shown in the plots are the slopes of the weight loss curves (indicating the thermal degradation rate) and the onset times for completion of weight loss. Table 22 shows the thermal degradation rate data for the two dry broth samples. With the addition of 5 wt % lime, the dry broth showed a 34% faster rate of weight loss as compared to the dry broth with no lime added. Also the onset time for completion of thermal degradation was approximately 30% shorter in the dry broth with added lime sample. These results showed that the lime catalyst significantly sped up the P4HB biomass thermal degradation process.

Both dry broth samples and a pure poly-4HB sample were then analyzed by Py-GC-MS in order to identify the compounds being generated during thermal degradation at 300° C. in an inert atmosphere. FIG. 4 shows the chromatograms of pyrolyzed pure poly-4HB, dry broth without added lime, and dry broth with added lime. For all of the samples, two major thermal degradation components were identified from the pyrolysis at 300° C.: GBL (peak at 6.2 min), and the dimer of GBL (peak at 11.1 min). The dimer of GBL was identified as (3-(dihydro-2(3H)-furanylidene)dihydro-2(3H)-furanone). FIG. 4 shows the mass spectral library matches identifying these two peaks.

Table 22 below summarizes the Py-GC-MS data measured for the pure poly-4HB polymer, dry poly-4HB broth without added lime, and the dry poly-4HB broth with added lime. Both the selectivity and yield of GBL from broth were observed to increase with addition of the lime catalyst. The yield was calculated by taking the GBL peak area counts and dividing by the weight of P4HB in each sample. For the broth samples, the % P4HB was measured to be ~49% by weight of the total biomass. The fermentation broth media typically has potassium (4-7% by wt.) and sodium metal salts (<1% by wt.) present in it so that the increase in the yield of GBL was only 10% after lime addition. However, the selectivity for GBL was increased by a factor of 2 after the lime addition. As is evident from Table 22, higher lime concentration suppressed the formation of the GBL dimer, while increasing the yield of GBL relative to weight of poly-4HB pyrolyzed.

TABLE 22

Summary of Pyrolysis-GC-MS at 300° C. and TGA data for poly-4HB pure polymer, dry poly-4HB broth and dry poly-4HB broth with added lime.

| Sample ID | Ratio of GBL/GBL Dimer | Area Counts GBL/mg of poly-4HB pyrolized | Thermal Degradation Rate* (% Wt loss/min) |
|---|---|---|---|
| Poly-4HB pure polymer | 14.7 | $8.72 \times 10^6$ | — |
| Dry poly-4HB broth | 26.5 | $1.37 \times 10^7$ | −79.7 |
| Dry poly-4HB broth + 5% by wt lime | 54.0 | $1.51 \times 10^7$ | −107 |

*Measured from the slope of the TGA weight loss curves at 300° C. under $N_2$ atmosphere.

Example 10

Effect of Temperature, Catalyst Type, Catalyst Concentration and Broth Type on the Generation of Gamma-Butyrolactone from the Pyrolysis of a Genetically Engineered Microbe Producing Poly-4-Hydroxybutyrate In this example, a designed experiment (DOE) was carried out to determined the effects of pyrolysis temperature, catalyst type, catalyst concentration and broth type on the purity of GBL produced from a P4HB-containing microbial fermentation broth. Table 23 shows the DOE parameters and conditions tested. Sixteen different experimental conditions were tested in total. Py-GC-MS was used to measure the GBL purity. Two replicates at each condition were carried out for a total of thirty-two Py-GC-MS runs. TGA was also measured to assess the effect of the catalysts on the thermal degradation rate of P4HB at the various pyrolysis temperatures. Only single runs at each experimental condition were made for these measurements. For comparison, dry broth+P4HB samples (washed and unwashed) having no catalyst added were also prepared and analyzed by TGA and Py-GC-MS but were not part of the overall experiment.

TABLE 23

Design of Experiment parameters and conditions for determining the effect of pyrolysis temperature, catalyst type, catalyst concentration and broth type on GBL purity generated from microbial fermentation broth + P4HB.

| Broth Type | Catalyst type | Catalyst Concentration* | Pyrolysis Temp (° C.) |
|---|---|---|---|
| Unwashed | $Ca(OH)_2$, $Mg(OH)_2$, $FeSO_4$, $Na_2CO_3$ | 1, 3, 5, 10% | 225, 250, 275, 300 |
| Washed | $Ca(OH)_2$, $Mg(OH)_2$, $FeSO_4$, $Na_2CO_3$ | 1, 3, 5, 10% | 225, 250, 275, 300 |

*Wt % metal ion relative to the dry cell mass of the broth.

Biomass containing poly(4-hydroxybutyrate) (poly-4HB) was produced in a 20 L New Brunswick Scientific fermentor (BioFlo 4500) using a genetically modified *E. coli* strain specifically designed for high yield production of poly-4HB from glucose syrup as a carbon feed source. Examples of the *E. coli* strains, fermentation conditions, media and feed conditions are described in U.S. Pat. Nos. 6,316,262; 6,689,589; 7,081,357; and 7,229,804. The *E. coli* strain generated a fermentation broth which had a PHA titer of approximately 100-120 g of PHA/kg of broth. After fermentation, the fermentation broth containing the microbial biomass and P4HB polymer was split into two fractions. One fraction was used without any further processing and was identified as 'unwashed' broth. The unwashed broth had a dry solids content of 13.7% (dry solids weight was measured using an MB-45 Ohaus Moisture Analyzer). The other fraction was washed by adding an equal volume of distilled-deionized water to the broth, stirring the mixture for 2 minutes, centrifuging and then decanting the liquid and retaining the solid biomass+P4HB. The wash step was repeated a second time and then after centrifuging and decanting, the remaining solids were resuspended again in DI water to give a 12.9% by weight dry solids solution. This material was designated 'washed' broth. Table 24 shows the trace metals analysis by Ion Chromatography of the two broth types. The results showed that the unwashed broth had high levels of potassium and sodium ions present due to the media components used to grow the microbial cells. After the washing step, the potassium, magnesium and sodium ions were significantly reduced thereby reducing the overall metals content of the broth+P4HB by a factor of 6.

TABLE 24

Summary of Ion Chromatography results for fermentation broth + P4HB before and after washing with distilled deionized water.

| Broth + P4HB Type | Metal Ion | Metal Ion Concentration |
|---|---|---|
| Unwashed | Calcium | 39.8 ppm |
| | Magnesium | 811 ppm |
| | Potassium | 6.07% |
| | Sodium | 0.38% |
| Washed (2 times) | Calcium | 40.2 ppm |
| | Magnesium | 419 ppm |
| | Potassium | 0.83% |
| | Sodium | None detected |

The pyrolysis catalysts used in this experiment included $Ca(OH)_2$ (95+% Sigma Aldrich), $Mg(OH)_2$ (Sigma Aldrich), $FeSO_4 \cdot 7H_2O$ (JT Baker), and $Na_2CO_3$ (99.5+% Sigma Aldrich). Aqueous slurries of the $Ca(OH)_2$, $Mg(OH)_2$ and $FeSO_4 \cdot 7H_2O$ catalysts were prepared in DI water (25-30% by weight solids) and added to the broth samples while the $Na_2CO_3$ was added to the broth+P4HB directly as a solid. As shown in Table 23, the catalyst concentrations targeted for the experiment were 1%, 3%, 5% and 10% based on the weight of the metal ion relative to the dry solids weight of the broth. To prepare the broth+P4HB/catalyst samples, 10 g of either washed or unwashed broth was added to a 15 ml centrifuge tube. Next, the appropriate amount of catalyst solution or solid was added and the mixture vortexed for 30 sec. The mixture was then centrifuged, decanted and poured into a drying dish. Finally the drying dish was placed in an oven at 110° C. and dried to constant weight. Dry samples of unwashed and washed broth containing no catalysts were also prepared by centrifuging, decanting and drying at 110° C.

Table 25 shows results from the TGA and Py-GC-MS analyses on the broth+P4HB samples which have no catalysts added.

TABLE 25

Summary of TGA and Py-GC-MS results for broth + P4HB samples having no catalyst added to them.

| Broth Type | Catalyst | Pyrolysis Temp. (° C.) | TGA Slope (% Wt loss/min) | GBL/GBL Dimer Peak Area Ratio |
|---|---|---|---|---|
| unwashed | None | 225 | −17.9 | 45.6 |
| washed | None | 225 | −1.88 | 32.2 |
| unwashed | None | 250 | −43.9 | 23.1 |
| washed | None | 250 | −4.38 | 32.4 |
| unwashed | None | 275 | −64.0 | 36.6 |
| washed | None | 275 | −8.39 | 39.2 |
| unwashed | None | 300 | −97.0 | 28.9 |
| washed | None | 300 | −28.9 | 40.3 |

The results from Table 25 show that washing the broth+P4HB before pyrolyzing had a significant impact on lowering the rate of thermal decomposition at all pyrolysis temperatures. From the Ion Chromatography results in Table 24, it can be seen that the overall concentration of metal ions present in the washed broth was lowered by a factor of 6 as compared to the unwashed broth. This indicated that the metal ions present in the broth+P4HB after a fermentation run, by themselves had a catalytic effect on the degradation rate of P41-TB during pyrolysis. Kim era (2008, *Polymer Degradation and Stability*, 93, p 776-785) have shown that the metal ions Ca, Na, Mg, Zn, Sn and Al are all effective in catalyzing the thermal degradation of P4HB. What was not shown however was the effect that these metal ions had on the purity of the GBL produced by thermal decomposition of P4HB. Table 25 shows that for the unwashed broth+P4HB samples, the GBL purity (GBL/GBL dimer peak area ratio) decreased as the pyrolysis temperature increased. For the washed samples, the purity marginally improved with increasing pyrolysis temperature. The data in Table 25 suggests that for any process making biobased GBL by thermal decomposition of P4HB and a catalyst, there exits a trade off between speed of reaction and purity of the final product. The following data will show that the type and concentration of catalyst used significantly impacts both the thermal degradation rate and GBL purity in unanticipated ways.

Table 26 summarizes the TGA and Py-GC-MS experimental results for the pyrolysis of broth+P4HB as a function of catalyst type, concentration, pyrolysis temperature and broth type.

TABLE 26

Summary of TGA and Py-GC-MS results for broth + P4HB as a function of catalyst type, catalyst concentration, pyrolysis temperature and broth type.

| Run# | Broth Type | Catalyst | Catalyst Concentration (Wt %)* | Pyrolysis Temp. (° C.) | TGA Slope (% Wt loss/min) | GBL/GBL Dimer Peak Area Ratio |
|---|---|---|---|---|---|---|
| 1 | unwashed | FeSO$_4$ | 1% | 225 | −1.07 | — |
| 2 | unwashed | FeSO$_4$ | 1% | 225 | — | — |
| 3 | unwashed | Na$_2$CO$_3$ | 10% | 225 | −77.6 | 142.9 |
| 4 | unwashed | Na$_2$CO$_3$ | 10% | 225 | — | 91.74 |
| 5 | washed | Ca(OH)$_2$ | 3% | 225 | −35.0 | 480.7 |
| 6 | washed | Ca(OH)$_2$ | 3% | 225 | — | 617.3 |
| 7 | washed | Mg(OH)$_2$ | 5% | 225 | −33.1 | 147.6 |
| 8 | washed | Mg(OH)$_2$ | 5% | 225 | — | 122.1 |
| 9 | unwashed | Mg(OH)$_2$ | 1% | 250 | −41.6 | 38.19 |
| 10 | unwashed | Mg(OH)$_2$ | 1% | 250 | — | 49.75 |
| 11 | unwashed | Ca(OH)$_2$ | 10% | 250 | −78.2 | 1546 |
| 12 | unwashed | Ca(OH)$_2$ | 10% | 250 | — | 2016 |
| 13 | washed | Na$_2$CO$_3$ | 3% | 250 | −111 | 36.11 |
| 14 | washed | Na$_2$CO$_3$ | 3% | 250 | — | 28.30 |
| 15 | washed | FeSO$_4$ | 5% | 250 | −0.918 | — |
| 16 | washed | FeSO$_4$ | 5% | 250 | — | — |
| 17 | washed | Ca(OH)$_2$ | 1% | 275 | −14.2 | 35.39 |
| 18 | washed | Ca(OH)$_2$ | 1% | 275 | — | 55.07 |
| 19 | washed | FeSO$_4$ | 10% | 275 | −1.17 | — |
| 20 | washed | FeSO$_4$ | 10% | 275 | — | — |
| 21 | unwashed | Mg(OH)$_2$ | 3% | 275 | −109 | 118.1 |
| 22 | unwashed | Mg(OH)$_2$ | 3% | 275 | — | 135.2 |
| 23 | unwashed | Na$_2$CO$_3$ | 5% | 275 | −185 | 29.81 |
| 24 | unwashed | Na$_2$CO$_3$ | 5% | 275 | — | 30.84 |
| 25 | washed | Na$_2$CO$_3$ | 1% | 300 | −172 | 23.53 |
| 26 | washed | Na$_2$CO$_3$ | 1% | 300 | — | 17.33 |
| 27 | washed | Mg(OH)$_2$ | 10% | 300 | −55.5 | 48.59 |
| 28 | washed | Mg(OH)$_2$ | 10% | 300 | — | 25.52 |
| 29 | unwashed | FeSO$_4$ | 3% | 300 | −12.5 | — |
| 30 | unwashed | FeSO$_4$ | 3% | 300 | — | — |
| 31 | unwashed | Ca(OH)$_2$ | 5% | 300 | −164 | 46.49 |
| 32 | unwashed | Ca(OH)$_2$ | 5% | 300 | — | 34.45 |

*Wt % metal ion relative to the dry solids weight of the broth.

Statistical analysis of the data in Table 26 (using JMP statistical software from SAS), showed that for the fastest thermal degradation rate, the optimum variable parameters to use would be unwashed broth+P4HB, Na$_2$CO$_3$ as the catalyst at 5% concentration and a pyrolysis temperature of 300° C. Catalyst type was the most significant variable affecting the degradation rates which varied from −1 to −185% wt loss/min. Samples with FeSO$_4$ catalyst had degradation rates lower than even the washed broth+P4HB indicating that this compound acted more as a P4HB thermal stabilizer rather than a catalyst promoter. The samples which had the highest degradation rates were those with either Na$_2$CO$_3$ or Ca(OH)$_2$. Higher temperatures and generally higher catalyst concentration also favored faster degradation rates.

The statistical analysis of the GBL purity data showed that the optimum variable parameters for highest GBL purity were found using Ca(OH)$_2$ catalyst at 10% concentration and a pyrolysis temperature of 250° C. In comparison to the other variables, broth type had a negligible effect on the GBL purity. The most statistically significant variables for GBL purity, which ranged in value from 17 to 2016 (GBL/GBL dimer peak area ratio) were catalyst concentration and type. It was noted that the upper range values for GBL purity in the experimental results were much higher than those observed for the unwashed broth+P4HB samples in Table 25. This indicated that the metal ions remaining in broth from fermentation (mostly potassium) were not as effective for improving GBL purity as those used in the experiment. Pyrolysis temperature was also found to be a statistically significant variable for GBL purity (higher temperatures generated more dimer). In Table 26, the missing Py-GC-MS data for broth+P4HB with FeSO$_4$ as the catalyst was due to the fact that the samples took too long to pyrolyze under the Py-GC-MS conditions and therefore could not be quantitated. This was in agreement with the TGA data which showed FeSO$_4$ acted as a thermal stabilizer rather than catalyst promoter.

As shown in Example 9, addition of the catalyst Ca(OH)$_2$ to microbial biomass+P4HB suppressed the formation of GBL dimer producing a purer GBL liquid during pyrolysis of the biomass. The above experimental data confirmed this observation and showed that catalyst concentration and pyrolysis temperature were also important in determining the optimum conditions for producing high purity GBL from dry broth+P4HB by pyrolysis. The choice of catalyst and pyrolysis temperature was also shown to impact the rate of P4HB thermal degradation. Therefore one needs to carefully choose the correct conditions to optimize both variables when designing a robust process for production of biobased GBL.

Example 11

Larger Scale Production of Gamma-Butyrolactone from the Pyrolysis of a Genetically Engineered Microbe Producing Poly-4-Hydroxybutyrate In the following example, GBL production from pyrolyis of a fermentation broth+P4HB+catalyst mixture will be outlined showing the ability to produce a high purity, high yield biobased GBL on the hundred gram scale.

Biomass containing poly-4-hydroxybutyrate (poly-4HB) was produced in a 20 L New Brunswick Scientific fermentor (BioFlo 4500) using a genetically modified *E. coli* strain specifically designed for high yield production of poly-4HB from glucose syrup as a carbon feed source. Examples of the *E. coli* strains, fermentation conditions, media and feed conditions are described in U.S. Pat. Nos. 6,316,262; 6,689,589; 7,081,357; and 7,229,804. The *E. coli* strain generated a fermentation broth which had a PHA titer of approximately 100-120 g of PHA/kg of broth. After fermentation, the broth was washed with DI water by adding an equal volume of water, mixing for 2 minutes, centrifuging and decanting the water. Next, the washed broth was mixed with lime (Ca(OH)$_2$ standard hydrated lime 98%, Mississippi Lime) targeting 4% by wt dry solids. The mixture was then dried in a rotating drum dryer at 125-130° C. to a constant weight. Moisture levels in the dried biomass were approximately 1-2% by weight. The final wt % calcium ion in the dried broth+P4HB was measured by Ion Chromatography to be 1.9% (3.5% by wt. Ca(OH)$_2$).

Pyrolysis of the dried broth+P4HB+Ca(OH)$_2$ was carried out using a rotating, four inch diameter quartz glass kiln suspended within a clamshell tube furnace. At the start of the process, a weighed sample of dried broth+P4HB+Ca(OH)$_2$ was placed inside of the glass kiln and a nitrogen purge flow established. The furnace rotation and heat up would then be started. As the temperature of the furnace reached its set point value, gases generated by the broth+P4HB+Ca(OH)$_2$ sample would be swept out of the kiln by the nitrogen purge and enter a series of glass condensers or chilled traps. The condensers consisted of a vertical, cooled glass condenser tower with a condensate collection bulb located at the its base. A glycol/water mixture held at 0° C. was circulated through all of the glass condensers. The cooled gases that exited the top of the first condenser were directed downward through a second condenser and through a second condensate collection bulb before being bubbled through a glass impinger filled with deionized water. FIG. 7 shows a schematic diagram of the pyrolyzer and gas collection equipment.

For the larger scale pyrolysis experiment, 292 g of dried broth+P4HB+Ca(OH)$_2$ was first loaded into the quartz kiln at room temperature. The total weight of P4HB biomass was estimated to be 281.4 g based on Ca(OH)$_2$ loading. The wt % P4HB in the mixture was also measured to be 66.7% (see Doi, *Microbial Polyesters*, John Wiley and Sons, p 23, 1990) based on the dry solids which made the mass of P4HB in the kiln equal to 195 g. The system was then sealed up and a nitrogen purge of approximately 1500 ml/min was established. Power was applied to the furnace and the dried broth+P4HB+Ca(OH)$_2$ was heated up to the target pyrolysis temperature of 250° C. During pyrolysis, the products of thermal degradation of biomass+P4HB, GBL, were collected in the condensate traps below the cooled condensers. Water could be seen to collect initially in each of the collection bulbs. The majority of the liquified product (>95%) was collected in the first glass collection bulb. Total pyrolysis run time was approximately 60 minutes. The weight of the remaining biomass after pyrolysis was measured to be 11.9 g.

After the completion of the pyrolysis run, the condensates from the condensers were collected and weighed. The results showed that the combined condensate weight was 181 g. Analysis of the condensate by Karl Fisher moisture analysis and GC-MS showed that the condensate contained 6.1% water, 0.06% fatty acids with the balance of the material being GBL products. The GBL product yield ((g of GBL product/g of starting P4HB)×100%) therefore was calculated to be approximately 87%. The GC-MS results also showed that the major impurity in the GBL product was GBL dimer where the peak area ratio of GBL/GBL dimer was calculated to be 2777. This was in agreement with the results from the experiment in Example 10 showing that the optimum process conditions for highest GBL purity were at the 250° C. pyrolysis temperature with the Ca(OH)$_2$ catalyst. Other impurities such as organosulfur and amide compounds were also detected as being present in the condensate by GC-MS. The conversion of the P4HB biomass solid to liquid ((g of dry Biomass—g Residual biomass/g of dry biomass)×100%) was calculated to be 96%.

In another embodiment, it is also possible to subject the gamma-butyrolactone generated from processes described herein directly to hydrogenation, esterification or amidation conditions to produce the corresponding diol, hydroxyl ester and amide (e.g., 1,4-butanediol, alkyl 4-hydroxy butyrate, or N-alkyl 2-pyrrolidone when subjected to hydrogenation with H$_2$, esterification with alkyl alcohol and amidation with alkyl amine respectively).

The processing of fats and oils to produce alcohols provides some guidance in this respect. Oils and fats are significant sources of fatty alcohols that are used in a variety of applications such as lubricants and surfactants. The fats are not typically hydrogenated directly as the intensive reaction conditions tend to downgrade the glycerol to lower alcohols such as propylene glycol and propanol during the course of the hydrogenation. For this reason it is more conventional to first hydrolyze the oil and then pre-purify the fatty acids to enable a more efficient hydrogenation (see for instance Lurgi's hydrogenation process in Bailey's Industrial Oil and Fat Products, Sixth Edition, Six Volume Set. Edited by Fereidoon Shahidi, John Wiley & Sons, Inc.2005).

Example 12

Generation of Biobased 1,4-Butanediol from the Pyrolysis of a Genetically Engineered Biomass Producing Poly-4-Hydroxybutyrate Followed by Direct Hydrogenation The following example describes the generation of biobased 1,4-butanediol from biomass containing poly-4HB which can then be converted to gamma-butyrolactone produced by pyrolysis and finally to 1,4-butanediol via direct hydrogenation. Hydrogenation can take place either in the liquid phase or gas phase. Examples of both methods are given below.

Liquid Phase Hydrogenation Method: 5 g of microbial biomass containing >40% by weight poly-4HB can be heated at atmospheric pressure under nitrogen to 275° C. The generated vapors composed of >90% GBL are collected using a water cooled condenser held at 20° C. Approximately 2-3 g of GBL product can then be recovered for subsequent hydrogenation. A 50 mL autoclave is charged with 0.3 g of a Cu/Al/Zn oxide catalyst as outlined in U.S. Pat. No. 4,048,196. The autoclave is then flushed with a 98%/2% nitrogen/hydrogen gas mixture and heated to 150° C. to reduce the catalyst. A 10% by weight solution of recovered GBL product in DI water is introduced into the reactor. The reactor is further pressurized to 250 bar with pure $H_2$ gas and the hydrogenation reaction is allowed to proceed for 1-2 hours. Upon completion of the reaction, the reactor is cooled and depressurized followed by flushing with nitrogen. The autoclave contents are discharged and the catalyst separated by decantation. The catalyst is washed with additional DI water and the wash is added to the supernatant. An aliquot of supernatant is filtered and analyzed by HPLC to determined the percent conversion of GBL and the percent yield of 1,4-butanediol on a molar basis.

Vapor Phase Hydrogenation: Using the larger scale pyrolysis set up described in Example 11, vapor phase GBL product generated from the 250° C. pyrolysis of P4HB biomass+Ca(OH)$_2$ is directed into a heated and sealed reactor tube having a height/diameter ratio of 115. Previously the reactor had been charged with 3.5 kg of reduced Cu/Cr/Ba oxide catalyst pellets as described in U.S. Pat. No. 4,652,685. The catalyst is reduced by first heating the reactor to 130° C. under a $N_2$ purge. The reactor is then heated to 170° C., the $N_2$ flow stopped and 100% $H_2$ introduced to the reactor. The reactor temperature is then increased to 210° C. and the $H_2$ flow rate set at ~8 kg/hr. Vaporized GBL from the pyrolysis of P4HB biomass+Ca(OH)$_2$ is introduced into the reactor and passed through the reduced catalyst. The hydrogenated product is then sent to a water cooled condenser maintained at 20° C. and the liquid condensate collected. An aliquot of the condensate is analyzed by HPLC to determined the percent conversion of GBL and the percent yield of 1,4-butanediol on a molar basis.

Example 13

Generation of N-Methyl Pyrrolidone from the Pyrolysis of a Genetically Engineered Biomass Producing Poly-4-Hydroxybutyrate Followed by Reaction with Monomethylamine The following example describes the generation of N-methyl pyrrolidone from biomass containing poly-4HB which can then be converted to gamma-butyrolactone by pyrolysis and finally reacted with monomethylamine to produce N-methyl pyrrolidone.

5 g of microbial biomass containing >40% by weight poly-4HB can be heated at atmospheric pressure under nitrogen to 275° C. The generated vapors composed of >90% GBL can be collected using a water cooled condenser held at 20° C. Approximately 2-3 g of GBL product can then be recovered for subsequent reaction. A 50 mL autoclave is charged with 3 g of GBL product and 3.8 g of a 40% aqueous solution of monomethylamine. The autoclave is heated to a temperature of 290° C. which generates a pressure of 77 bars. The reaction is continued for a total time of 2 hours. An aliquot of the reaction product analyzed by HPLC to determined % conversion of GBL product and the % yield of N-methylpyrrolidone on a molar basis. The reaction is carried as described in U.S. Pat. No. 6,075,153.

Example 14

Generation of Poly-Vinylpyrrolidone from the Pyrolysis of a Genetically Engineered Biomass Producing Poly-4-Hydroxybutyrate Followed by Amidization, Vapor Phase Dehydration and Polymerization In this example, a method for preparing poly-vinyl pyrrolidone starting from P4HB biomass is described.

5 g of microbial biomass containing >40% by weight poly-4HB is heated at atmospheric pressure under nitrogen to 275° C. The generated vapors composed of >90% GBL are collected using a water cooled condenser held at 20° C. Approximately 2-3 g of GBL product is then recovered for subsequent reaction. A 50 mL autoclave is charged with 3 g of GBL product and 2.3 g of ethanolamine (Sigma Aldrich, cat#398136, >99% pure). The autoclave is heated under a nitrogen purge to a temperature of 200° C. for 90 minutes. After the reaction, the mixture is removed and placed into a 10 ml round bottom flask fitted with a water cooled microcondenser. The mixture is distilled at a temperature of 105° C. to remove water. The remaining liquid, N(2-hydroxyethyl)-2-pyrrolidone (HEP), is then dehydrated using a cesium on silica catalyst as described in U.S. Pat. No. 7,141,679. A 1 inch diameter, stainless steel, tube reactor is charged with 4 g of the catalyst and sealed. The reactor is then heated to 375° C. under a nitrogen purge. The recovered HEP is mixed with enough DI water to make a 10% solution. The added water reportedly reduces the formation of N-ethyl-2-pyrrolidone as a by-product during dehydrogenation. The HEP solution is fed into the reactor and vaporized. The HEP and water vapors are passed over the catalyst, reactor effluent exits the reactor and the NVP is collected in a cold trap. Polymerization of the NVP collected can be carried out under aqueous conditions as described in U.S. Pat. No. 4,254,239 or in organic solvent as described in U.S. Pat. No. 4,058,655. Both methods use organoperoxides to initiate the polymerization reaction.

Example 15

Non-Catalytic Conversion of Biobased Gamma-Butyrolactone to 2-Pyrrolidone

In this example, a method for preparing 2-Pyrrolidone starting from P4HB biomass is described. The intermediate GBL is converted non-catalytically to 2-Pyrrolidone as described in U.S. Pat. No. 5,393,888.

5 g of microbial biomass containing >40% by weight poly-4HB is heated at atmospheric pressure under nitrogen to 275° C. The generated vapors composed of >90% GBL are collected using a water cooled condenser held at 20° C. Approximately 2-3 g of GBL product is then recovered for subsequent reaction. A 50 mL autoclave is is maintained at 325° C. and 1,000 psi. 3 g of GBL is introduced to the reactor and after the reaction temperature is reached, liquid ammonia is introduced in two steps separated by 10 minutes to achieve a final molar ratio of 0.6 mol ammonia to 1.0 mol GBL. The reaction is continued while maintaining temperature and pressure for an additional 30 minutes after which the reaction mixture is allowed to cool to room temperature prior to removal and purification by two-stage distillation to remove low and high boiling impurities. 2-Pyrrolidone with purity in excess of 99% is produced after distillation.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The embodiments of the invention in which an exclusive property or privilege is claimed are defined as follows:

1. A process for production of a biobased gamma-butyrolactone product, comprising
   a) combining a genetically engineered biomass comprising poly-4-hydroxybutyrate and a catalyst; and
   b) heating the biomass with the catalyst to convert the poly 4-hydroxybutyrate to a gamma-butyrolactone product, wherein the catalyst is sodium carbonate or calcium hydroxide.

2. The process of claim 1, wherein the genetically engineered biomass is from a recombinant host having a poly-4-hydroxybutyrate pathway, wherein the host has an inhibiting mutation in its CoA-independent NAD-dependent succinic semialdehyde dehydrogenase gene or its CoA-independent NADP-dependent succinic semialdehyde dehydrogenase gene, or having the inhibiting mutations in both genes, and having stably incorporated one or more genes encoding one or more enzymes selected from a succinyl-CoA:coenzyme A transferase wherein the succinyl-CoA:coenzyme A transferase is able to convert succinate to succinyl-CoA, a succinate semialdehyde dehydrogenase wherein the succinate semialdehyde dehydrogenase is able to convert succinyl-CoA to succinic semialdehyde, a succinic semialdehyde reductase wherein the succinic semialdehyde reductase is able to convert succinic semialdehyde to 4-hydroxybutyrate, a CoA transferase wherein the CoA transferase is able to convert 4-hydroxybutyrate to 4-hydroxybutyryl-CoA, and a polyhydroxyalkanoate synthase wherein the polyhydroxyalkanoate synthase is able to polymerize 4-hydroxybutyryl-CoA to poly-4-hydroxybutyrate.

3. The process of claim 1 wherein the genetically engineered biomass is from a recombinant host having stably incorporated one or more genes encoding one or more enzymes selected from: a phosphoenolpyruvate carboxylase wherein the phosphoenolpyruvate carboxylase is able to convert phosphoenolpyruvate to oxaloacetate, an isocitrate lyase wherein the isocitrate lyase is able to convert isocitrate to glyoxalate, a malate synthase wherein the malate synthase is able to convert glyoxalate to malate and succinate, a succinate-CoA ligase (ADP-forming) wherein the succinate-CoA ligase (ADP-forming) is able to convert succinate to succinyl-CoA, an NADP-dependent glyceraldeyde-3-phosphate dehydrogenase wherein the NADP-dependent glyceraldeyde-3-phosphate dehydrogenase is able to convert glyceraldehyde 3-phosphate to 1,3-bisphosphoglycerate forming NADPH+ H$^+$, an NAD-dependent glyceraldeyde-3-phosphate dehydrogenase wherein the NAD-dependent glyceraldeyde-3-phosphate dehydrogenase is able to convert glyceraldehyde 3-phosphate to 1,3-bisphosphoglycerate forming NADH+ H$^+$, a butyrate kinase wherein the butyrate kinase is able to convert 4-hydroxybutyrate to 4-hydroxybutyryl-phosphate, a phosphotransbutyrylase wherein the phosphotransbutyrylase is able to convert 4-hydroxybutyryl-phosphate to 4-hydroxybutyryl-CoA; and optionally having a disruption in one or more genes selected from yneI, gabD, pykF, pykA, maeA and maeB.

4. The process of claim 1, wherein the process further includes an initial step of culturing a recombinant host with a renewable feedstock to produce a poly-4-hydroxybutyrate biomass.

5. The process of claim 4, wherein a source of the renewable feedstock is selected from glucose, fructose, sucrose, arabinose, maltose, lactose, xylose, fatty acids, vegetable oils, and biomass derived synthesis gas or a combination thereof.

6. The process of claim 1, wherein the biomass host is a bacteria, yeast, fungi, algae, cyanobacteria, or a mixture of any two or more thereof.

7. The process of claim 6, wherein the biomass host is bacteria.

8. The process of claim 7, wherein the bacteria is selected from *Escherichia coli, Alcaligenes eutrophus* (renamed as *Ralstonia eutropha*), *Bacillus* spp., *Alcaligenes latus, Azotobacter, Aeromonas, Comamonas, Pseudomonads*), *Pseudomonas, Ralstonia, Synechococcus* sp PCC7002, *Synechococcus* sp. PCC 7942, *Synechocystis* sp. PCC 6803, *Thermosynechococcus elongatus* BP-I, *Chlorobium tepidum, Chloroflexusauranticus, Chromatium tepidum* and *Chromatium vinosum Rhodospirillum rubrum, Rhodobacter capsulatus*, and *Rhodopseudomonas palustris*.

9. The process of claim 6, wherein the recombinant host is algae.

10. The process of claim 1, wherein heating is at a temperature of from about 100° C. to about 350° C.

11. The process of claim 1, wherein the weight percent of catalyst is in the range of about 4% to about 50%.

12. The process of claim 1, wherein heating reduces the water content of the biomass to about 5 wt %, or less.

13. The process of claim 1, wherein the heating temperature is from about 200° C. to about 350° C.

14. The process of claim 13, wherein the heating temperature is from about 225° C. to about 300° C.

15. The process of claim 1, wherein the heating is for a time period from about 30 seconds to about 5 minutes.

16. The process of claim 1, wherein the heating is for a time period from about 5 minutes to about 2 hours.

17. The process of claim 1, further comprising recovering the gamma-butyrolactone product.

18. The process of claim 1, wherein the gamma-butyrolactone product comprises less than 5% by weight of side products.

19. The process of claim 1, wherein the gamma-butyrolactone is further processed to form one or more of the following: 1,4-butanediol (BDO), tetrahydrofuran (THF), N-methylpyrrolidone (NMP), N-ethylpyrrolidone (NEP), 2-pyrrolidinone, N-vinylpyrrolidone (NVP) and polyvinylpyrrolidone (PVP).

20. The process of claim 1, wherein the genetically engineered biomass is from a recombinant host having a poly-4-hydroxybutyrate pathway, wherein the host has optionally an inhibiting mutation in its CoA-independent NAD-dependent succinic semialdehyde dehydrogenase gene or its CoA-independent NADP-dependent succinic semialdehyde dehydrogenase gene, or having inhibiting mutations in both genes, and having stably incorporated genes encoding the following enzymes: a succinyl-CoA:coenzyme A transferase wherein the succinyl-CoA:coenzyme A transferase is able to convert succinate to succinyl-CoA, a succinate semialdehyde dehydrogenase wherein the succinate semialdehyde dehydrogenase is able to convert succinyl-CoA to succinic semialdehyde, a succinic semialdehyde reductase wherein the succinic semialdehyde reductase is able to convert succinic semialdehyde to 4-hydroxybutyrate, a CoA transferase wherein the CoA transferase is able to convert 4-hydroxybutyrate to 4-hydroxybutyryl-CoA, and a polyhydroxyalkanoate synthase wherein the polyhydroxyalkanoate synthase is able to polymerize 4-hydroxybutyryl-CoA to poly-4-hydroxybutyrate.

21. The process of claim 1, wherein the genetically engineered biomass is from a recombinant host having stably incorporated genes encoding the following enzymes: a phosphoenolpyruvate carboxylase wherein the phosphoenolpyruvate carboxylase is able to convert phosphoenolpyruvate to oxaloacetate, an isocitrate lyase wherein the isocitrate lyase is able to convert isocitrate to glyoxalate, a malate synthase wherein the malate synthase is able to convert glyoxalate to malate and succinate, a succinate-CoA ligase (ADP-forming) wherein the succinate-CoA ligase (ADP-forming) is able to convert succinate to succinyl-CoA, an NADP-dependent glyceraldeyde-3-phosphate dehydrogenase wherein the NADP-dependent glyceraldeyde-3-phosphate dehydrogenase is able to convert glyceraldehyde 3-phosphate to 1,3-bisphosphoglycerate forming NADPH+H$^+$, an NAD-dependent glyceraldeyde-3-phosphate dehydrogenase wherein the NAD-dependent glyceraldeyde-3-phosphate dehydrogenase is able to convert glyceraldehyde 3-phosphate to 1,3-bisphosphoglycerate forming NADH+H$^+$, a butyrate kinase wherein the butyrate kinase is able to convert 4-hydroxybutyrate to 4-hydroxybutyryl-phosphate, a phosphotransbutyrylase wherein the phosphotransbutyrylase is able to convert 4-hydroxybutyryl-phosphate to 4-hydroxybutyryl-CoA; and optionally having a disruption in one or more genes selected from yneI, gabD, pykF, pykA, maeA and maeB.

22. The process of claim 1, wherein the genetically engineered biomass is from a recombinant host having a poly-4-hydroxybutyrate pathway, wherein the host has stably incorporated one or more genes encoding one or more enzymes selected from a succinyl-CoA:coenzyme A transferase wherein the succinyl-CoA:coenzyme A transferase is able to convert succinate to succinyl-CoA, a succinate semialdehyde dehydrogenase wherein the succinate semialdehyde dehydrogenase is able to convert succinyl-CoA to succinic semialdehyde, a succinic semialdehyde reductase wherein the succinic semialdehyde reductase is able to convert succinic semialdehyde to 4-hydroxybutyrate, a CoA transferase wherein the CoA transferase is able to convert 4-hydroxybutyrate to 4-hydroxybutyryl-CoA, and a polyhydroxyalkanoate synthase wherein the polyhydroxyalkanoate synthase is able to polymerize 4-hydroxybutyryl-CoA to poly-4-hydroxybutyrate.

23. The process of claim 1, wherein the genetically engineered biomass is from a recombinant host having stably incorporated one or more genes encoding one or more enzymes selected from: a phosphoenolpyruvate carboxylase wherein the phosphoenolpyruvate carboxylase is able to convert phosphoenolpyruvate to oxaloacetate, an isocitrate lyase wherein the isocitrate lyase is able to convert isocitrate to glyoxalate, a malate synthase wherein the malate synthase is able to convert glyoxalate to malate and succinate, a succinate-CoA ligase (ADP-forming) wherein the succinate-CoA ligase (ADP-forming) is able to convert succinate to succinyl-CoA, an NADP-dependent glyceraldeyde-3-phosphate dehydrogenase wherein the NADP-dependent glyceraldeyde-3-phosphate dehydrogenase is able to convert glyceraldehyde 3-phosphate to 1,3-bisphosphoglycerate forming NADPH+H$^+$, an NAD-dependent glyceraldeyde-3-phosphate dehydrogenase wherein the NAD-dependent glyceraldeyde-3-phosphate dehydrogenase is able to convert glyceraldehyde 3-phosphate to 1,3-bisphosphoglycerate forming NADH+H$^+$, a butyrate kinase wherein the butyrate kinase is able to convert 4-hydroxybutyrate to 4-hydroxybutyryl-phosphate, a phosphotransbutyrylase wherein the phosphotransbutyrylase is able to convert 4-hydroxybutyryl-phosphate to 4-hydroxybutyryl-CoA; and optionally having a disruption in one or more genes selected from yneI, gabD, pykF, pykA, maeA and maeB.

24. The process of claim 1, wherein the weight % of the catalyst is in the range of about 4% to about 50%, and the heating is at about 300° C.

25. The process of claim 1, wherein the catalyst is about 4% by weight calcium hydroxide and the heating is at a temperature of 300° C.

26. A biobased gamma-butyrolactone product produced by the process of claim 1.

27. The product of claim 26, wherein the gamma-butyrolactone product comprises less than 5% by weight of side products.

28. A poly-4-hydroxybutyrate biomass produced from renewable resources which is suitable as a feedstock for producing gamma-butyrolactone product, wherein the level of poly-4-hydroxybutyrate in the biomass is greater than 50% by weight of the biomass.

29. The biobased gamma-butyrolactone product of claim 26, wherein the gamma-butyrolactone in the product has 100% biobased carbon content.

30. The process of claim 1, wherein product is about 85% by weight or greater based on one gram of a gamma-butyrolactone in the product per gram of poly-4-hydroxybutyrate.

* * * * *